United States Patent
To et al.

(10) Patent No.: US 9,801,820 B2
(45) Date of Patent: Oct. 31, 2017

(54) PHARMACEUTICAL CORE-SHELL COMPOSITE POWDER AND PROCESSES FOR MAKING THE SAME

(71) Applicant: New Jersey Institute of Technology, Newark, NJ (US)

(72) Inventors: Daniel To, North Wales, PA (US); Rajesh Dave, Princeton, NJ (US); Catharina Knieke, Ludwigshafen (DE); Ecevit A. Bilgili, Woodbridge, NJ (US); Mohammed A. Azad, Harrison, NJ (US)

(73) Assignee: NEW JERSEY INSTITUTE OF TECHNOLOGY, Newark, NJ (US)

( * ) Notice: Subject to any disclaimer, the term of this patent is extended or adjusted under 35 U.S.C. 154(b) by 232 days.

(21) Appl. No.: 14/441,970

(22) PCT Filed: Nov. 8, 2013

(86) PCT No.: PCT/US2013/069128
§ 371 (c)(1),
(2) Date: May 11, 2015

(87) PCT Pub. No.: WO2014/074808
PCT Pub. Date: May 15, 2014

(65) Prior Publication Data
US 2015/0297521 A1  Oct. 22, 2015

Related U.S. Application Data

(60) Provisional application No. 61/725,301, filed on Nov. 12, 2012.

(51) Int. Cl.
*A61K 9/14* (2006.01)
*A61K 9/16* (2006.01)
(Continued)

(52) U.S. Cl.
CPC ............. *A61K 9/1676* (2013.01); *A61K 9/14* (2013.01); *A61K 9/141* (2013.01); *A61K 9/145* (2013.01);
(Continued)

(58) Field of Classification Search
CPC ...... A61K 9/141; A61K 9/145; A61K 9/1623; A61K 9/20; A61K 9/50; A61K 9/5165
See application file for complete search history.

(56) References Cited

U.S. PATENT DOCUMENTS 6,475,523 B1  11/2002  Staniforth
7,276,249 B2  10/2007  Ryde et al.
(Continued)

FOREIGN PATENT DOCUMENTS

CN  104902879 A  9/2015
JP  2009538315 A  11/2009
(Continued)

OTHER PUBLICATIONS

Chinese Office Action; dated Oct. 9, 2016 for CN Application No. CN201380059171.5.
(Continued)

*Primary Examiner* — Carlos Azpuru
(74) *Attorney, Agent, or Firm* — Mendelsohn Dunleavy P.C.

(57) ABSTRACT

A composite particle including a core with at least one carrier material; a fluidizing material layer on the surface of the core; and an outer layer comprising nanoparticles of an ingestible material distributed in at least one matrix-forming material. A process of making the composite particles includes the steps of dry coating carrier particles with a fluidizing material; preparing a suspension of nanoparticles of an ingestible material distributed in a matrix-forming material; and fluid bed coating the carrier particles with the
(Continued)

suspension. The process and products provide quick dissolving composite particles which can be used for delivery of poorly water soluble ingestible materials in suitable dosage forms. The process of the invention reduces or prevents particle agglomeration during fabrication of the composite particles to enable delivery and quick redispersion of nanoparticles of the ingestible material from a dosage form.

30 Claims, 28 Drawing Sheets

(51) Int. Cl.
*A61K 9/20* (2006.01)
*A61K 31/216* (2006.01)
*B05D 1/22* (2006.01)
*A61K 9/50* (2006.01)

(52) U.S. Cl.
CPC .......... *A61K 9/1611* (2013.01); *A61K 9/1623* (2013.01); *A61K 9/1652* (2013.01); *A61K 9/1682* (2013.01); *A61K 9/1694* (2013.01); *A61K 9/20* (2013.01); *A61K 9/2077* (2013.01); *A61K 9/501* (2013.01); *A61K 9/5078* (2013.01); *A61K 9/5089* (2013.01); *A61K 31/216* (2013.01); *B05D 1/22* (2013.01)

(56) References Cited

U.S. PATENT DOCUMENTS

| | | |
|---|---|---|
| 2004/0058009 A1 | 3/2004 | Ryde et al. |
| 2008/0050450 A1 | 2/2008 | Arnold et al. |

FOREIGN PATENT DOCUMENTS

| | | |
|---|---|---|
| JP | 2009541485 A | 11/2009 |
| JP | 2010501511 A | 1/2010 |
| WO | 2005112825 A | 4/2005 |
| WO | WO2008002568 A2 | 1/2008 |
| WO | WO2008066899 A2 | 6/2008 |
| WO | WO2014062446 A1 | 4/2014 |

OTHER PUBLICATIONS

Stober, Werner, and Arthur Fink. "Controlled Growth of Monodisperse Silica Spheres in the Micron Size Range." Journal of Colloid and Interface Science 26 (1968): 62-69.
Yang, Jun, et al. "Dry particle coating for improving the flowability of cohesive powders." Powder Technology 158.1 (2005): 21-33.
Chen, Yuhua, et al. "Fluidization of coated group C powders." AIChE journal 54.1 (2008): 104-121.
Chen, Yuhua, et al. "Fluidized bed film coating of cohesive Geldart group C powders." Powder Technology 189.3 (2009): 466-480.
Han, Xi, et al. "Simultaneous micronization and surface modification for improvement of flow and dissolution of drug particles." International Journal of Pharmaceutics 415 (2011): 185-195.
Watano, Satoru, et al. "Fine particle coating by a novel rotating fluidized bed coater." Powder technology 141.3 (2004): 172-176.
Chen, Yuhua, et al. "Granulation of cohesive Geldart group C powders in a Mini-Glatt fluidized bed by pre-coating with nanoparticles." Powder Technology 191.1 (2009): 206-217.
Knieke, C., et al., "Concentrated fenofibrate nanoparticle suspensions from melt emulsification for enhanced drug dissolution." Chemical Engineering & Technology 37.1 (2014): 157-167.
Knieke, Catharina, et al. "Sub-100 micron fast dissolving nanocomposite drug powders." Powder Technology 271 (2015): 49-60.
Azad, Mohammad A., et al. "Preparation of concentrated stable fenofibrate suspensions via liquid antisolvent precipitation." Drug development and industrial pharmacy 40.12 (2014): 1693-1703.
Knieke, C., et al. "A study of the physical stability of wet media-milled fenofibrate suspensions using dynamic equilibrium curves." Chemical Engineering Research and Design 91.7 (2013): 1245-1258.
International Preliminary Report on Patentability; dated May 21, 2015 for the corresponding PCT App. No. PCT/US2013/069128.
Hemati, M. R. K. V., et al. "Fluidized bed coating and granulation: influence of process-related variables and physicochemical properties on the growth kinetics." Powder Technology 130.1 (2003): 18-34.
European Search Report; dated Jul. 19, 2016 for EP Application No. EP13852722.1.
Chinese Office Action; dated Jun. 12, 2017 for CN Application No. CN201380059171.5.
English Translation of Chinese Office Action; dated Jun. 12, 2017 for CN Application No. CN201380059171.5.
Japanese Office Action; dated Aug. 29, 2017 for JP Application No. JP2015541920.

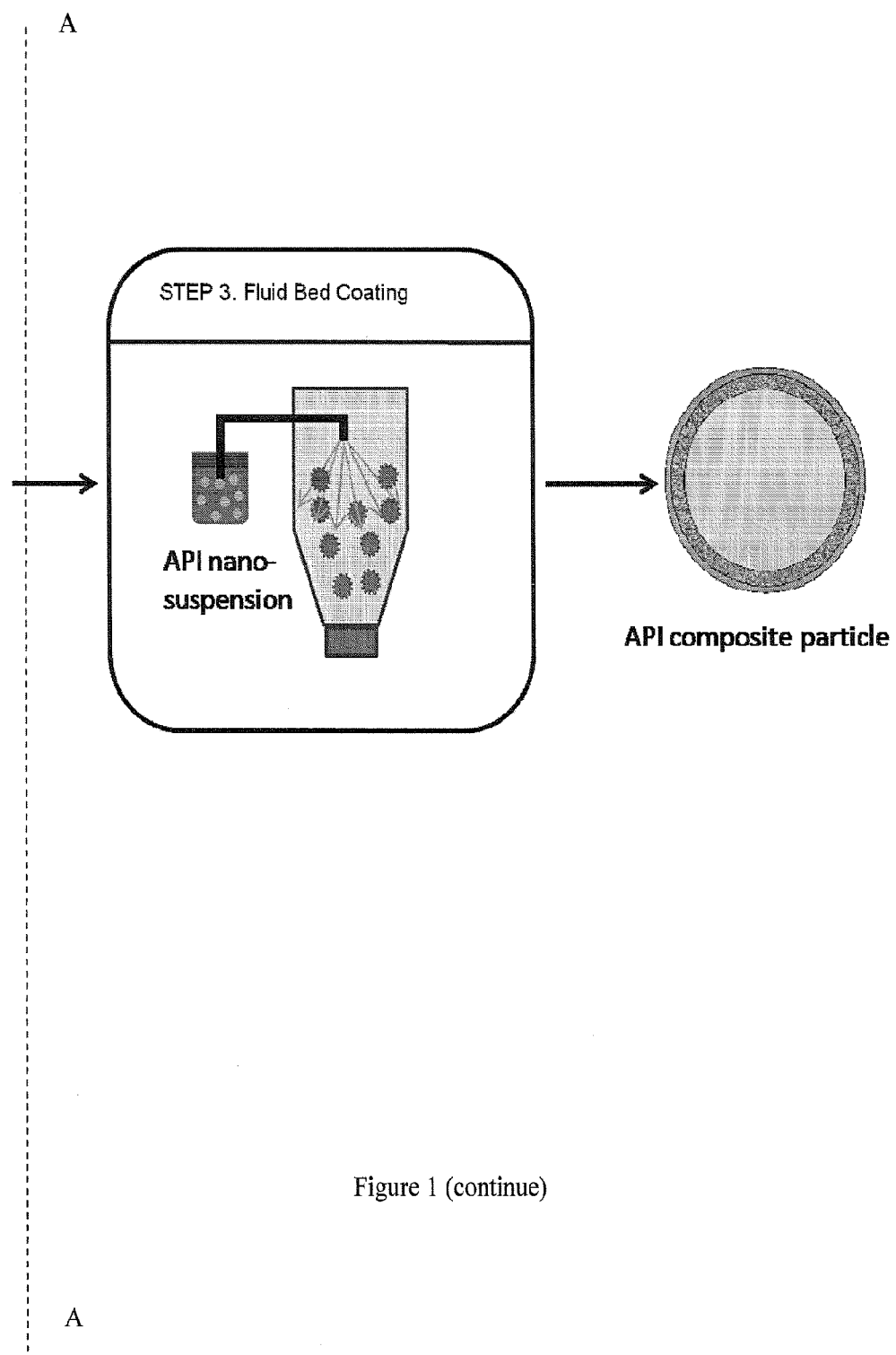
Figure 1 (continue)

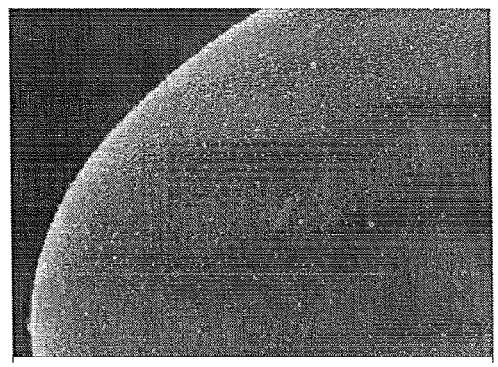 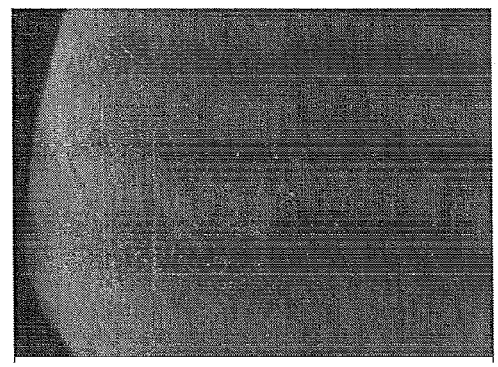
Figure 8A　　　　　　　　　Figure 8B
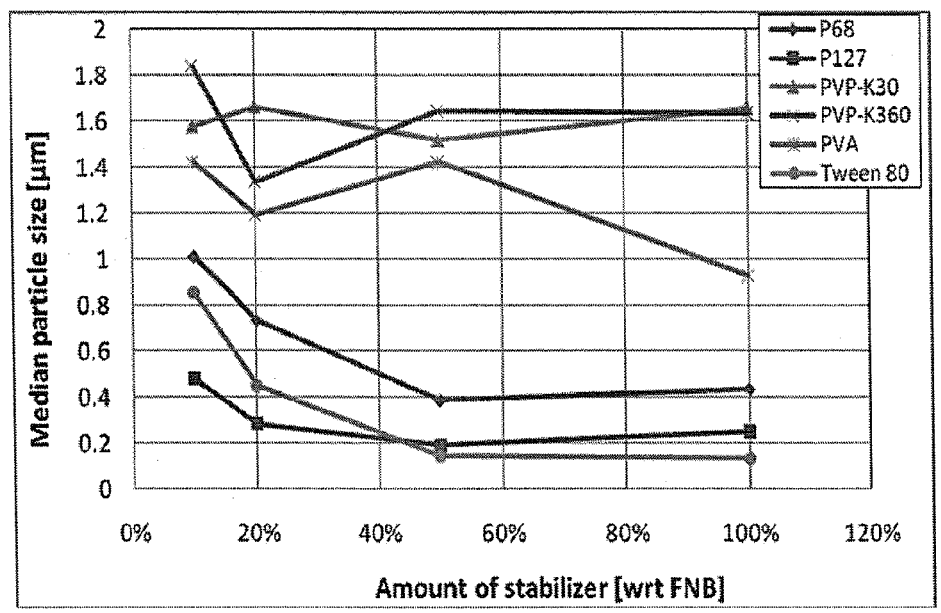
Figure 9

PHARMACEUTICAL CORE-SHELL COMPOSITE POWDER AND PROCESSES FOR MAKING THE SAME

BACKGROUND OF THE INVENTION

1. Field of the Invention

The present invention relates to a delivery composition for oral delivery of materials with poor water solubility. In particular, the invention is directed to particulate compositions consisting of individual, non-agglomerated composite particles using fine carrier particles to deliver nano-sized drug or active materials in oral dosage forms, and to processes for producing them.

1. Description of the Related Technology

Active pharmaceutical ingredients with poor solubility in water have low bioavailability, which leads to only a small portion of the pharmaceuticals being available to the target tissue after administration to a patient. Poor bioavailability is a significant problem encountered in the development of pharmaceutical compositions. Poorly water soluble pharmaceuticals, i.e., those having a water solubility of less than about 10 mg/ml, tend to be eliminated from the gastrointestinal tract before being absorbed into the circulation.

It is known that the rate of dissolution of a particulate pharmaceutical ingredient can increase with increasing surface area, i.e., decreasing particle size. Consequently, methods of making finely divided pharmaceutical compositions have been studied and efforts have been made to control the size and size range of particles in pharmaceutical compositions. For example, dry milling techniques have been used to reduce particle size and hence influence drug absorption. Wet grinding may also be beneficial in further reducing particle size, but aggregation/agglomeration or flocculation often restricts the lower particle size limit to approximately 10 microns (10,000 nm).

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptably large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process.

There is also a need for preparing dry dosage forms containing nanodrug particles. Simple spray drying, freeze drying or lyophilization may lead to poor flowing, low bulk density products. An alternate approach is to form core-shell composite particles; preferably with finer carrier particles. However, finer particles do not flow well, and they certainly do not fluidize well. Therefore, methods for improving their flow and fluidizability are desired. Yang et al. discloses several dry processing techniques for coating cohesive cornstarch powder with different size silica particles (Yang, J., Sliva, A., Banerjee, A., Dave, R. N., and Pfeffer, R., "Dry particle coating for improving the flowability of cohesive powders," *Powder Technology*, vol. 158 (2005) 21-22). The flowability of the coated cornstarch can in some cases be influenced by using nanosized silica coating.

Chen et al., "Fluidization of Coated Group C Powders," *AIChE Journal*, vol. 54 (2008) 104-121 discloses a process of dry coating cohesive, Geldart Group C powders with a very small amount of nano-sized particles. The dry coating is said to improve the fluidizability of the powders.

Chen et al., "Fluidized bed film coating of cohesive Geldart group C powders," *Powder Technology*, vol. 189 (2009) 466-480 discloses a process of dry coating cohesive Geldart group C powders process to reduce the interparticle force and improve the fluidization behavior of fine powders. Polymer film coating at an individual particle level is achieved on these pre-coated fine powders in a commercially available spouting fluidized bed (MiniGlatt).

U.S. Pat. No. 7,276,249 discloses a process of spray coating nanosuspensions onto large carrier particles. The coated fibrate compositions are said to have improved pharmacokinetic profiles and reduced fed/fasted variability. The fibrate particles of the composition have an effective average particle size close to about 2000 nm However, these large carrier particles have a relatively low surface area per unit weight of the product which does not allow for sufficient drug loading, which may necessitate a thicker coating layer, which can decrease the dissolution rate of the active ingredients.

A significant issue for prior art processes is irreversible agglomeration of the coated pharmaceutical particles often caused by poor drying methods, which typically leads to particle sizes much larger than 100 μm. The present invention provides a process to produce active pharmaceutical ingredient (API) composite powders that minimizes irreversible agglomeration and particle growth and achieves suitably redispersible nanoparticles which enhance the dissolution of poorly water soluble API's.

SUMMARY OF THE INVENTION

In a first aspect, the present invention is directed to a composite particle including a core with at least one carrier material and an outer layer comprising a material to be delivered, e.g. an active material, using the particle, such as an active pharmaceutical ingredient nanoparticles and a matrix-former.

Another aspect of the present invention is directed to a process for preparing a pharmaceutical composite particle, comprising steps of: 1) dry coating of fine carrier particles with a nanoparticle material, which is generally an inactive ingredient, to improve its fluidization; 2) preparing a stable nanosuspension of active ingredient-containing nanoparticles; and 3) coating the carrier particles in a process with a composition including the active ingredient-containing nanoparticles included in the nanosuspension.

BRIEF DESCRIPTION OF THE DRAWINGS

FIGS. 8A-8B are scanning electron microscopy (SEM) images of carrier particle surfaces after dry coating with 1% nano silica M5P (FIG. 8A) and 0.17% nano silica M5P (FIG. 8B), as carried out in accordance with Example 7.

FIG. 9 shows median particle sizes as a function of the amount of matrix-forming stabilizer used to emulsifying fenofibrate in accordance with Example 10.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In a first aspect, the present invention relates to process of making composite particles that contains an ingredient to be delivered in an oral dosage form. The process generally includes the steps of 1) preparing a nanosuspension of the ingredient to be delivered, and 2) coating carrier particles with a composition including the material to be delivered using the nanosuspension to produce composite particles. An exemplary embodiment of a process in accordance with the present invention is depicted in FIG. 1.

Figure 1:
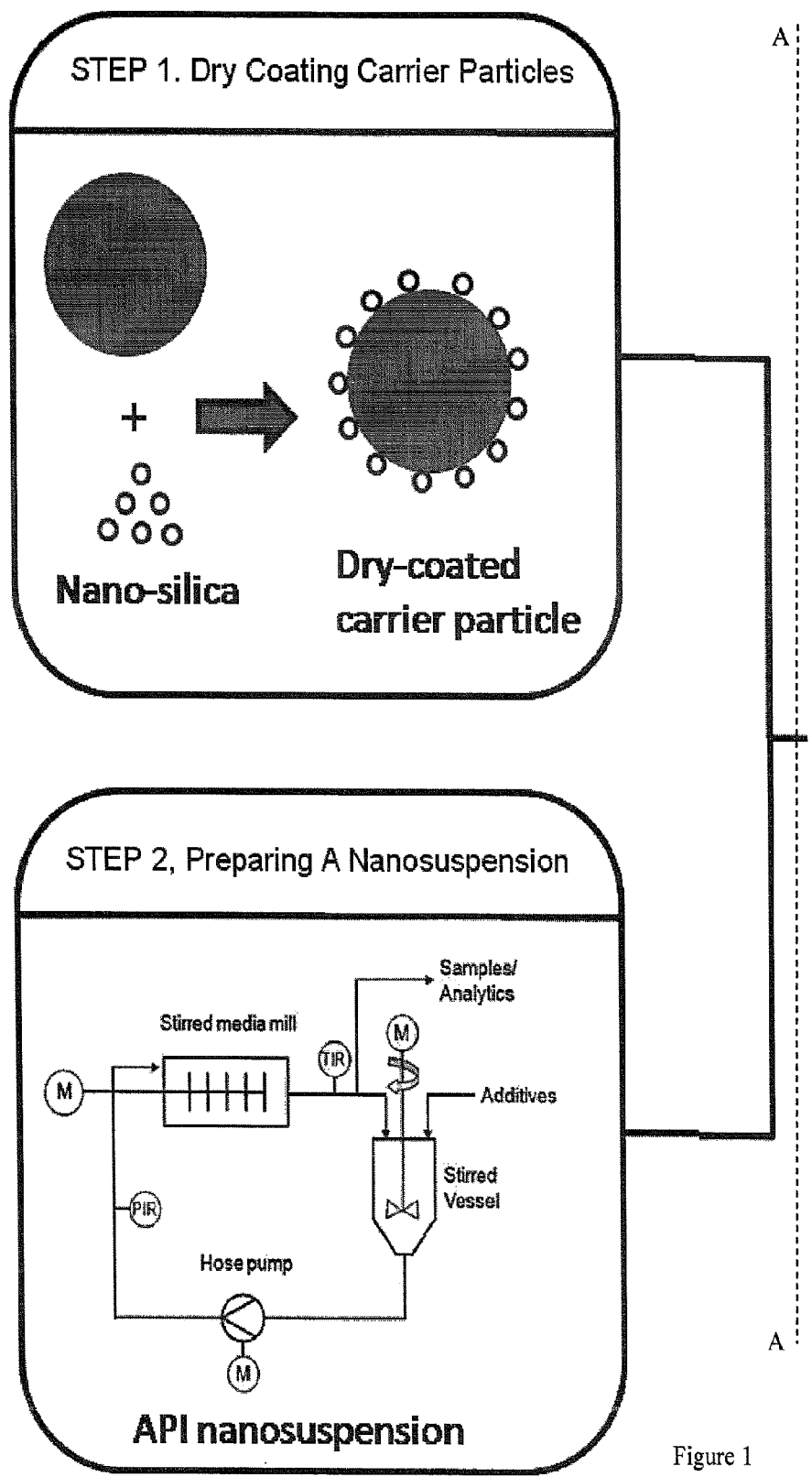
FIG. 1 is a schematic representation of one embodiment of the process in the present invention.
Figure 2:
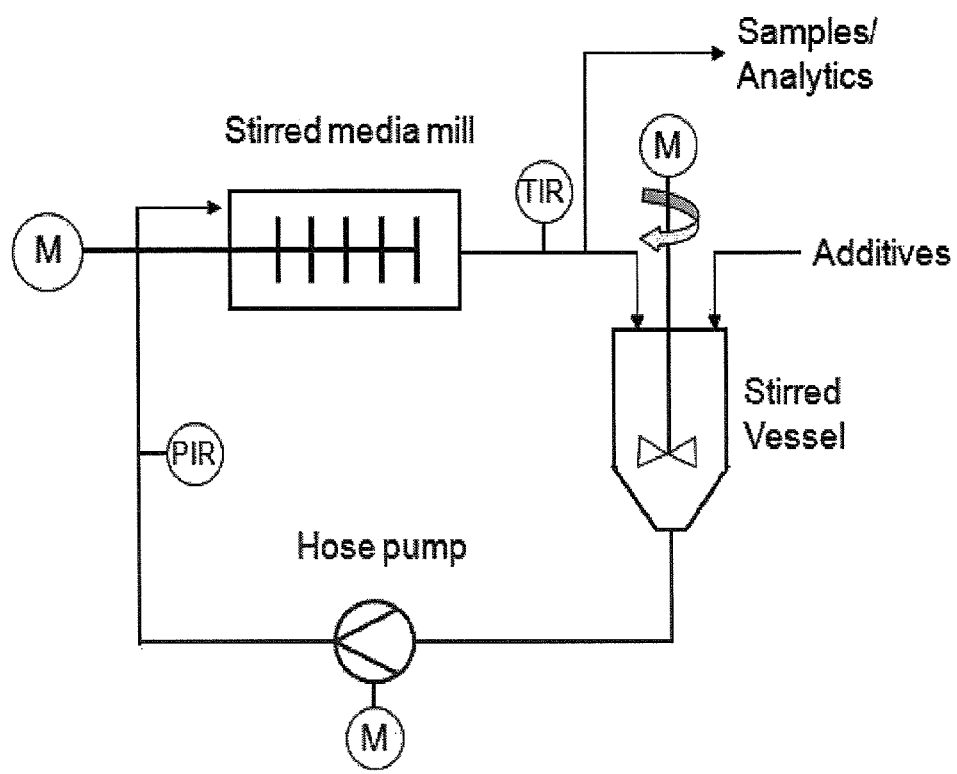
FIG. 2 is a schematic representation of a wet stirred media milling process that may be used in the present invention.

In step 1 of the process of FIG. 1, carrier particles are dry coated, as needed, with a coating material for the purpose of improving the flowability of the carrier particles and/or reducing the tendency of the carrier particles to agglomerate.

The carrier particles may be made from any material that is safe for ingestion by humans or animals and are typically made from a pharmaceutically acceptable material. Such materials are typically pharmaceutically inert, low cost and may be crystalline or amorphous. The carrier particles are usually made from inert materials that are preferably hydrophilic, and more preferably soluble or swellable. Preferably, the carrier particles comprise one or more materials that are on the FDA GRAS (generally regarded as safe) list and cleared for internal and/or pharmaceutical use, and are usually found in list of common excipients. A comprehensive list of materials that may be used in the carrier particles is disclosed in U.S. Pat. No. 6,475,523, which is incorporated in its entirety by reference. Examples of suitable materials for use as carrier particles include starches, modified starches, lactose, sucrose, polyols, celluloses, cellulose derivatives such as cellulose ethers including at least ethyl cellulose, methyl cellulose, and carboxymethyl cellulose, and mixtures thereof; or they can also be from a class of GRAS inorganic materials, for example, dicalcium phosphate. Particular examples of suitable carrier materials include potato starch, cornstarch, wheat starch, hydroxypropyl methyl cellulose, microcrystalline cellulose, lactose, mannitol, sorbitol, and other similar materials.

The carrier particles generally have a median particle size ranging from about 20 μm to about 200 μm, or from about 20 μm to about 50 μm. The carrier particles may in some embodiments consist of a plurality of particles with a narrow particle size distribution because carrier particles with wider size distributions that include both fine and coarse particles are more likely to agglomerate during mixing and coating. Finer carrier particles may provide the most benefit in terms of being able to provide sufficient drug loading in the coating layer.

An acceptable size range can be selected based on the width of the particle size distribution, which may be specified in terms of its span, defined as (d90-d10)/d50. Here, d90 indicates the size below which 90 percent volumetric distribution resides, and likewise, d50 is the median of the volumetric size distribution and d10 is the size below which 10 percent volumetric distribution resides. The span should be less than about 3, more preferably less than about 2. A span of up to 4 may also be acceptable, provided that the fines or coarse fractions do not have very long-tailed distributions. Preferably the d90 particle sizes are less than 300 μm and the d10 particle sizes are greater than 5 μm; particularly, when d50 is small.

The fluidizing material employed to coat the carrier material to form the coated carrier particle in the exemplary embodiment of FIG. 1 may be nanoparticles of, for example, silica. This coating material is employed to improve the flowability of the carrier particles in order to facilitate, for example, fluidization in subsequent coating steps, while at the same time ensuring that minimal agglomeration of the carrier particles will occur upon storage, handling and in further processing steps. Other nanoparticle materials may be employed including, for example, materials that have a relatively low dispersive surface energy of, for example, less than 60 mJ/m$^2$, or less than 40 mJ/m$^2$ and a median particle size of, for example, from 5 nm to 100 nm Preferably, the nanoparticles comprise one or more materials that are on the United States Food and Drug Administration's list of GRAS (generally regarded as safe) materials and are cleared for internal and/or pharmaceutical use. Examples of suitable nanoparticle materials for coating the carrier particle include nanoparticles of silica, alumina, titania, carbon black, aluminum calcium silicate, calcium silicate, magnesium silicate, potassium silicate, sodium silicate, sodium aluminosilicate, sodium calcium aluminosilicate, tricalcium silicate, silica aerogel, talc, iron oxide, other metal oxides and mixtures thereof.

The silica nanoparticles used in the present invention may be of any type, such as hydrophobic treated silica or fumed silica. Examples of suitable silicas include Aerosil R972 silica (Evonik), CAB-O-SIL EH-5 silica (Cabot), CAB-O-SIL M-5P silica (Cabot), CAB-O-SIL M-5DP silica (Cabot), AEROSIL® 200 Pharma (Evonik), AEROSIL® 200 VV Pharma (Evonik), AEROPERL® 300 Pharma (Evonik), OX-50 silica (Evonik), COSMO55 (Catalyst & Chemical Ind. Co. Ltd (Japan)), P-500 hydrophilic silica (Catalyst & Chemical Ind. Co. Ltd (Japan)) and TS530 silica (Cabot). In general, preferred are the fumed amorphous silicas with a specific surface area of greater than about 100 m$^2$/g. Typically, these fumed amorphous silicas are produced via gas-phase synthesis and undergo surface modification to alter their hydrophobicity. In some embodiments, more than one type of silica may be used in combination. For example, silica TS5 and silica R972 may be used together, as long as they are acceptable for the intended pharmaceutical application.

Hydrophilic silica may be obtained by hydrophobic treatment to make the silica hydrophobic. In one embodiment, the hydrophobic treatment of hydrophilic silica may be accomplished by treating the hydrophilic silica with dichlorodimethanolsilane. Any other suitable methods known to a skilled person that are capable of modifying silica to hydrophobic silica may be used. Hydrophobic silica, in addition to improving flow and fluidization properties, may aid in delaying the wetting of the coated API and delaying its initial release.

The weight amount of the nanoparticle material on the carrier particles is in the range from 0.1 to 10% by weight of the total weight of the dry-coated carrier particles. Alternatively, from 0.1% to 1.5% or from 1 to 5% by weight of nanoparticle material may be employed. It is believed that using high concentrations of nanoparticle material (i.e. much greater than 100% surface area coverage (SAC)) could dry coat the carrier particles and also leave silica particles available during the fluid bed coating process. This excess nanoparticle material is available to dislodge from the dry-coated carrier particles and dry coat the pharmaceutical composite powder during the subsequent fluid bed coating process.

The nanoparticle material coating on the carrier particles leads to reduced cohesion of the carrier particles. Such fine carrier particles are usually cohesive and cannot be fluidized. While the most reliable way to test if a carrier particle can be fluidized or not is by actually trying to fluidize it, indirect indications of improved fluidizability may also be gathered through reduced Angle of Repose (AoR) or increased flow function coefficient (FFC). Any GRAS nanoparticle materials that sufficiently reduce the AoR or increase FFC and subsequently show improved fluidization of the coated particles when they are subjected to fluidizing gas are acceptable as coating materials in the present invention. Coating with nanoparticles may change the powder flow properties and the AoR is expected to be less than 45 degrees and more preferably less than 40 degrees or even lower, while the FFC may increase to 6 or even higher, for example greater than 8.

Step 1 of the process of FIG. 1 is preferably performed as a dry-coating step. Apparatus for performing the dry coating of step 1 of FIG. 1 may be any suitable apparatus known to a skilled person. Suitable apparatus include, but are not limited to, a Comil (U3 Quadro Comil of Quadro Pennsylvania, U.S.), a LabRAM (Resodyne Minnesota, U.S.), a Magnetically Assisted Impact Coater (MAIC, Aveka Minnesota, U.S.), an acoustic mixer and a Fluid Energy Mill (FEM, Qualification Micronizer of Sturtevant Massachusetts U.S.). Other examples of dry coating devices include, the Hybridizer or Omnitex (Nara Machinary, Tokyo, Japan), the Mechanofusion or more recent versions such as Nobilta and Nanocular (Hosokawa Micron Powder Systems, Osaka, Japan), the Theta composer (Tokuju Corporation, Tokyo, Japan), and to some extent, any high intensity mixers, for example, the V-blender with agitation bar (PK Blend Master® Lab Blender, Patterson-Kelly, East Stroudsburg, Pa.) and (Cyclomix, Hosokawa Micron Powder Systems, Osaka, Japan).

Dry coating of the carrier particles can be accomplished in a relatively short time in the devices designed to perform dry coating. In contrast, some of the low intensity mixers may be used but require longer processing times. In all cases, larger scale devices would provide larger production rates without significantly changing the processing times. A person skilled in art would be able to develop a suitable scale-up strategy.

Figure 3:
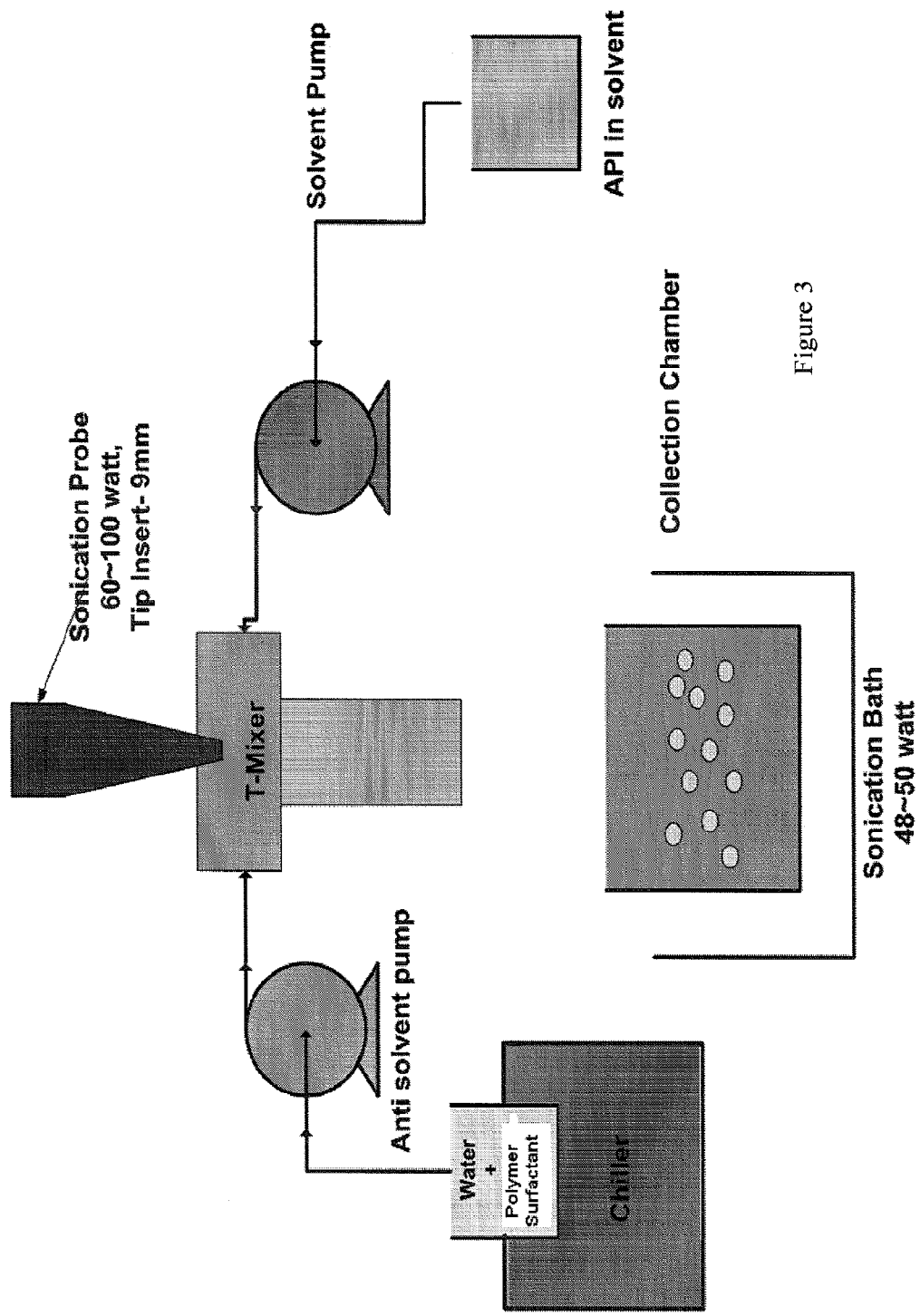
FIG. 3 is a schematic representation of a liquid antisolvent precipitation method that may be used in the present invention.
Figure 4:
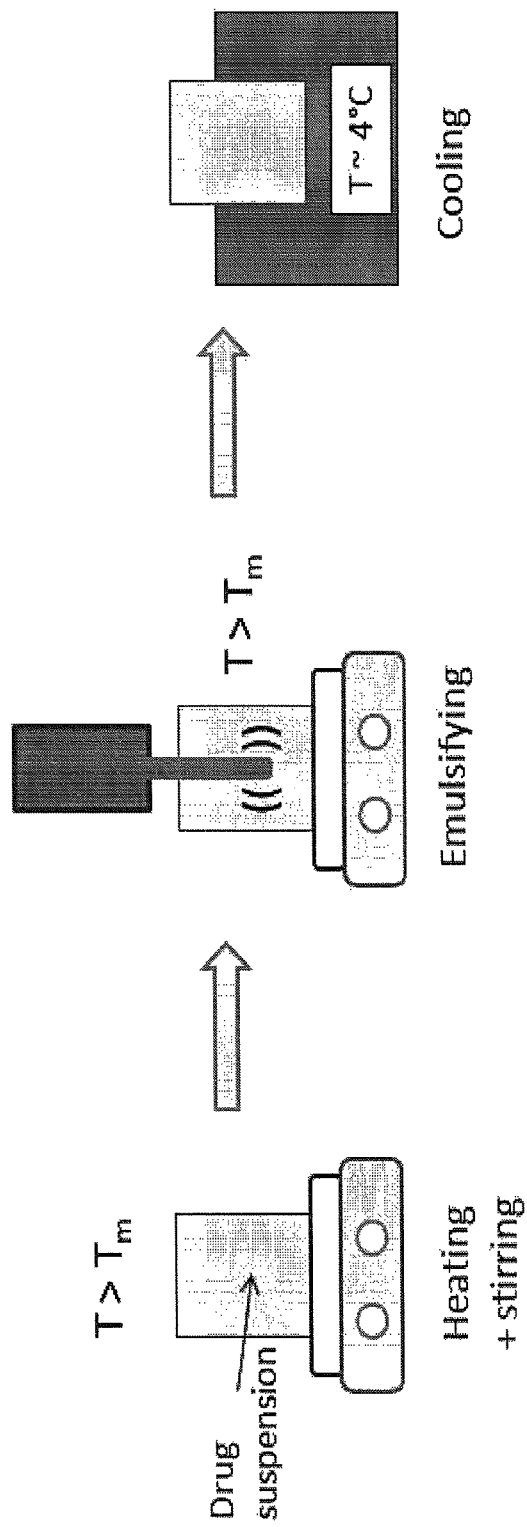
FIG. 4 is a schematic representation of a melt emulsification method that may be used in the present invention.

The operating conditions for dry coating may be established by a skilled person giving consideration, for example, to particle agglomeration and providing reduced angle of repose (AOR) values for the coated carrier particles. The degree of particle agglomeration may be determined by measuring the size of the coated particles in SEM images. The degree of agglomeration may also be estimated using the dispersion pressure titration in the Rodos/Helos system (Rodos and Helos, Sympatec, Lawrenceville, N.J., USA). A discussion of the pressure titration may be found in Han, X., Ghoroi, C., To, D., Chen, Y., Davé, R., "Simultaneous micronization and surface modification for improvement of flow and dissolution of drug particles (2011)." *International Journal of Pharmaceutics*, vol. 415, pp. 185-195, which is incorporated in its entirety by reference. The AOR may be measured using the procedure of ASTM D6393-99, "Bulk Solids Characterization by CARR Indices." For example, when the Comil is used, the impeller speed may be optimized to reduce the agglomeration (FIG. 3) as higher impeller speed increases agglomerate size for the dry-coated carrier particles.

The product after dry coating includes coated carrier particles that are depicted schematically in FIG. 1. The particles on the surface may be several particles thick. The nanoparticle material on the surface of the API-silica composite particles helps to minimize agglomeration by introducing modified surface properties in the form of a nano-sized surface asperity and modified surface energy. Though the carrier particles are often cohesive, the coated carrier particles have good flow properties and are fluidizable.

The surface area coverage (SAC) of the carrier particles with the nanoparticle material may be estimated by image analysis of SEM images of the dry-coated carrier particles. In some embodiments, the SAC of the dry-coated carrier particles is in the range of from 15% to 100%, in the range of from 25% to 100%, or in the range of from 35% to 100%. In some embodiments, the SAC may be proximate to 100%.

Fluidization of not otherwise fluidizable carrier particles is due to reduced cohesion upon dry coating based surface modification. In general, there are two factors that contribute to the inter-particle attraction, hence cohesion of such powders. The first factor is the material surface property generally represented by its surface energy or by the Hamaker constant. In general, a lower Hamaker constant or lower dispersive component of surface energy will lead to reduced inter-particle attraction, all else being equal, and thus reduced cohesion.

The second factor is also a surface property, and it is the roughness at the contact surface between two particles. With all else being equal, either very rough, i.e, roughness on the order of 100 nm or higher, or very smooth, i.e., atomic smoothness or roughness of less than a few nm, e.g., 5 nm, have higher inter-particle attraction than those which may be called nano-rough; i.e., having a surface roughness between 5 to 100 nm, for example measured using an Atomic Force Microscope. More preferably, a surface roughness between 7-30 nm is employed. Dry coating with nanoparticle materials having a particle size of 5-100 nm, and more preferably a particle size of 10-50 nm, and most preferably 20-50 nm, can thus lead to reduced cohesion due to imparted nano-scale surface roughness. There could be an additional effect of cohesion reduction if the dispersive component of surface energy of the nano-particle is in general low (<60 mJ/m$^2$, preferably <40 mJ/m$^2$), or alternately less than the original pharmaceutical powder.

Since cohesion reduction could occur due to one or both the factors listed above, in lieu of coating using nanoparticles, softer, deformable materials that have flaky nature and smear upon mixing may also be used. Such coatings also result in a low dispersive surface energy of the coated product. Thus coating may be also done with materials such as; magnesium stearate, stearic acid, leucin, amino acids, and other materials typically used in inhalation applications to impart dispersion through hydrophobic and/or low adhesion materials; see for example U.S. Pat. No. 6,475,523 that contains a comprehensive list of surface active molecules, the disclosure of which is hereby incorporated by reference. Thus such materials would replace silica or nano-sized, discrete particles with deformable/flaky materials. The reduction in cohesion occurs due to lower dispersive surface energy and could also be due to reduced surface roughness as a result of a softer material filling in voids in a rough surface resulting in a smoother surface.

The flow property of the dry-coated carrier particles may be evaluated using shear tests with a FT4 Powder Rheometer (Freeman Technology, Tewkesbury, UK) and Angle of Repose (AoR) measurements (Powder tester, Hosokawa Micron, Ltd., mm) The flow function coefficient (FFC) was used as an indicator of the flowability of a powder and is defined as the ratio of major principle stress to the unconfined yield strength. The FFC has been obtained in this work using a normal stress of 3 kPa. According to Schulze, FFC values can be separated into different regimes: i.e., FFC <1, not flowing; 1<FFC<2, very cohesive; 2<FFC<4, cohesive; 4<FFC<10, easy flowing, and FFC>10, free-flowing.

Another step that may be used in the process of the present invention, referenced as step 2 in FIG. 1, involves the preparation of a stable nanosuspension containing the ingredient to be delivered. The starting materials for step 2 may include a material to be delivered, a solvent, and one or more matrix-forming materials. The matrix-forming materials are sometimes referred to herein as "stabilizers" since the inclusion of the matrix-forming materials in the suspension tends to stabilize a nanosuspension of the material to be delivered to ensure that that the nanosuspenion of the materials in a liquid remains sufficiently stable in suspension for storage and use in subsequent coating processes. In this sense, a stable nanosuspension refers to a nanosuspension which does not undergo significant precipitation of the suspended materials and/or significant agglomeration of the suspended materials during storage and use.

The material to be delivered is typically a poorly water soluble particulate material. In some embodiments, two or more of these materials may be used in the present invention. Step 2 may include a plurality of steps, as needed for a particular material. For example, in some cases it may be necessary to reduce the particle size of the material to be delivered prior to forming the nanosuspension. Step 2 always involves a step of suspending the material to be delivered in a suitable liquid material to form a nanosuspension and thus the product step 2 is a stable nanosuspension wherein particles containing the material to be delivered are suspended in a liquid material.

Any material to be delivered may be suitable for the present invention as long as it can be provided in the form of nanoparticles. The invention is particularly useful for materials having a water solubility of less than 10 mg/ml, or less than 5 mg/ml. The amount of material to be delivered is selected to provide nanoparticles containing an amount of the material to be delivered in a range of from about 5 w/v % to about 50 w/v %, or from about 15 w/v % to about 40 w/v %, or from about 10 w/v % to about 30 w/v %, based on the volume of the nanosuspension. The material to be delivered is also referred to herein as the active material and may comprise, for example, an active pharmaceutical ingredient (API) or other suitable material as described elsewhere herein.

In some embodiments, pre-milling or another suitable particle reduction treatment of the material to be delivered may be needed before the suspension step. For example, the material may have an initial particle size too large for the suspension step, i.e. in the range of millimeters or larger.

One example of a pre-milling step employs a jet mill. In an exemplary embodiment, as-received fenofibrate (FNB) is pre-milled in a fluid energy mill (Micronizer, Sturtevant, Hanover, Mass.) to reduce the initial particle size, which is in the scale of millimeters. In the fluid energy mill, the FNB particles are accelerated by compressed air flow. Due to particle—particle and particle—grinding chamber wall collisions, FNB particles break into finer fragments. The grinding and feed pressures are set to 40 psi and 45 psi, respectively. The FNB particles are fed into the fluid energy mill by a screw feeder at a rate of about 12 g/min After the pre-milling, the FNB particle size was reduced to a median size (d50) of 11 µm and 90% passing size (d90) of 34 µm (Rodos/Helos system, Sympatec, N.J., USA, dispersing method: 0.1 bar.

The solvent used in the suspension step may be an aqueous solvent such as water, de-ionized (DI) water or distilled water, and such aqueous solvents are suitable when the drug material is nearly insoluble in water. In some embodiments, organic solvents such as acetone or ethanol may be suitable for use to make the suspensions of the present invention, as long as the drug does not have appreciable solubility in the solvent used. Particularly useful solvents are materials that are safe when ingested and/or are approved for human and/or animal consumption. Other examples of solvents that may be used include, tertiary butyl alcohol (TBA), tetrahydrofuran (THF), dimethyl sulfoxide (DMSO), dichloromethane, dimethyl formamide (DMF), methanol and mixtures thereof.

The matrix-forming materials of the present invention are used for the purpose of stabilizing the nanosuspension. The matrix-forming materials may include polymers and, optionally, surfactants. Some examples of suitable matrix-forming polymers include various grades of hydroxypropylcellulose (HPC), hydroxypropyl methylcellulose (HPMC), poly(vinyl alcohol) (PVA), poly(vinyl pyrrolidone (PVP), PVP-K360, PVP-K30, ammonio methacrylate copolymers, ethylcellulose, Plasdone 5630, hydroxyl methyl celluolose, hydroxyethyl cellulose (HEC), methyl cellulose (MC), carboxymethyl cellulose sodium salt, Povidone K15, gum acacia and combinations thereof.

Examples of suitable surfactants include sodium dodecyl sulfate (SDS), dioctylsulfosuccinate (DOSS), nonionic ethylene oxide/propylene oxide copolymers, Pluronic F-68 (PF-68, poloxamer 188), cetyltrimethylammonium bromide (CTAB), Pluronic F-127 (PF-127, poloxamer 407), Tween 80 (T-80, a polyethylene sorbitol ester), sodium alginate (SA), Tween-20, lecithin, sodium lauryl sulfate, monooleate, monolaurate, monostearate, stearylic alcohol, cetostearylic alcohol, tyloxapol, polyethoxylated castor oils such as Cremophor and mixtures thereof. The surfactants used in the nanosuspensions are preferably non-ionic surfactants.

The combination of the one or more surfactants and one or more matrix-forming polymers tend to cause a decrease in the surface tension and an increase in the viscosity of a suspension. A decrease in surface tension increases the nucleation rate and as a result the particle size decreases. Similarly, an increase in viscosity reduces the number of collisions and therefore reduces the rate of mass transfer from the solution to the growing solid-liquid interface. This tends to reduce agglomeration but may also increase the precipitation time. The adsorption of polymer and surfactant at the growing solid interfaces reduces the interfacial surface energy and inhibits particle growth. Therefore, the presence of the appropriate matrix-forming materials in the solution prevents substantial particle growth, which stabilizes the nanoparticles in the suspension against agglomeration.

The amount of matrix-forming materials in step 2 will result the matrix-forming materials comprising in the range of from 5 w/v % to 50 w/v %, or from 10 w/v % to 35 w/v %, or from 15 w/v % to 30 w/v % of the total volume of the nanosuspension. In some embodiments, the matrix-forming materials may further comprise a matrix enhancing material, such as mannitol lactose, sucrose, trehalose , Avicel PH101, Inutec SP1, microcrystalline cellulose, sorbitol, dextrose, Pharmatose, maltodextrose, xylitol, sugars and other polyols.

The function of the matrix enhancing material is to enhance the formation of a matrix to bind the API nanoparticles into a layer on the surface of the carrier particles. The addition of mannitol also leads to faster dissolution of API nanoparticles from the composite particles at the beginning of dissolution so that more drug is released before a cake starts to form.

In the exemplary embodiment of FIG. 1, step 2 includes a sub-step of stirred media milling, also called wet stirred media milling. A schematic representation of a suitable stirred media milling process is depicted in FIG. 2. In the embodiment of FIG. 2, the apparatus used for stirred media milling is a recirculation mill MicroCer (Netzsch, Exton, Pa., USA), which is equipped with a pin rotor. The grinding chamber has a volume of 80 ml and is lined with zirconia. Both the grinding chamber and stirred vessel are connected to an external cooling device (M1-.25A-11HFX, Advantage, Greenwood, Ind., USA) to dissipate heat generated during the grinding treatment. Pre-suspensions are prepared by adding a desired amount of matrix-forming materials to de-ionized water solution and mixing until the pre-suspension is homogeneous before added the material to be delivered, with stirring, into the pre-suspension. During the stirred media milling, the suspension is circulated between the media mill and a stirred vessel. Samples are taken at the outlet of the grinding chamber. Suitable conditions for stirred media milling are: a media filling ratio of the grinding chamber of 62.5% (v/v), a suspension flow rate of 120 ml/min, and a rotational speed of the rotor in the mill of 3200 rpm, which equals a maximum stirrer tip speed of 11.8 m/s.

The progress of the stirred media milling may be monitored through sampling the size of the particles. Small samples may be retrieved from the sample outlet of the grinding chamber. The sample is diluted with de-ionized water for particle size measurements. Particle size distributions are measured with a laser diffraction device LS 13 320 (Coulter Beckman, Brea, Calif.). A polarized intensity differential scattering (PIDS) obscuration water optical model may be employed. Particle size distribution may be computed by the software using Mie scattering theory by taking an appropriate refractive index (RI) value, for example of 1.55 for the fenofibrate particles, and 1.33 for the measurement medium (water).

In some embodiments, step 2 of FIG. 1 may also be accomplished using liquid anti-solvent precipitation (LASP) in an ultrasonically driven T-mixer. In addition to the T-mixer, other apparatus may also be used for the LASP sub-process. Examples include mixing chambers, Y-mixers, static mixers and a rotating packed bed. The LASP may provide some advantages such as being relatively rapid, less energy intensive and cost effective. In addition, the precipitation route provides flexibility to control particle size and distribution by manipulating physicochemical properties of the solution and antisolvent phases using matrix-forming materials.

In the embodiment depicted in FIG. 3, the T-mixer can enhance micromixing. In a T-mixer, streams of API suspension and antisolvent collide in a mixing zone, where high supersaturation is achieved in a short time. The generation of high supersaturation may be further improved by employing ultra-sonication. It is hypothesized that the cavitation developed by ultra-sonication causes the nanoparticles to form due to multiple reasons: (i) creation of turbulent flow conditions inside the system that ensure efficient mixing; (ii) atomization of organic solutions of the drug into very fine droplets during addition into the aqueous stabilizer solution, and (iii) reduced agglomeration of the newly formed particles.

The T-mixer used in this embodiment has a 2 inch ID (inner diameter) by 2 inch length cylindrical delrin (from McMaster Carr, Santa Fe Springs, Calif., USA). Two side holes of 0.0787 inch OD (outer diameter) are drilled to make inlets for antisolvent (matrix-forming materials dissolved in DI water) and organic solution (API in acetone). The T-mixer outlet of 0.1875 inch OD is also drilled for the exit stream of antisolvent and solution. The ultrasound pocket is drilled for the introduction of ultrasonic probe (Omni-ruptor 250 by Omni International Inc., USA), which have 0.5 inch ID. No specific sealing of ultrasound is employed to contain the fluid. The T-mixer opening is designed to fit the ultrasound probe, in order to ensure optimum fluid—nozzle contact. The solvent and antisolvent solutions are pumped through a stainless steel nozzle (0.01 inch. ID) at a flow rate of 16.5~17 and 55.1 ml/min into the T-mixer, respectively, using HPLC pumps (Model CP, Laballiance, Pa., USA). See FIG. 3.

The temperature of the antisolvent during T-mixing was maintained at 1° C. The API solution was maintained at room temperature. The batch size was 80 ml. In the 80 ml of suspension, 10 ml is API solution and 70 ml is antisolvent. Before precipitation, 20 ml of antisolvent was put in the collection chamber for quenching and the remaining 50 ml was pumped during the T-mixing. The collection chamber was kept in the sonication bath (VWR-B2500A-MTH, ultrasonic cleaner, VWR International, West Chester, Pa.) and the sonication was continued during the T-mixing sub-process. Then, the suspension was filtered with a 25 um sieve to discard possible chunks that are observed after the precipitation.

In some other embodiments, step 2 of FIG. 1 may also be accomplished using a melt emulsification sub-process, a schematic representation of which is depicted in FIG. 4. The melt emulsification sub-process may include the following steps. First, the micronized particles and the matrix-forming materials are dispersed in water and the suspension is heated to temperatures above the melting point of the material to be delivered. To ensure a complete melting and to reduce the viscosity of the melt, temperatures at least 10° C. above the melting point of the material to be delivered are achieved. Gentle stirring with a magnetic stirrer is applied during the heating process. Second, emulsification is carried out with an ultrasonic probe (Vibra Cell VC 750, Sonics & Materials, Inc., Newtown, Conn.) for appropriate times scales and at suitable intensities. During the emulsification step the suspension is held at elevated temperatures (10-15° C.+Tm) to avoid solidification of the melt. Third, rapid cooling of the hot emulsion in a thermostatic bath at 4° C. (NESLAB TRE 10, Thermo Electron Corporation, Newington, NH) until the API suspension reaches temperatures below 10° C. is employed.

The selection of matrix-forming materials (typically polymers and, optionally, surfactants) may be important to the stability of the nanosuspension. A sonication bath may be used to select effective polymers and/or surfactants and their concentrations for a particular material to be delivered. In the sonication procedure, the material to be delivered is dissolved in acetone to form a clear solution. The matrix-forming materials are dissolved in DI water by magnetic stirring. The solution of material to be delivered is added quickly into the aqueous solution of matrix-forming materials during sonication in the sonication bath (VWR-B2500A-MTH, ultrasonic cleaner, VWR International, West Chester, Pa.). The duration of sonication may be 1 minute including the initial solvent addition time. Then, the suspension is filtered with a 25 μm sieve to discard possible chunks. The suspension is stored at room temperature for 2 days. Those suspensions that are still suspended after 2 days undergo a sizing analysis. Before sizing, the suspensions are mixed properly for 1 minute using a vortex mixer or magnetic stirrer. The size may be measured in a laser diffraction size analyzer Beckmann Coulter LS 13-320 (Miami, Fla., USA). The matrix-forming materials and concentrations that result in the least particle growth and precipitation may be used for the present invention.

The particle size in the suspension may be monitored by a laser diffraction device such as a LS 13 320 (Coulter Beckman, Inc., Brea, Calif.). In addition, morphological evaluation of the particles may be conducted by scanning electron microscopy (LEO 1530 SVMP, Carl Zeiss, Peabody, Mass.). Digital images may be obtained at an accelerating voltage of 2 kV using an Inlens detector. The SEM samples may be prepared by diluting the suspensions in de-ionized water and subsequently spreading the diluted samples onto a cleaned Si-wafer. The wafer is then dried under dust-free conditions in a desiccator and coated with carbon in a BAL-TEC MED 020 (BAL-TEC AG, Balzers, Switzerland) to reduce charging effect during imaging.

The product of step 2 of FIG. 1 is a suspension containing the material to be delivered that is stabilized by the matrix-forming material(s). A stable suspension is considered to be a suspension that undergoes minimal particle agglomeration. The stability of the suspension may be assessed by storing the suspension at room temperature for 2 days. The particles are sample before and after the 2 day storage period. If there is no significant particle size growth, the suspension is considered to be stable.

In step 3 of FIG. 1, the suspension from step 2 is used to coat the carrier particles from step 1 using, for example, a fluid bed coating process. A more detailed schematic representation of a suitable fluidized bed coating process is depicted in FIG. 5. In the process of FIG. 5, the coated carrier particles are fed to a fluidized bed coating chamber. Heated air is blown into the chamber to circulate the particles in the chamber. The suspension including material to be delivered is then pumped to a nozzle, which sprays atomized suspension into the fluidized bed coating chamber. The fluidized bed coating may be accomplished through top spray coating, bottom spray coating, tangential spray coating, or any other suitable method. A Mini-Glatt 9550, manufactured by Glatt of New Jersey, U.S. may be used as a suitable apparatus for the fluidized bed coating process. A Mini-Glatt 9550 is shown in FIG. 2 configured for top-spray fluidized bed coating.

The suspension is sprayed into the fluidized bed coating chamber, after being atomized, as fine droplets. The fine droplets attach to the surface of the carrier particles and form a layer comprising the particles of material to be delivered and matrix-forming material, after the solvent from the suspension is evaporated.

In some embodiments it may be desirable to blend small amount of silica, which may be stabilized silica, into the fluid bed coating chamber, in some cases at periodic intervals. The silica may function to reduce or prevent agglomeration during the fluidized bed coating process. Silica suitable for this purpose may have a median particle size in the range of from 100 nm to 500 nm, and is preferably amorphous colloidal silica. Silica particles with a diameter of 180 nm or larger can be prepared using the well-known Stötler process (see e.g. "Controlled growth of monodisperse silica spheres in the micron size range," *Journal of Colloid and Interface Science*, Volume 26, Issue 1, January 1968, Pages 62-69, Werner Stötler, Arthur Fink, Ernst Bohn doi:10.1016/0021-9797(68) 90272-5). The silica employed in this step is different from the silica used for coating the carrier particles, which has a smaller median particle size. The silica used in this step is preferably stabilized against aggregation. Conventional techniques may be used to stabilize the silica particles, including increasing ionic strength with NaOH, or by adjusting the pH of the silica solution.

The silica that may be used for blending with the spray of the API nanosuspension may be selected from Aerosil R972P (or pharmaceutical grade R972P), and other examples include, CAB-O-SIL EH-5 silica (Cabot), CAB-O-SIL M-5P silica (Cabot), CAB-O-SIL M-5DP silica (Cabot), AEROSIL® 200 Pharma (Evonik), AEROSIL® 200 VV Pharma (Evonik), AEROPERL® 300 Pharma (Evonik).

The droplet size of the sprayed suspension may be important for the fluidized bed coating performance and the quality of the final composite particles. Larger droplet sizes may create difficulties in drying and subsequently lead to the formation of undesirable agglomerates. On the other hand, smaller droplet sizes may result in the loss of material to be delivered due to rapid evaporation of solvent before the droplets reach the surface of the dry-coated carrier particles. The droplet size of a sprayed suspension may be measured using the Malvern Spraytec system (Malvern Instrument Inc., UK) on a nozzle with an orifice of 0.5 mm, located at a distance of 15 cm from the laser beam and at a position of 15 cm from the focal lens.

The droplet size of the sprayed suspension may be influenced by the polymer concentration in the suspension. The mean droplet size increases nonlinearly with the polymer concentration, because a suspension containing a high polymer concentration tends to form a highly viscous material and require more energy in order to be atomized into fine droplets. Thus, a high polymer concentration in the suspension (thus a higher viscosity suspension) may require a higher input energy to atomize the solution to produce sufficiently small droplets.

The preferred droplet size is less than the size of the carrier particles. In some embodiments, the preferred droplet size is in the range from 5 μm to 15 μm, or in the range from 7 μm to 12 μm. Also, in some embodiments it may be advantageous to ensure that the droplets of the sprayed suspension have narrow droplet size distributions, to encourage homogenous particle layer formation. It is preferred that the ratio of the d90-d10 and the d50 is equal to or less than 2. A wider distribution could result in spray drying of the fine fraction, while the coarse fraction could promote agglomeration.

The spray rate for spraying API nanosuspension may also influence the fluidized bed coating performance. Lower polymer concentrations in the API nanosuspension may allow use of a higher spray rate. The spray rate, however, must be balanced with the fluidizing velocity. The fluidizing velocity can be chosen such that the powder can be adequately fluidized. High spray rates can lead to humid conditions that can induce agglomeration, while low spray rates can lead to dry conditions that induce spray drying. The spray rate may be correlated with the droplet size distribution, where the droplet size distribution typically varies linearly with spray rate and is inversely proportional to the square of the pressure.

A suitable fluidization velocity in a Mini-glatt apparatus for reducing agglomeration during fluidized bed coating from 1 cm/s to 10 cm/s, or preferably 3 to 7 cm/s. The spray rate should be controlled such that the environmental conditions inside the fluidized bed are within the limits of 25-40% RH and 25-30° C.

Depending on the scale of the fluidized bed, the fluidization flow rate (the product of the superficial gas velocity and cross-sectional area of the bed), the spray rate and the atomization pressure can be controlled to keep the superficial gas velocity and droplet size distribution within desired limits, while still keeping the environmental conditions inside the bed within desired limits Smaller size carrier particles may require lower fluidizing velocities than larger carrier particles. This lowers the fluidizing flow rate that can be used during fluidized bed coating. Additionally, the spray rate will may have to be lowered to compensate for the change in gas velocity. Ultimately this can lead to significantly longer processing times.

In some embodiments, spraying of the suspension may be accomplished using an intermittent spray technique. Intermittent spraying is achieved by periodically spraying the polymer solution for a set interval and then discontinuing spraying for a set interval in which time some drying will occur. One suitable intermittent spraying cycle may employ a 120 second spraying period and a 120 second non-spraying period. Other suitable spraying periods may range from 20 seconds to 3 minutes with non-spraying periods also ranging from 20 seconds to 3 minutes, without requiring that both the spraying and non-spraying periods are the same.

Figure 6:
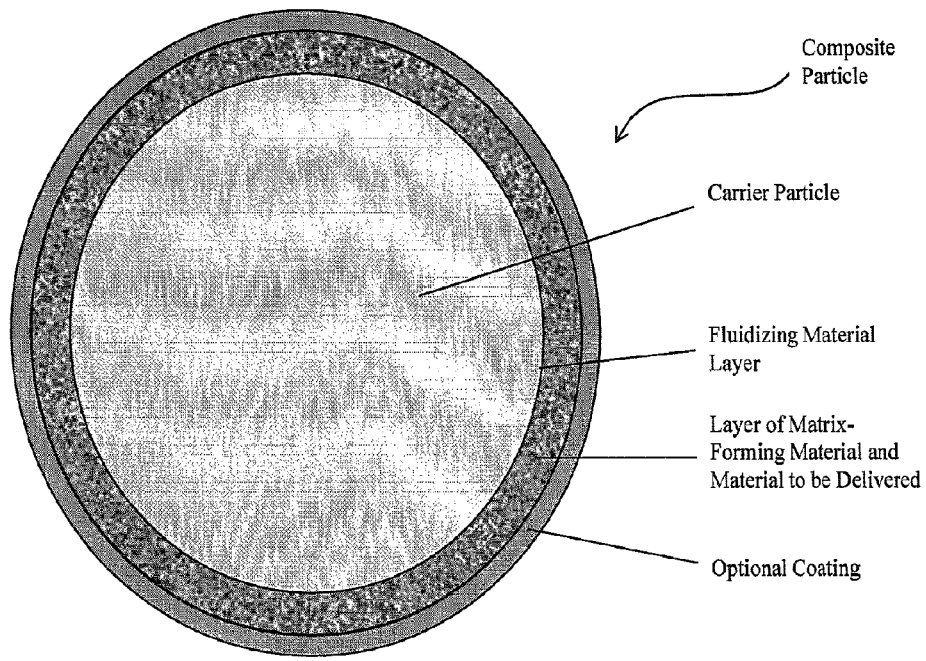
FIG. 6 is a schematic representation of a composite particle of the present invention.

The suspension droplets on the surface of dry-coated carrier particles form a layer of the material to be delivered and the matrix-forming material upon evaporation of the solvent. The final product of the process of the present invention is composite particles, as depicted in FIG. 6. The composite particle has a core that is derived from the carrier particle. On the surface of the carrier particle, there is a partial or complete layer of material to improve the flow properties of the carrier particle, e.g. silica. On the outside of this layer, there is a layer formed from a combination of particles of the material to be delivered and matrix-forming material.

The outer material layer need not cover the entire surface of the carrier particle. The surface area coverage (SAC) of the carrier particles with the outer layer may be in the range of from 15% to 100%, in the range of from 25% to 100%, or in the range of from 35% to 100%. In some embodiments, the SAC may be proximate to 100% and typically a higher SAC will be desirable to provide maximum loading of the material to be delivered. The outer layer has a thickness in the range from about 1 µm to about 10 µm, or from about 2 µm to about 7 µm, or from about 2 µm to about 5 µm. The material to be delivered may be any suitable material. In some embodiments, the material to be delivered is a material that exhibits poor water solubility. Exemplary materials are active pharmaceutical ingredients (API's), nutritional supplements, vitamins, minerals or other ingestables. Exemplary API's include fenofibrate, Griseofulvin, ibuprofen, Itraconazole, Naproxen, sulfamethoxazole , phenylbutazone, azodicarbonamide, Danazol, albendazole, Nifedipine, Cilostazol, Ketoconazole, Budenoside, loviride, Glimepiride, biphenyl dimethyl dicarboxylate, digitoxin, paclitaxel, predinisolone acetate, hydrocortisone acetate and any suitable mixtures thereof.

The present invention may include an optional step of further coating the composite particles with an optional layer for protection, reduced particle cohesion and/or controlled release. Any conventional methods and/or materials may be used in the present invention for coating the composite particles with this optional layer, if desired. The optional layer may have thickness in the range from 1 µm to 5 µm, or from 1 µm to 3 µm.

The composite particles can release the material to be delivered from the particle quickly. A dispersion of the composite particles may be evaluated by size measurement of particles dispersed into a solvent. For example, 100 mg of composite particles was added to 8 ml of DI water in a vial. The vial was gently mixed by hand-shaking for 30 seconds. The vial was then allowed to remain at rest for 2 minutes. The size distribution of the particles in the solution was measured via laser diffraction. The composite particles may release at least 90% of the particles containing the material to be delivered in 10 minutes, preferably in 5 minutes, and most preferably in 2 minutes.

The composite particles of the invention are designed to deliver ingestible materials such as active pharmaceutical ingredients (APIs), nutritional supplements, vitamins or other ingestible materials and mixtures thereof. The composite particles can be used as such or can be formulated into any suitable dosage form such as tablets, hard capsules, soft capsules, chewables, pouches or sachets, orally disintegrating tablets or lozenges, wafers, and pills. The composite particles may also be incorporated into other ingestible materials such as gels or chewing gums.

The invention can be practiced with a wide variety of drug substances. The drug substance preferably is present in an essentially pure form. The drug substance may be poorly soluble and must be soluble in at least one liquid medium. By "poorly soluble" it is meant that the drug substance has a solubility in an aqueous medium of less than about 10 mg/ml, and preferably of less than about 1 mg/ml.

Suitable drug substance can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-phannaceuticals, sex hormones (including steroids), anti-allergic agents, stimulants and anoretics, sympathomimetics, thyroid agents, vasodilators and xanthines. Preferred drug substances include those intended for oral administration. A account of these classes of drugs and a listing of species within each class can be found in Martindale, the extra Pharmacopoeia, Twenty-ninth Edition, the Pharmaceutical Press, London, 1989, the disclosure of which is hereby incorporated by reference in its entirety. The drug substances are commercially available and/or can be prepared by techniques known in the art.

The composite particles may contain, for example, about 0.01 to 50 wt %; or, 0.1 to 40 wt % of active or material to be delivered, about 0.5-4 wt % of matrix-forming material, about 0.05 to about 0.3 wt % of surfactant, about 1.0-3.0 wt % of fluidizing material and about 68-91 wt % of carrier material.

EXAMPLES

Example 1

Figure 7:
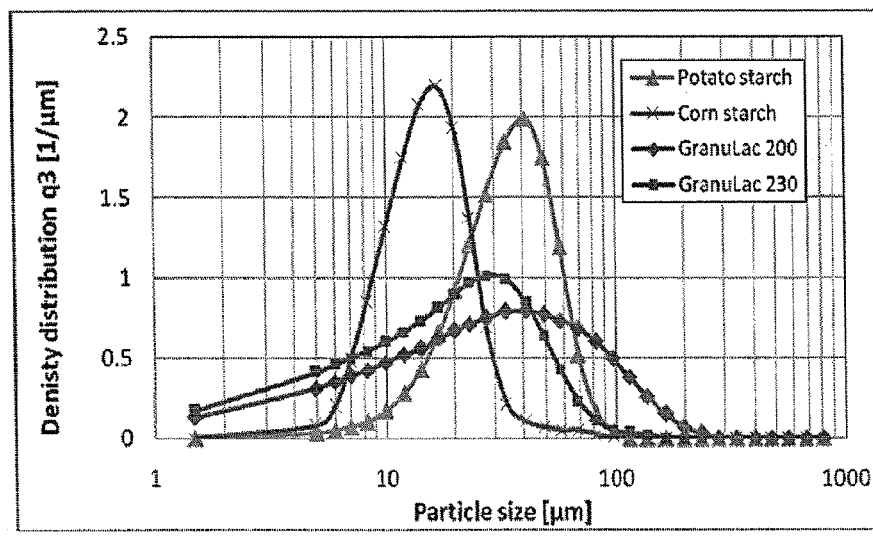
FIG. 7 show the particle size distribution of several carrier particles used in Example 1.

Potato starch (PS), a carrier material, was dry coated with silica nanoparticles (CAB-O-SIL® MSP, a hydrophilic silica, and Aerosil R972P-a hydrophobic silica). Particle size distributions of carrier materials were measured via laser diffraction at 0.5 bar dispersion pressure (Helos, Sympathec). The particle size distribution of the carrier particles are shown in FIG. 7. The starting materials used in this and the following examples are listed in Table 1.

TABLE 1

Dry-coating materials

| Material | Trade name | Manufacturer | Sauter mean diameter |
|---|---|---|---|
| Potato starch (PS) | — | Bob's Red Mill | 28 µm |
| Corn starch (CS) | — | Argo | 14 µm |
| Lactose | GranuLac 200, GranuLac 230 | Meggle | 20 µm, 14 µm |
| Fumed silica (hydrophilic) | CAB-O-SIL® M5P | Cabot Corporation | ~15 nm |
| Fumed silica (hydrophobic) | Aerosil R972P | Evonik | ~25 nm |

The potato starch powder was homogenously mixed with silica nanoparticles in a V-blender (Blend Master from Patterson Kelley). The V-blender was operated at filling level of about 40% with speed of 27 rpm for 5 minutes. The dry coating was carried out in either a magnetically assisted impact coating (MAIC) process or a Comil The device for MAIC was self-constructed by the inventors. 30 g of potato starch and silica nanoparticles were fed to the device, which had a magnet to powder ratio of 2:1 with voltage at about 36 V, 36 Hz for 10 minutes.

Regarding the Comil, it was a U3 QUADRO COMIL (Quadro) with a screen size 457 µm. The impeller was rounded with rotational speed of 2600 rpm. 30 g of potato starch and silica nanoparticles were fed to the Comil at a feed rate of 20 g/min with a screw feeder. The dry coating with Comil was only for one pass.

The flow properties of the dry-coated carrier particles were measured. Flow function coefficient (FFC) was measured by a Powder Rheometer FT4 from Freeman Technology. Angle of Repose (AoR) was measured by a Powder tester from Hosokawa. It was determined that 0.17% M5P on potato starch can be related to 100% theoretical surface area coverage (SAC). Flow properties of the dry-coated potato starch are given in Table 2.

TABLE 2

Flow properties of dry-coated carrier particles

| Silica M5P Content (%) | Coating Method | Bulk Density (g/cc) | FFC | Angle of Repose (°) |
|---|---|---|---|---|
| 0 | — | 0.63 | 3 | — |
| 0.1 | Comil | 0.87 | >10 | 29.2 |
| 0.17 | | 0.85 | >10 | 29.1 |
| 1 | | 0.73 | 8 | 32.3 |
| 0.1 | MAIC | 0.89 | >10 | 28.3 |
| 0.17 | | 0.89 | >10 | 28.8 |
| 1 | | 0.81 | >10 | 29.2 |

Both the MAIC and Comil produced excellent flow properties for potato starch. The surface of the PS is homogeneously covered with nanosilica (FIGS. 8A-8B). Higher silica content brings better coverage of the PS surface (FIG. 8A with 1% M5P vs. FIG. 8B with 0.17% silica).

Example 2

Corn starch (CS), a carrier material, was dry coated with silica nanoparticles (CAB-O-SIL® M5P-a hydrophilic silica). The carrier particle size and the nanosilica particle size are given in Table 1.

The corn starch powder was homogenously mixed with silica nanoparticles in a V-blender (Blend Master from Patterson Kelley). The V-blender was operated at filling level of about 40% with speed of 27 rpm for 5 minutes. The dry coating was carried out in a Comil. The Comil was a U3 QUADRO COMIL (Quadro) with a screen size 457 µm and 152 µm. The impreller was rounded with rotational speed of 1300 rpm. The mixture of corn starch and silica nanoparticles was fed to the Comil at a feed rate of 5 g/min or 10 g/min with a screw feeder. The dry coating with Comil was conducted for one pass or two passes. The flow properties of the dry-coated corn starch are given in Table 3.

TABLE 3

Flow properties of dry-coated carrier particles

| Silica M5P content | Impeller speed | Mesh size | Feed rate | Pass # | AoR* [°] |
|---|---|---|---|---|---|
| Uncoated corn starch | | | | | 66.5 |
| 0.1% | 1300 rpm | 457 µm | ~10 g/min | 2 passes | 52.4 |
| 0.56% | 1300 rpm | 457 µm | ~10 g/min | 2 passes | 41.4 |
| 1.12% | 1300 rpm | 457 µm | ~10 g/min | 2 passes | 40.5 |
| 0.56% | 1300 rpm | 152 µm | ~5 g/min | 1 pass | 41.1 |
| 0.56% | 1300 rpm | 152 µm | ~5 g/min | 2 passes | 40.7 |
| 1.12% | 1300 rpm | 152 µm | ~5 g/min | 1 pass | 42.8 |
| 1.12% | 1300 rpm | 152 µm | ~5 g/min | 2 passes | 41.1 |

Example 3

Corn starch (CS), a carrier material, was dry coated with silica nanoparticles (CAB-O-SIL® MSP, a hydrophilic silica). The carrier particle size and the nano silica particle size are given in Table 1.

The corn starch powder was homogenously mixed with silica nanoparticles in a V-blender (Blend Master from Patterson Kelley). The V-blender was operated at filling level of about 40% with speed of 27 rpm for 5 minutes. The dry coating was carried out in a LabRam (Resodyn Acoustic Mixers, Inc). The dry coating with the LabRam was conducted with 50 g of a mixture of carrier particles and silica nanoparticles in a LabRam with jar volume of 500 ml. The filling level is about 15%. The LabRam operation conditions and flow properties of the dray-coated corn starch are given in Tables 4 and 5.

TABLE 4

Dry coating of Corn starch

| Silica M5P content | Intensity | Acceleration [G's] | Time | AoR [°] | Bulk density | FFC |
|---|---|---|---|---|---|---|
| 0.1% | 70% | 72 | 5 min | 48.6 | | |
| 0.25% | 70% | 72 | 5 min | 42.1 | | |

TABLE 4-continued

Dry coating of Corn starch

| Silica M5P content | Intensity | Acceleration [G's] | Time | AoR [°] | Bulk density | FFC |
|---|---|---|---|---|---|---|
| 0.56% | 70% | 72 | 5 min | 40.8 | | |
| 1.12% | 70% | 72 | 5 min | 41.6 | | |
| 0.56% | 70% | 72 | 5 min | 40.8 | 0.705 g/cm3 | >10 |
| 0.56% | 50% | 55 | 5 min | 42.3 | | |
| 0.56% | 100% | 102 | 5 min | 37.9 | | |
| 0.56% | 70% | 72 | 10 min | 41.2 | | |

The batch size and the intensity of the LabRam (at the same acceleration) may affect AoR. It was observed that increasing both lead to AoR reduction (better flow properties). See Table 5. Higher intensities lead to more intense collisions/higher shear stress between host and guest particles, which improve the coating quality. The use of a larger batch size might improve the flow properties because there would be more particle to particle collisions during the same period of time

TABLE 5

Dry coating of Corn starch

| Batch size | Filling level | Intensity | Acceleration [G's] | Time | AoR [°] |
|---|---|---|---|---|---|
| 50 g | 15% | 70% | 72 | 10 min | 41.2 |
| 150 g* | 45% | 100% | 71 | 10 min | 34.5 |

Example 4

Lactose (GranuLac 200), a carrier material, was dry coated with silica nanoparticles (CAB-O-SIL® MSP, a hydrophilic silica). The carrier particle size and the nano silica particle size are given in Table 1.

The lactose powder was homogenously mixed with silica nanoparticles in a V-blender (Blend Master from Patterson Kelley). The V-blender was operated at filling level of about 40% with speed of 27 rpm for 5 minutes. The dry coating was carried out in a LabRam (Resodyn Acoustic Mixers, Inc). The dry coating with the LabRam was conducted with 150 g of a mixture of carrier particles and silica nanoparticles in a LabRam. The LabRam operation conditions and flow properties of the dray-coated corn starch are in Table 6.

TABLE 6

Dry coating of Corn starch

| Lactose | Silica M5P content | Time | Intensity/ acceleration | FFC | Fluidizible? |
|---|---|---|---|---|---|
| GranuLac 200 | — | — | — | 2.5 | No |
| GranuLac 200 | 1% | 10 min | 100%/68 G's | 5.2 | Yes |
| GranuLac 200 | 1.5% | 10 min | 100%/68 G's | 6.0 | Yes |
| GranuLac 230 | 1% | 10 min | 100%/68 G's | 4.7 | No |

Example 5

As-received fenofibrate material was pre-milled in a fluid energy mill (Micronizer, Sturtevant, Hanover, Mass.) to reduce the initial API particle size for the wet media milling In the fluid energy mill the particles were accelerated by a compressed air flow and due to particle-on-particle impacts as well as collisions with the grinding chamber wall, the particles break to finer fragments. In the experiments the grinding pressure was set to 40 psi and a feed rate of approximately 12 g/min was realized using a screw feeder. After fluid energy milling the fenofibrate particle size was reduced to d50=16 μm and d90=29 μm. Some of the materials used in this and the following examples are listed in Table 7.

TABLE 7

Materials for wet stirred media milling

| Material | Abbreviation | Function | Manufacturer |
|---|---|---|---|
| Fenofibrate | FNB | API | Jai Radhe Sales, Ahmedabad, India |
| De-ionized water | DI water | Dispersion medium | — |
| Hydroxypropyl methylcellulose E3 | HPMC E3 | Polymeric stabilizer | Dow Chemicals |
| Sodium dodecyl sulfate | SDS | Surfactant stabilizer, wetting agent | Fisher Scientific |
| D-Mannitol | — | Matrix former | Acros Organics |

Example 6

The wet stirred media milling of fenofibrate was carried out in a recirculation mill MicroCer (Netzsch, Exton, Pa.) which was equipped with a pin rotor. The grinding chamber had a volume of 80 ml and is lined with zirconia. Both the grinding chamber and stirred vessel were connected to an external cooling device (M1-.25A-11HFX, Advantage, Greenwood, Ind.) to dissipate heat generated during the grinding process. The zirconia was stabilized with yttrium, which functions as a grinding media. The grinding media size was 400 μm and had a volume of 50 mL. The rotational speed of the stirrer was 3200 rpm (-11.4 m/s). The operating temperature was less than 35° C.

To prepare the milling suspensions, all of the matrix-forming materials were dissolved in the DI water before the API powder was added under intense shear mixing. The shear mixing was continued for 15 minutes to completely wet and homogenize the sample. Depending on the amount of foam formation, the sample was put into the refrigerator for a period of time to reduce the foam. Mannitol was added to the API suspension after milling and mixed for another 10 minutes in the media mill until completely dissolved.

The API nanoparticle size was measured with laser diffraction (LS 13 320, Coulter Beckman) after the sample was diluted with DI water at two time points: right after milling and after 2 days (2-d) resting of the suspension at room temperature.

TABLE 8

API nanoparticle size after wet stirred media milling

| FNB (w/v) | HPMC-E3 [wrt FNB] | SDS [wrt FNB] | Mannitol [wrt FNB] | Milling time | Particle size (after milling) d50 | d90 | Particle size (after 2 days-ambient) d50 | d90 |
|---|---|---|---|---|---|---|---|---|
| 30% | 5% | 0.75% | — | 6 min | 827 nm | 2524 nm | 891 nm | 2452 nm |
| 20% | 5% | 0.75% | — | 10 min | 497 nm | 1602 nm | N/A | N/A |
| 10% | 25% | 0.75% | — | 2 h | 157 nm | 235 nm | 158 nm | 326 nm |
| 10% | 10% | 0.75% | — | 2 h | 163 nm | 351 nm | 159 nm | 385 nm |
| 20% | 5% | 0.75% | — | 2 h | 163 nm | 352 nm | 186 nm | 423 nm |
| 20% | 5% PVP | 0.75% | — | 2 h | 263 nm | 745 nm | 754 nm | 1843 nm |
| 20% | 25% | 5% | — | 2.5 h | 163 nm | 260 nm | 268 nm | 645 nm |
| 20% | 5% | 0.75% | 50% | 2 h | 166 nm | 347 nm | 168 nm | 330 nm |
| 30% | 5% | 0.75% | 50% | 2 h | 171 nm | 382 nm | 171 nm | 369 nm |
| 30% | 10% | 0.75% | — | 2 h | 160 nm | 248 nm | 173 nm | 401 nm |

Example 7

This example demonstrates a method of identifying the appropriate matrix-forming materials and their concentrations. All precipitation experiments were performed at room temperature. FNB was dissolved in either acetone or Et-OH to form a clear solution. The matrix-forming materials were dissolved in DI water by stirring. The concentration of polymer or surfactant was varied between 10, 25, and 50% (w/w) with respect to FNB. The drug solution was added to the aqueous phase quickly during sonication. The duration of sonication was 1 minute including initial solvent addition time. After precipitation the suspension was stored at room temperature for 2 days. Those suspensions that settled after 2 days were discarded and suspensions which were still suspended were prepared for size analysis. Before sizing the suspensions were mixed for 1 minute in a vortex mixer or a magnetic stirrer. The size was measured in the laser diffraction size analyzer LS 13-320. The final drug concentration in the suspension was 0.32% (w/v).

Example 8

This example demonstrates the use of T-mixing to make the API nanosuspension. Some materials that were used for this and some following examples are listed in Table 9.

TABLE 9

Materials used for T-mixing

| Materials | Abbreviation | Function | Manufacturer |
|---|---|---|---|
| Fenofibrate | FNB | API | Jai Radhe Sales, Ahmedabad, India |
| De-ionized water | DI water | anti-solvent | — |
| Acetone | Ace | solvent | Sigma Aldrich |
| Ethanol | Et—OH | solvent | Sigma Aldrich |
| Hydroxypropyl methylcellulose E3 (Methocel E3 premium LV) | HPMC E3 | Polymeric stabilizer | Dow Chemicals |
| Hyroxypropyl cellulose SL | HPC-SL | Polymeric stabilizer | Nisso America Inc. |
| Sodium dodecyl sulfate | SDS | Surfactant stabilizer, wetting agent | Sigma Aldrich |
| Pluronic F-68 | P-68 | Polymeric surfactant stabilizer | Sigma Aldrich |
| Pluronic F-127 | P-127 | Polymeric surfactant stabilizer | Sigma Aldrich |
| Polysorbate-80 | Tween-80 | Non-ionic surfactant | Sigma Aldrich |
| Hexadecyltrimethyl-ammonium bromide | CTAB | Cationic Surfactant | Sigma Aldrich |
| Sodium Alginate (Food Grade) | Na-Alg | Anionic polysaccharide | N/A |

The T-mixer was made from a delrin cylinder with a 2-in ID (inner diameter) by 2-in in length. The delrin cylinder was purchased from McMaster Carr (Santa Fe Springs, Calif,). Two holes were drilled in the side of the cylinder to make inlets for the anti-solvent and solvent streams. Both inlets have a 0.0787-in OD (outer diameter). A T-mixer outlet of 0.1875-in OD was also drilled for the exit stream of the precipitated suspension. Another hole with a diameter of 0.5-in was drilled at the top of the T-mixer for the sonication probe. No specific sealing for the ultrasonic probe was used. The T-mixer opening was designed to fit the ultrasound probe in order to ensure optimum fluid—nozzle contact.

Figure 5:
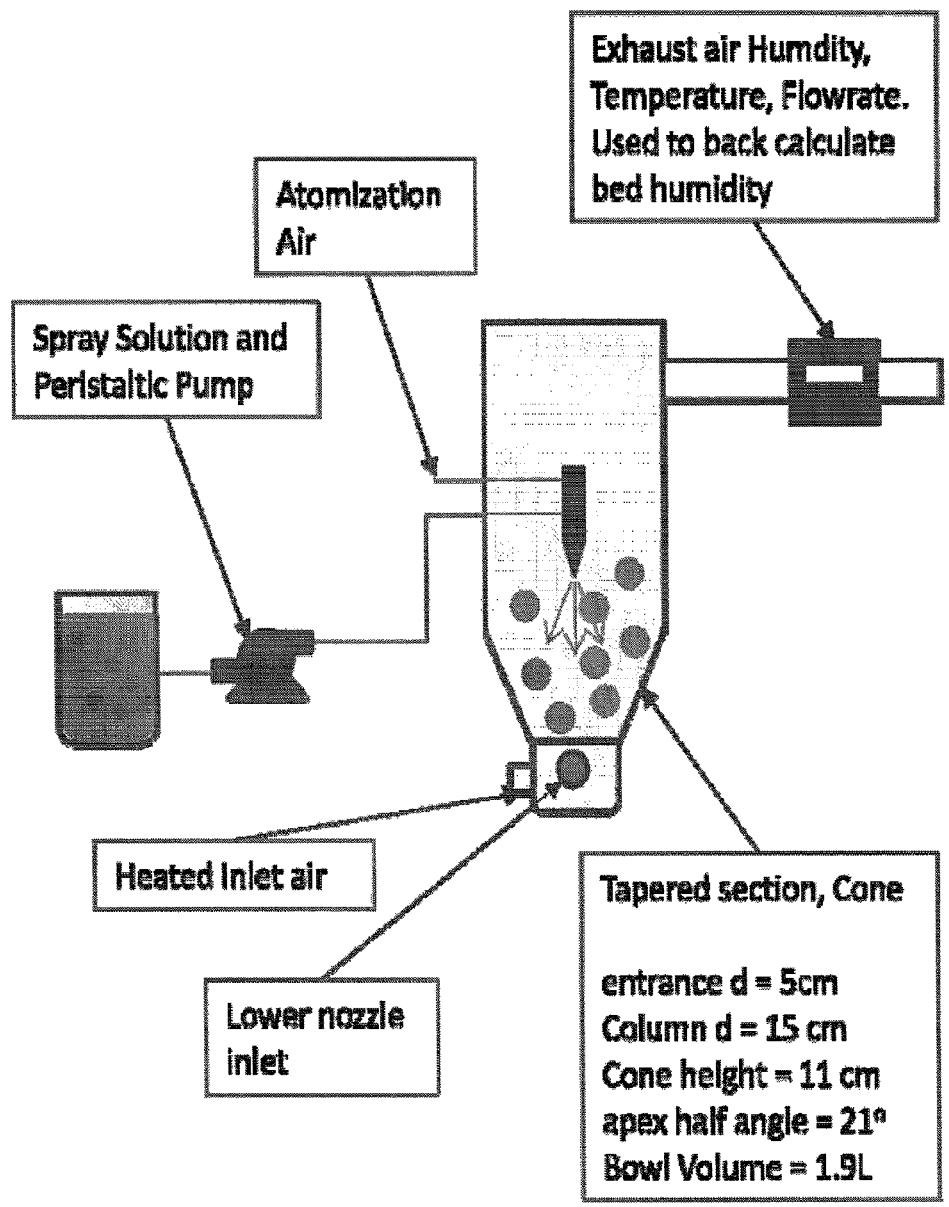
FIG. 5 depicts a fluid bed coating method that may be used in the present invention.

The organic and anti-solvent solutions were pumped at 16.5~17 and 55.1~52 ml/min into the T-mixer, respectively, using HPLC pumps (Laballiance Model CP). The flow directions are depicted in FIG. 5. The antisolvent temperature was maintained at 1° C. and the organic solution was at room temperature. According to literature it is found that a reduction in antisolvent temperature decreases the equilibrium solubility of the drug in solution which increases the amount of supersaturation. As the supersaturation increases, the nucleation rate increases, and the particle size decreases. The total batch size was 80 ml. Among the 80 ml of suspension 10 ml was solvent and 70 ml was antisolvent. Before the precipitation 20 ml of anti-solvent was put in the collection bath for quenching and the other 50 ml was pumped through the T-mixer. The collection chamber was kept in the sonication bath and the sonication was continued during the T-mixing experiment. After the precipitation the suspension was filtered with a 25 μm filter to remove the chunks that were observed during the precipitation. The suspension was stored at room temperature for 2 days and sized via laser diffraction. The final drug concentration in the suspension was 0.32% including the solid loss.

The FNB suspensions produced using the T-mixer can be divided into three groups; completely stable suspensions, medium stable suspensions and unstable suspensions. The completely stable suspensions do not show any increase in particle size after storage for 2 days at room temperature.

The medium stable suspensions show particle size growth of FNB within the first 10 minutes after formation. Unstable suspensions agglomerate immediately.

TABLE 10

| Completely stable API nanosuspension | | | | | | |
|---|---|---|---|---|---|---|
| Solvent & | After Formation | | | After 2 days (ambient temp.) | | |
| Formulation | d10 | d50 | d90 | d10 | d50 | d90 |
| Acetone; HPMC, 25% + SDS, 25% | 0.310 | 0.800 | 2.345 | 0.313 | 0.844 | 2.41 |
| Acetone; HPMC, 25% + P-68, 50% | 0.335 | 1.016 | 2.40 | 0.334 | 1.015 | 2.32 |
| EtOH; HPC-SL, 25% + Na-Alg, 50% | 0.335 | 1.206 | 3.36 | 0.344 | 1.273 | 3.97 |

TABLE 11

| Medium stable API nanosuspension | | | | | | | | | |
|---|---|---|---|---|---|---|---|---|---|
| Solvent & | After Formation | | | After 10 min | | | After 2 days (ambient temp.) | | |
| Formulation | D10 | D50 | D90 | D10 | D50 | D90 | D10 | D50 | D90 |
| Acetone; HPMC, 25% + Na-Alg, 50% | 0.495 | 1.61 | 3.85 | 1.50 | 2.53 | 5.0 | 1.48 | 2.54 | 5.33 |
| EtOH; HPC-SL, 25% + P-68, 10% | 0.199 | 0.393 | 2.73 | 0.310 | 3.407 | 6.70 | 0.274 | 3.08 | 5.52 |

Example 9

In this example, drug loading (FNB) in the suspension was varied from 0.32% (w/v) to 4% (w/v) in a T-mixing, in order to demonstrate the effects on suspension stability. The suspensions (at 10 minutes and 2 days after T-mixing) were centrifuged at 20,000 rpm for 0.5 hr or 10,000 rpm for 1 hr in the Sorvall RC28S centrifuge (Dupont Instruments-Sorvall Miami, Fla.) to remove the organic solvent from the suspension. A large volume of supernatant was discarded. The solids were resuspended by gentle mixing with a pipette in the remaining supernatant. In this way the concentration of the FNB was increased from 1%~4% to 10~27% (w/v).

The stability results for the suspensions are given in Table 12.

TABLE 12

| Drug loading and API nanosuspension stability | | | | | | | | |
|---|---|---|---|---|---|---|---|---|
| Drug | | | Total Solid | Solid loss | PSD t~10 m | | PSD t~2 d | |
| Loading | Polymer | Surfactant | content | % wrt TS | d50 | d90 | d50 | d90 |
| 0.32% | HPMC-25% | SDS-10% | 0.35 g | 3.73 | 1.275 | 2.60 | 1.28 | 2.83 |
| 1% | HPMC-25% | SDS-10% | 1.08 g | 18.24 | 0.803 | 3.558 | 1.089 | 5.145 |
| 0.32% | HPMC-25% | P-68-50% | 0.35 g | 1.14 | 0.457 | 1.855 | 0.445 | 1.705 |
| 1% | HPMC-25% | P-68-50% | 1.4 g | 6.50 | 1.192 | 3.015 | 1.211 | 3.299 |
| 2% | HPMC-25% | P-68-50% | 2.8 g | 5.07 | 0.669 | 1.833 | 0.640 | 1.826 |
| 4% | HPMC-25% | P-68-50% | 5.6 g | 9.66 | 2.403 | 10.07 | 2.511 | 10.84 |

Several interesting observations were made from this example. Drug loadings up to 4% can be produced in the T-mixer using HPMC and P-68 as matrix-forming materials and acetone as solvent. However, an increase in drug loading results in an increase in API nanoparticle size because more concentrated suspensions are more difficult to stabilize (higher collision frequency). In addition, higher drug loadings need a higher concentration of matrix-forming materials, which leads to an increase in viscosity of the anti-solvent. The drug loading can be increased up to 27% by centrifugation and resuspension without any significant change in particle size.

Example 10

In this example, a melt emulsification process was used to produce the suspension. The melt emulsification process is shown in FIG. 4 and involved the following steps:

1) The micronized drug particles and the stabilizer are dispersed in water and the suspension is heated to temperatures above the melting point of the drug. To ensure complete melting and to reduce the viscosity of the melt, temperatures at least 10° C. above the melting point of the drug were used. Gentle stirring with a magnetic stirrer was used during the heating process.

2) Emulsification was carried out with an ultrasonic probe (Vibra Cell VC 750, Sonics & Materials, Inc., Newtown, Conn.) for different times and at different intensities. During the emulsification step the samples were kept at elevated temperatures (10-15° C.+Tm) to avoid solidification of the melt.

3) Rapid cooling of the hot emulsion in an 4° C. thermostatic bath (NESLAB TRE 10, Thermo Electron Corporation, Newington, NH) to temperatures below 10° C. leads to a solidification of the drug particles. The final result is a FNB nanosuspension. After cooling, the particle size distribution was measured via laser diffraction (LS-13320, Coulter Beckman). This example uses a suspension volume of 50 ml and the sonication amplitude is at 100% (~95 W).

TABLE 13

| Materials used for melt emulsification | | | |
|---|---|---|---|
| Used Stabilizers | Abbreviation | Function | Manufacturer |
| Pluronic F-68 | P68 | polymeric surfactant | Sigma Aldrich |
| Pluronic F-127 | P127 | polymeric surfactant | Sigma Aldrich |
| Polysorbate-80 | Tween 80 | non-ionic surfactant | Sigma Aldrich |
| Polyvinyl alcohol | PVA | polymer | Sigma Aldrich |
| Polyvinyl pyrrolidone K30 | PVP-K30 | polymer | Sigma Aldrich |
| Polyvinyl pyrrolidone K360 | PVP-K360 | polymer | Sigma Aldrich |

Different stabilizers and stabilizer concentrations were investigated and evaluated based on the particle sizes after the formation. Stabilization against droplet coalescence and particle agglomeration needed to obtain drug particles in the desired size range. The API nanoparticle size is shown in FIG. 9.

Figure 10:
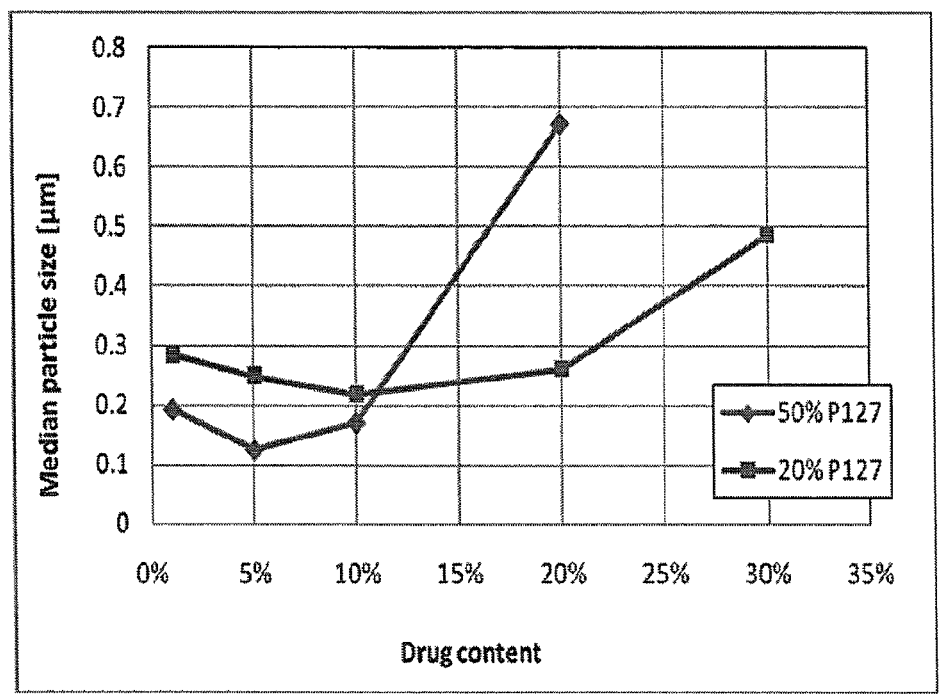
FIG. 10 shows the median particle size of fenofribrate nanoparticles in the nanosuspenion as a function of drug loading used to emulsifying fenofibrate in accordance with Example 10.

When the drug loading of the suspension was increased its effect on the median particle size is presented in FIG. 10, as measured when surfactant P-127 was present.

Example 11

In this example, fluid bed coating (FCB) was used to coat the carrier particles with an API nanosuspension. The apparatus for this example was a MiniGlatt 9550 with a top spray nozzle. The atomization pressure was 0.8-1.0 bar. The flow rate was 1.4-1.6 cfm for PS; 0.8-1.2 cfm for CS and GranuLac 200; and 3.4-3.6 cfm for Pharmatose. The spray rate was 0.25-1.5 ml/min The inlet temperature was kept at 68° C. The maximum bed humidity's were <40% for PS/CS; and <25% for lactose. The bed mass used was 150 g.

Example 12

In this example, a certain amount of mannitol (50% with respect to FNB) and SDS (5% with respect to FNB) was added to the API nanosuspension before fluid bed coating. To enhance the stability of the API nanosuspension, the milling procedure was carried out at low SDS concentrations (0.75% SDS with respect to FNB). Just before placing the API nanosuspension into the FBC, the other, larger portion of the SDS and mannitol were added to the API nanosuspension. The API nanosuspension was homogenized under shear mixing until both excipients were completely dissolved in the dispersion medium.

Figure 36:
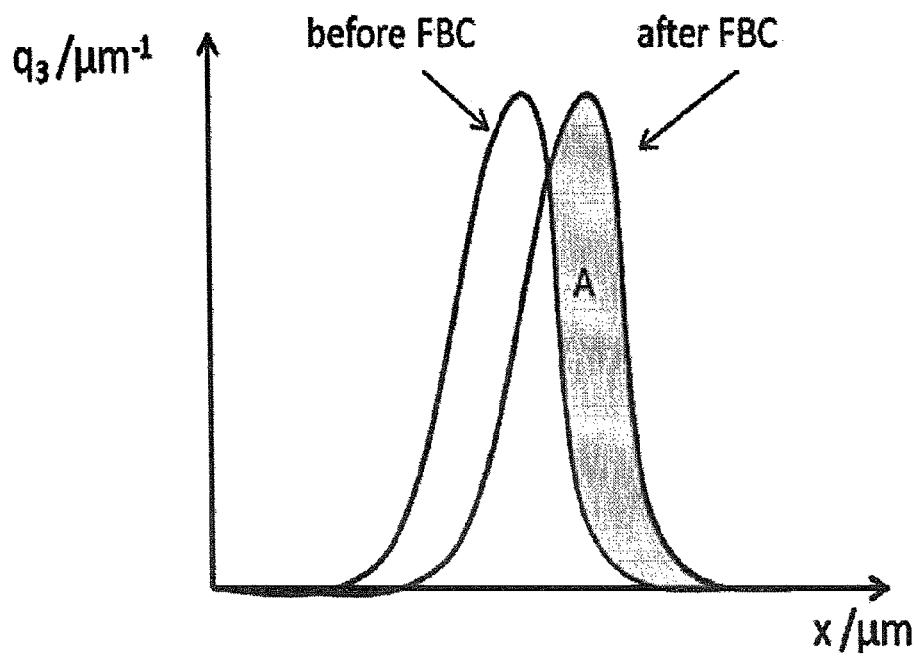
FIG. 36 shows size distribution curves of carrier particles before and after fluid bed coating used to determine the agglomeration ratio.

The dry-coated carrier particles, during fluid bed coating, may agglomerate. The present invention uses agglomeration ratio (AR) to quantify the degree of agglomeration of carrier particles during fluid bed coating (FBC). It is defined as the area under the particle size distribution curve of fluid-bed-coated particles after subtracting the area that falls under the particle size distribution curve of the same particles as measured prior to the fluid bed coating step. The agglomeration ratio may, for example, be represented by the area A in FIG. 36.

The results of using such API nanosuspensions are given in Table 14. The references used in later examples are given in the leftmost column of the Table 14.

TABLE 14

| Fluid bed coating using API nanosuspension with added SDS/mannitol | | | | | | | | |
|---|---|---|---|---|---|---|---|---|
| | Fluid bed suspensions | | | | | | | |
| Exp. | FNB | HPMC | SDS | Mannitol | ~d50 | AR | Assay | Comments |
| PS-70 | 20% | 5% | 0.75% | — | 165 nm | 5.7% | 13.5% | used for 1$^{st}$ animal study |
| PS-72 | 20% | 5% | 0.75% | 50% | 165 nm | 83% | 11.9% | with mannitol |
| PS-74 | 10% | — | 20% P-68 | — | 740 nm | 62% | 8.2% | from melt emulsification |
| PS-75 | 20% | 5% | 0.75% | — | 165 nm | 37% | 13.1% | same as PS-70 |
| PS-76 | 20% | 5% | 0.75% | — | 500 nm | 6% | 13.5% | larger particle sizes |
| PS-77 | 30% | 5% | 0.75% | — | 830 nm | 9.8% | 17.6% | larger particle sizes |
| PS-80 | 20% | 5% | 0.75% | — | 165 nm | 50.9% | 13% | higher humidities (up to ~67%) |
| PS-82 | 20% | 5% PVP | 0.75% | — | ~300 nm | 5.3% | 14.5% | with PVP as polymer |
| CS-83 | 20% | 5% | 0.75% | — | 165 nm | 63.3% | 29.6% | highest drug loading |
| CS-84 | 20% | 5% | 0.75% | 50% | 165 nm | 39.2% | 11.2% | |
| L-85 | 20% | 5% | 0.75% | 50% | 165 nm | 22.7% | 15.6% | dry-coated with R972P |
| L-86 | 20% | 5% | 0.75% | 50% | 165 nm | 28.4% | 13.3% | |
| L-87 | 30% | 5% | 0.75% | 50% | 170 nm | 26.9% | 14.3% | |
| L-88 | 20% | 25% | 5% | — | ~200 nm | 37% | 15.3% | complete redispersion |
| L-89 | 30% | 10% | 5% | 50% | 165 nm | 25.6% | 14.2% | complete redispersion, fast dissolution |
| L-91 | 30% | 10% | 5% | 50% | 170 nm | 31.8% | 14.7% | Larger carrier particles* |
| L-92 | ~10% | 25% | 50% P-68 | — | ~1.1 μm | 12.4% | 5.8% | Suspension from LASP with P-68 |

TABLE 14-continued

Fluid bed coating using API nanosuspension with added SDS/mannitol

| Exp. | Fluid bed suspensions | | | | ~d50 | AR | Assay | Comments |
| --- | --- | --- | --- | --- | --- | --- | --- | --- |
| | FNB | HPMC | SDS | Mannitol | | | | |
| L-93 | 30% | 10% | 5% | — | 210 nm | 24.5% | 15.6% | |
| L-94 | 14.8% | 20% | 8% | 50% | ~3 µm | 7.2% | 11.6% | Suspension from LASP with SDS |

*For L-91 a larger carrier particle size was used. The size distribution of the initial carrier material (pharmatose) is given in FIG. 27. The particles were fluidized without dry-coating.

Figure 11:
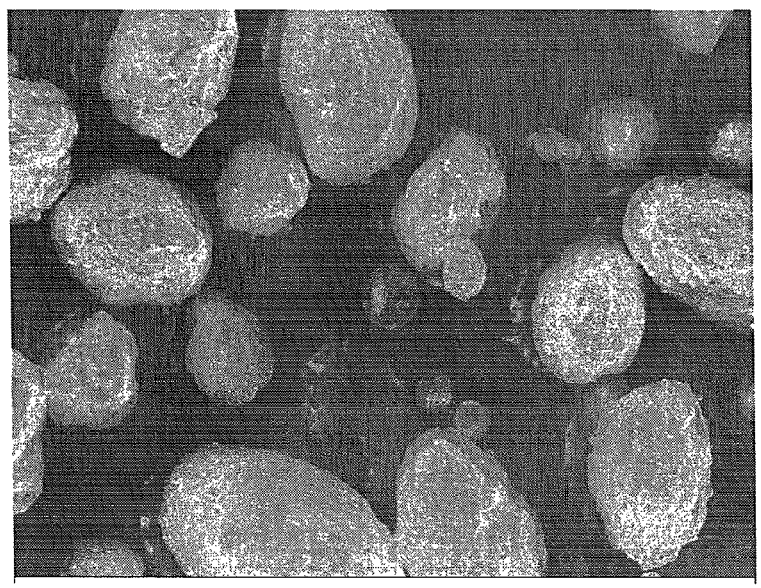
FIG. 11 shows a SEM image of composite particles of potato starch, PS-70 as prepared in accordance with Example 12.
Figure 12A:
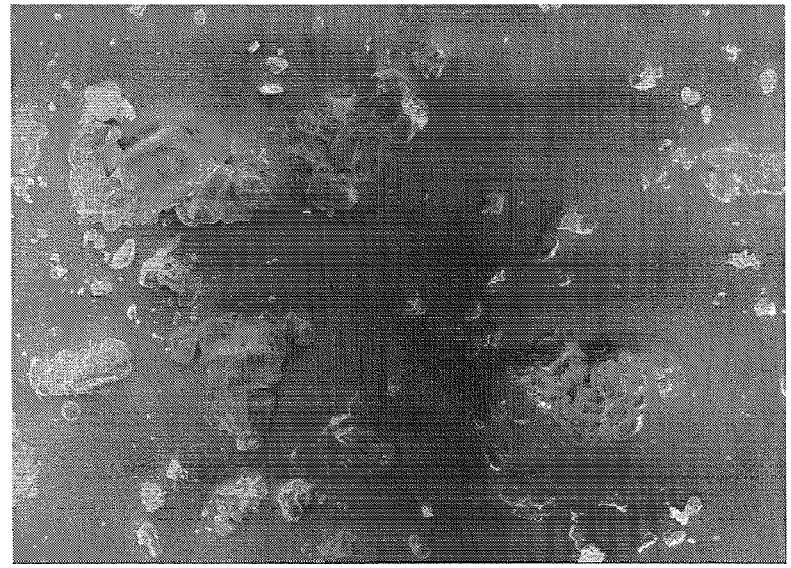
FIGS. 12A-12B show SEM images of composite particles of lactose, L-89 as prepared in accordance with Example 12.
Figure 12B:
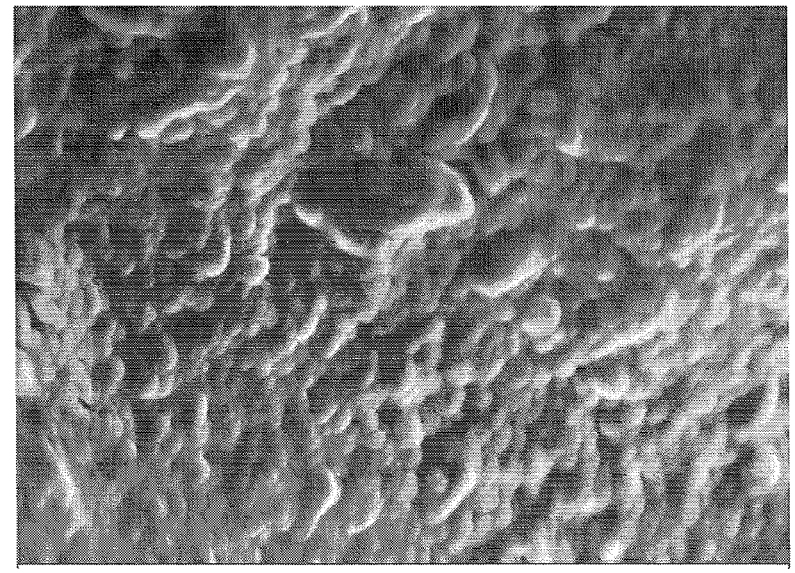

SEM images of two different composite powders are given in FIGS. 11 and 12A-12B. In FIG. 11, coated potato starch (PS) particles are shown. The surface of the PS was covered with a layer of API particles embedded in a polymer matrix. The PS particles were available as individual particles, which is in good agreement with the measured agglomeration ratio of only 5.7%. In addition to the PS particles, some finer spherical spray-dried particles can be seen in the sample.

In FIGS. 12A-12B, the coated lactose particles are presented. In FIG. 12A an overview of the morphology of the sample is given. The wide size distribution and the irregular shape of the lactose are clearly visible. Also agglomerates of the carrier particles can be found in the sample. FIG. 12B is a closer view of the lactose surface after fluidized bed coating. A homogeneous coating layer consisting of nano-sized FNB particles surrounds the lactose particle. The size of the FNB particles is in good agreement of the measured sizes in the nanosuspension, confirming that no significant growth of the particles during spraying in the fluid bed occurred.

Example 13

Figure 13:
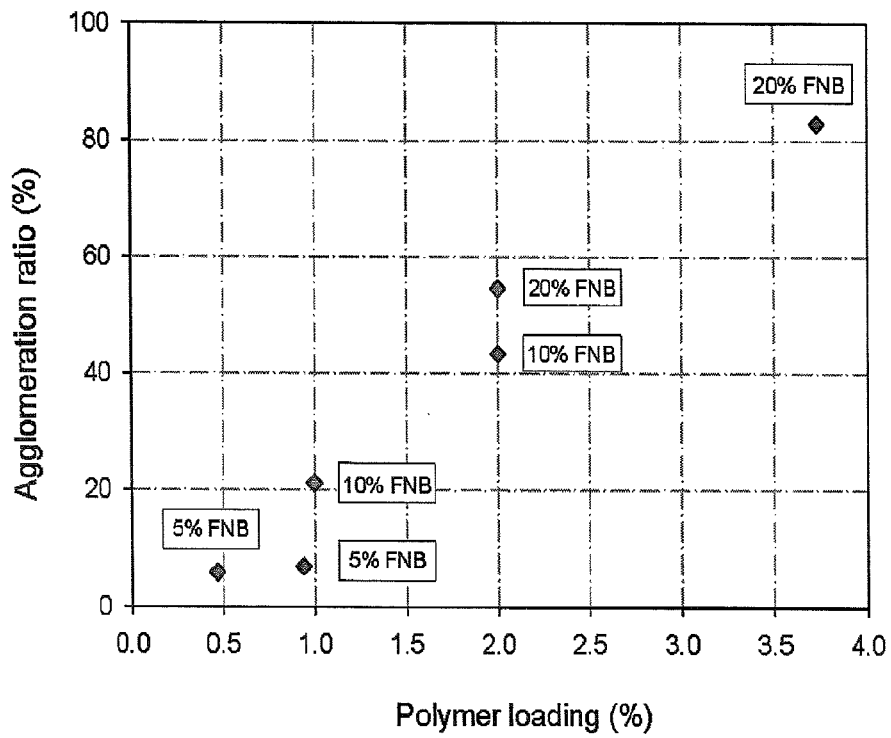
FIG. 13 is a plot of the relationship between agglomeration ratio and matrix-forming polymer loading for composite particles as prepared in accordance with Example 13.

In this example, the effects of polymer loading on fluid bed coating (FBC) were demonstrated. During FBC, agglomeration of the carrier particles can occur. In FIG. 13, the agglomeration ratio as a function of polymer loading (here HPMC from the milling suspension) is given. Even without agglomeration of the carrier particles, a minimal agglomeration ratio of approximately 5% exists, which is caused by a loss of fine particles through the filter of the FBC apparatus thereby shifting the size distribution to larger sizes.

Above a limiting polymer loading, agglomeration of the carrier particles occurs. It seems that there exists a linear dependency between agglomeration ratio and polymer loading as long as the API nanosuspension has the same concentration.

Example 14

In this example, the stability of API nanosuspension after long-term storage was tested. The API nanosuspension samples were stored under refrigerated conditions (~8° C.). Only gentle mixing with a pipette was carried out to homogenize the samples before sizing. The particle size changes are listed in Table 15.

TABLE 15

API nanosuspension long-term stability

| Formulation | Particle size before storage time | | Storage time | Particle size after storage time | |
| --- | --- | --- | --- | --- | --- |
| | d50 | d90 | | d50 | d90 |
| 20% FNB, 5% HPMC, 0.75% SDS, 50% Mannitol | 166 nm | 398 nm | 8 weeks | 165 nm | 364 nm |
| 30% FNB, 10% HPMC, 0.75% SDS | 160 nm | 248 nm | 4 weeks | 196 nm | 472 nm |

Example 15

Figure 14:
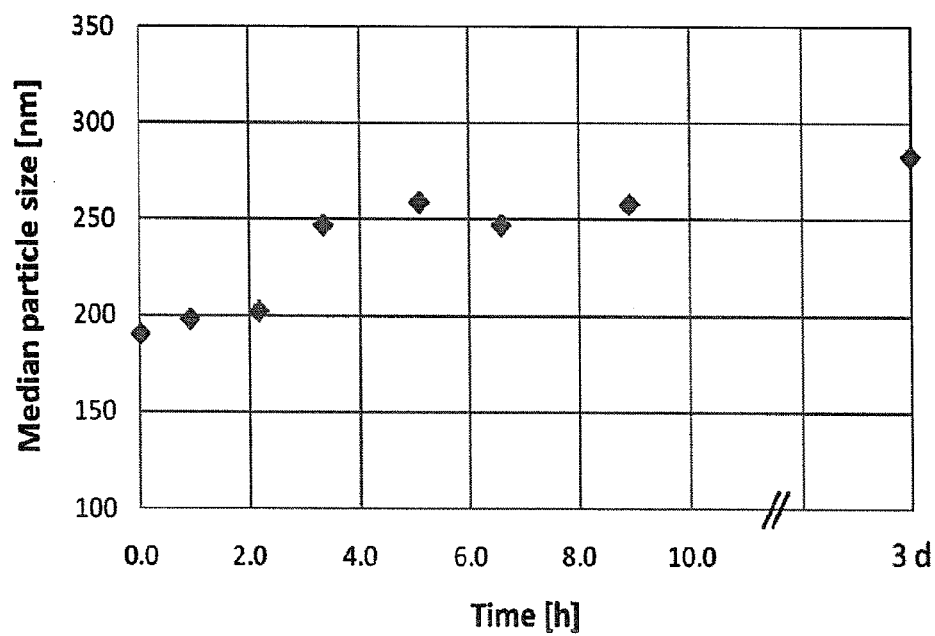
FIG. 14 shows the evolution of median particle size of fenofibrate nanoparticles over time after addition of sodium dodecyl sulfate (SDS) before fluid bed coating to a nanosuspension of the particles in preparing the fenofibrate nanosuspension in accordance with Example 15.

In this example, the stability of the API nanosuspension after addition of mannitol and SDS was tested. The API nanosuspension, after milling, has 30% FNB, 10% HPMC, and 0.75% SDS. Right after milling, 4.25% SDS and 50% mannitol were added to the API nanosuspension. As shown in FIG. 14, the particle size had slight growth, probably due to the SDS content causing the solubility of FNB to increase, which facilitates Ostwald ripening and subsequent particle size growth.

Example 16

Figure 15:
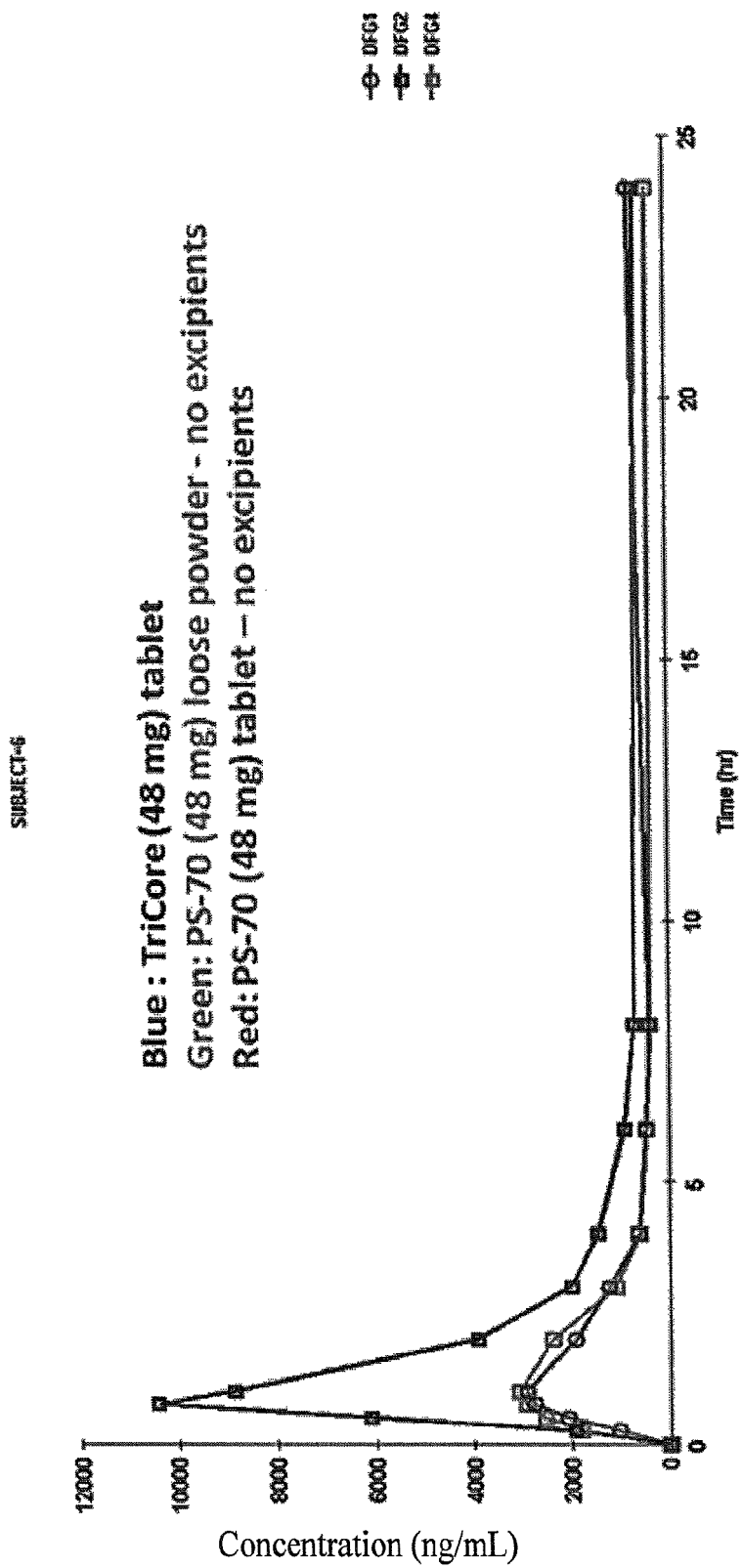
FIG. 15 shows blood plasma concentration of the API in animals as a function of time for three different delivery systems used to deliver the drug to animals in accordance with Example 16.

An animal study with dogs was carried out with formulation PS-70 (loose powder and compressed tablets). The tablets of formulation PS-70 were made using the Catalent press ENTERPAC, Model: MTCM-1 with the tools NATOLI-12-02-3750 (standard concave). The tablets have a diameter of 0.375 inch. The press was set to 2500 psi for about 2 seconds to compress the composite powder into a tablet. The tablet mass was 355 mg, which equals a FNB content of 48 mg. In FIG. 15, the evolution of FNB plasma concentration in one of the 6 dogs is presented. The three arms of this study were: 1.) TriCore tablet (48 mg, a commercial fenofibrate tablet), 2.) PS-70 tablet, 3.) PS-70 loose powder. The observed trend is similar in all dogs.

The TriCore tablet shows a 6 times higher bioavailability than micronized FNB, the formulation PS-70 shows only twice the bioavailability, which is also less dependent on the dosage form (tablet or loose powder).

Example 17

The quick release of API from the API composite particles was shown in a dissolution test. The dissolution test was carried out using a Distek 2100 C series, USP II (paddle method). The conditions of the dissolution test were: background medium is 25 mM SDS solution; vessel volume was 900 mL; temperature was 37° C.; paddle speed varied from 0 to 100 rpm; sample size was ~48 mg; sink conditions always fulfilled (solubilityFNB/cFNB>3). The samples during and after the dissolution tests were taken by manual sampling with a syringe and immediate filtering of the samples was carried out (filter size 0.45 μm). The drug content in the sample was determined by a spectrophotometer at a wavelength of 290 nm. This dissolution test procedure was also used for Examples 18-26

Some abbreviations used in this and other examples: PS—Potato starch, Bi:—Corn starch, L—Lactose, LP—loose powder, T—tablet.

Figure 16:
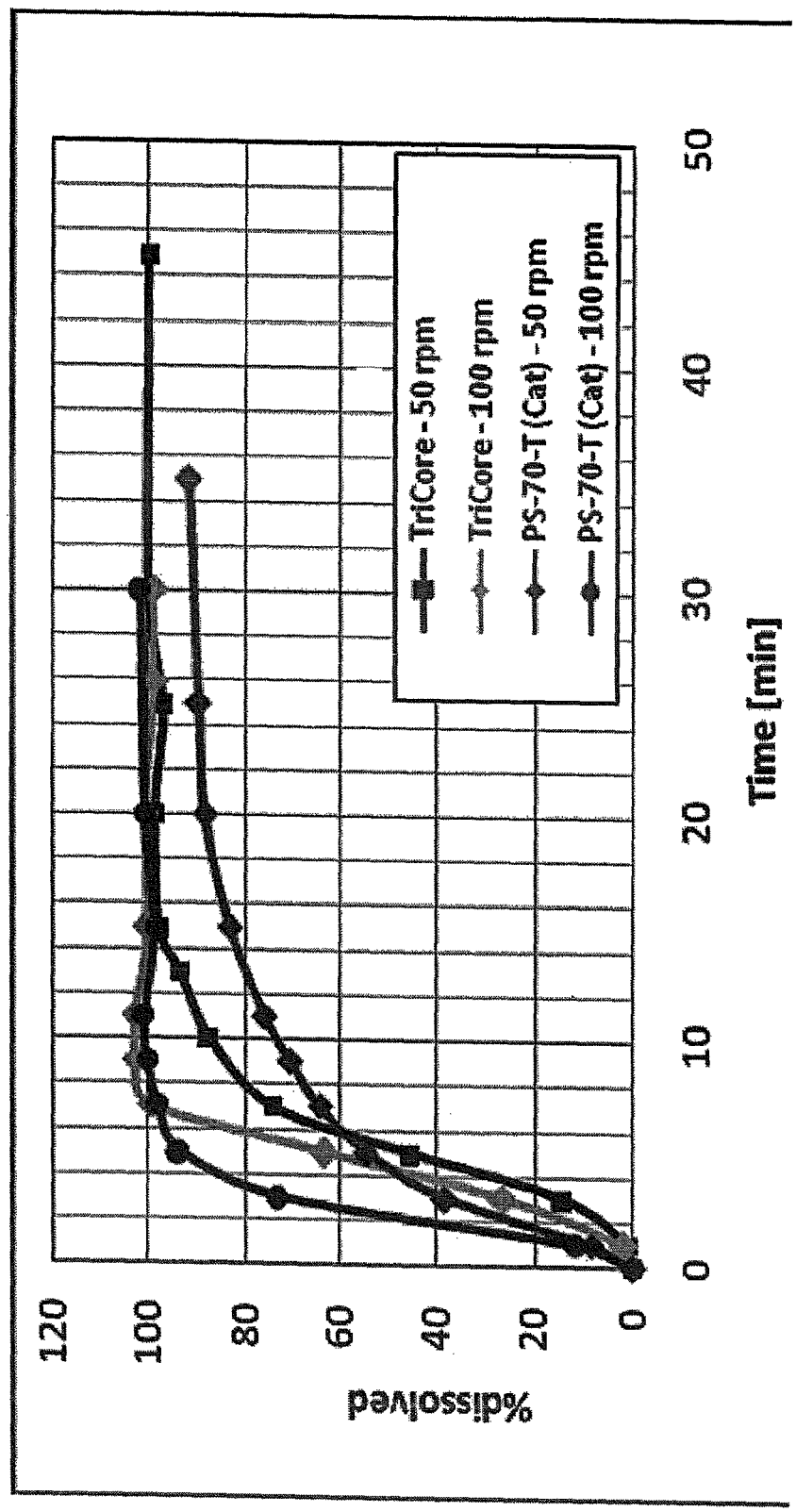
FIG. 16 is a plot of dissolution profiles of commercial fenofibrate TriCore tablets and PS-70 composite tablets at different paddle speeds in a dissolution test in accordance with Example 17.

The API composite particle with potato starch as carrier showed a dissolution profile as depicted in FIG. 16. The PS-70-T shows fast dissolution at higher paddle speeds (100 rpm), but a poor performance at 50 rpm.

Example 18

Figure 17:
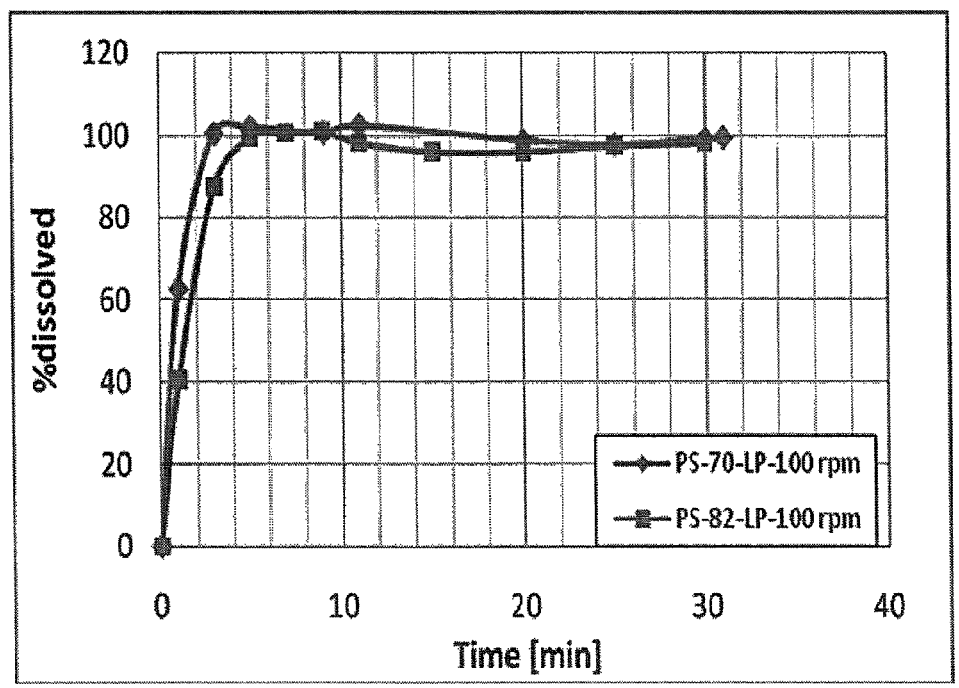
FIG. 17 shows the influence of two different matrix-forming polymers in the composite particles on the dissolution profiles of the composite particles in a dissolution test in accordance with Example 18.

This example demonstrates the effects of coating polymer on the dissolution test. As shown in FIG. 17. The dissolution rate of the composite powder containing PVP is slightly slower than the one with HPMC. The reason for this is that the nanoparticles in the milling suspension were not as well stabilized as compared to the HPMC formulation. As a consequence, agglomeration of the FNB particles occurred and slowed down the dissolution rate.

Example 19

This example demonstrates the effects of the size of the API nanoparticles on tablet dissolution. Tablets were compressed from different FNB composite powders containing FNB nanoparticles of different sizes. The tablet compression pressure was 108 MPa with a dwell time of 3 minutes. The tablet diameter was ½ inch with a mass of ~220 mg. The paddle speed in the dissolution experiment was set to 100 rpm to exclude the caking effect.

Figure 18:
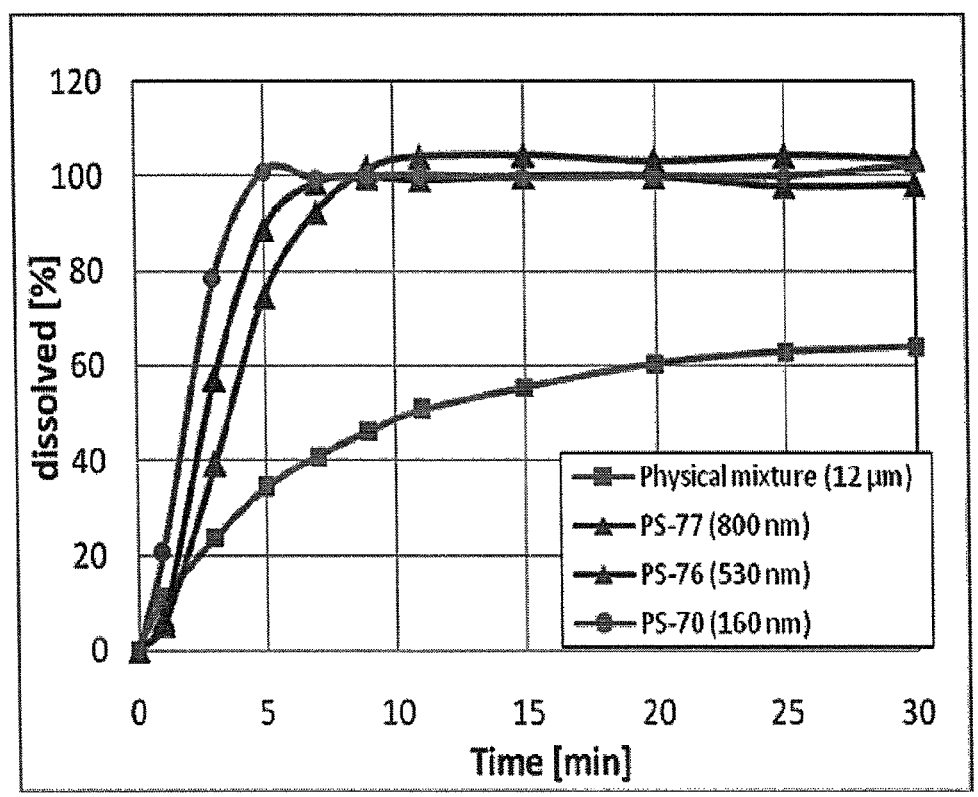
FIG. 18 shows the influence of size on the dissolution profiles of tablets in a dissolution test in accordance with Example 19

The dissolution results are shown in FIG. 18. The smaller API nanoparticle sizes led to faster dissolution.

Example 20

This example compares the dissolution profiles of Griseofulvin (GF) and Ibuprofen (Ibu) composite particles. The procedure of the present invention was used to generate the GF composite particles and Ibu composite particles. More specifically, the GF composite particles were made using the following conditions: a GF nanosuspension contained 20% GF, 5% HPMC, and 0.75% SDS. The milling time was 1 hour, which resulted in nanoparticles with d50=219 nm and d90=460 nm The carrier particles were potato starch dry coated with M5P. The agglomeration ratio of the API nanoparticles was 8%. The dissolution medium was 18.7 mM SDS solution.

The Ibu composite particles were made using the following conditions: the Ibu nanosuspension contained 20% GF, 5% HPMC, and 0.75% SDS. The milling time was 2 hours, which resulted in nanoparticles with d50=303 nm and d90=484 nm The carrier particles were potato starch dry coated with M5P. The agglomeration ratio of the API nanoparticles was 10.2%. The dissolution medium was phosphate buffer solution with pH 7.2

Figure 19:
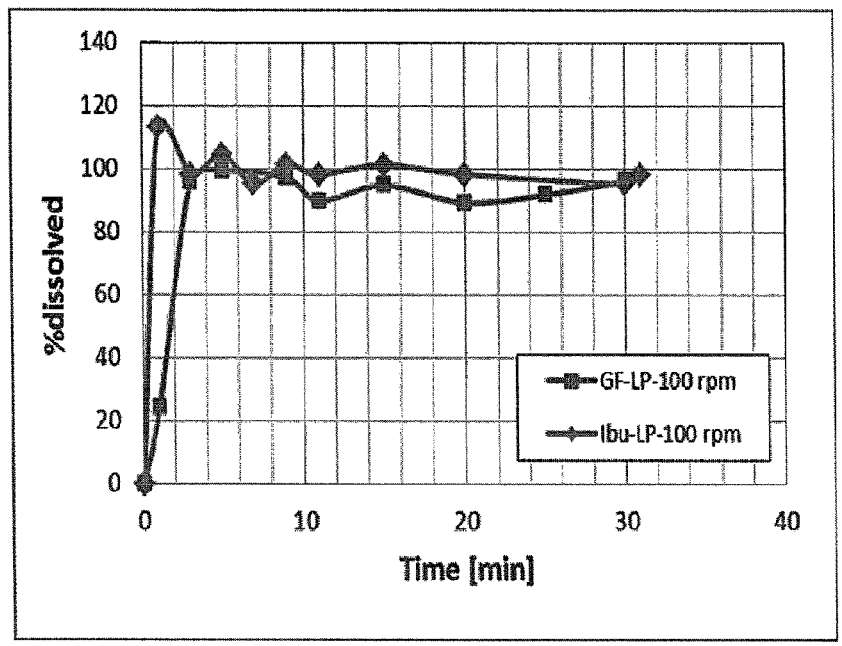
FIG. 19 is a plot of dissolution profiles of Griseofulvin and Ibuprofen-containing composite particles in a dissolution test in accordance with Example 20.

For both cases, the paddle speed was 100 rpm and the powder mass was ~220 mg. The dissolution profiles are shown in FIG. 19, where the dissolution curves are normalized to 100%.

Example 21

Figure 20:
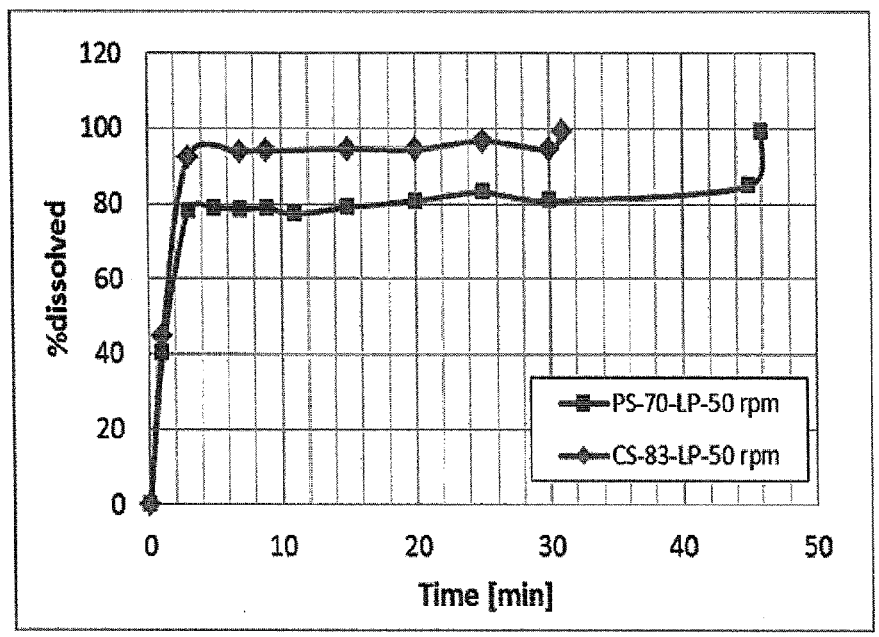
FIG. 20 shows the influence of carrier particles and their cake formation on dissolution profiles of the composite particles in a dissolution test in accordance with Example 21.

This example compares the dissolution profiles of FNB composite particles using PS or CS as the carrier particles. The paddle speed was 50 rpm. The dissolution profiles are in FIG. 20. The API composite particles with corn starch have a larger amount of the nanoparticles dispersed in the dissolution vessel. This is due to smaller particle size as well as lower density of CS compared to PS, which reduces the effect of gravity on the particles. As a consequence, the cake was much smaller and the effect of "trapping" the drug is reduced, but not completely eliminated.

Example 22

Figure 21:
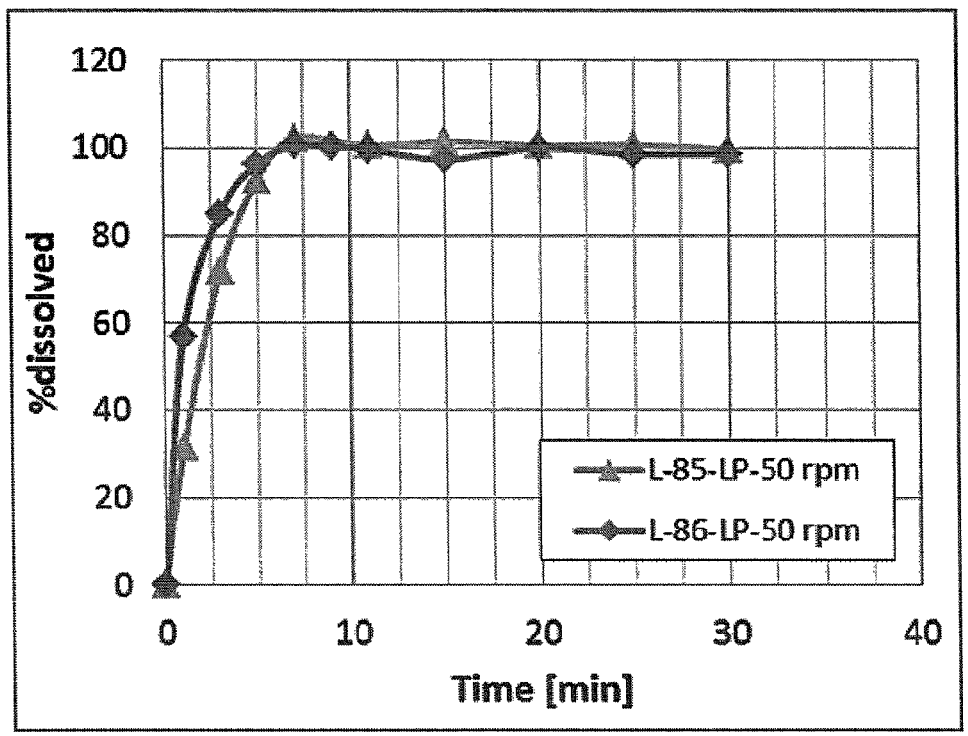
FIG. 21 shows the influence two different dry-coating materials in the composite particles on dissolution profiles of the composite particles in a dissolution test in accordance with Example 22.

This example compares the dissolution profiles of FNB composite particles using different dry coating materials: M5P (1.2%, hydrophilic, L-86) and R972P (1.85% hydrophobic, L-85). The paddle speed was 50 rpm. The dissolution profiles are given in FIG. 21. The nature of the dry coating material did not significantly affect the dissolution profiles. Although lactose dissolved much slower when coated with hydrophobic silica, the outer API-polymer-layer was not affected and showed similar dissolution behavior to the other dry-coating materials.

Example 23

Figure 22:
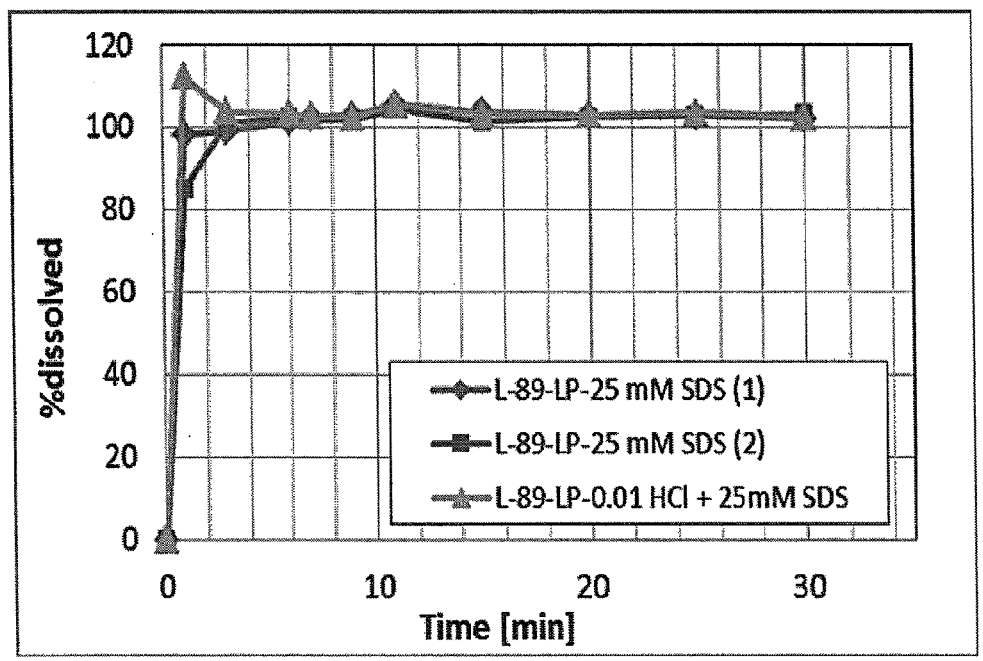
FIG. 22 shows the influence of background medium on dissolution profiles of the composite particles in a dissolution test in accordance with Example 23.

This example compares the dissolution profiles of FNB composite particles using different dissolution media: 25 mM SDS solution and 0.01 M HCl solution (pH~2) with 25 mM SDS. The dissolution profiles are given in FIG. 22. The reduction of the pH value did not affect dissolution behavior. This result was expected since FNB is a non-ionic compound. The first sampling point after 1 minute fluctuated because the powder in not yet homogeneously distributed in the dissolution vessel.

Example 24

Figure 23:
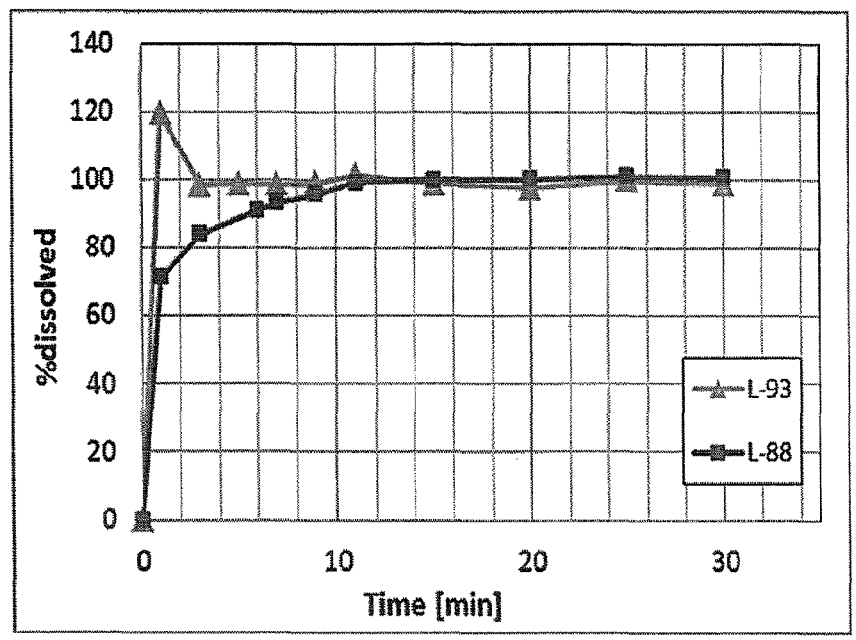
FIG. 23 shows the influence of polymer loading in the composite particles on dissolution profiles of the composite particles in a dissolution test in accordance with Example 24.

This example compares the dissolution profiles of FNB composite particles using different concentrations of polymer as the matrix-forming material: 10% and 25% HPMC. Here the FNB composite particles L-88 used a sprayed suspension: 25% HPMC, 5% SDS; and the FNB composite particles L-93 used a sprayed suspension: 10% HPMC, 5% SDS. The dissolution profiles are given in FIG. 23. Higher polymer loadings slowed down the dissolution rate. Longer times were required to dissolve the thicker polymer film and release the API nanoparticles.

Example 25

Figure 24:
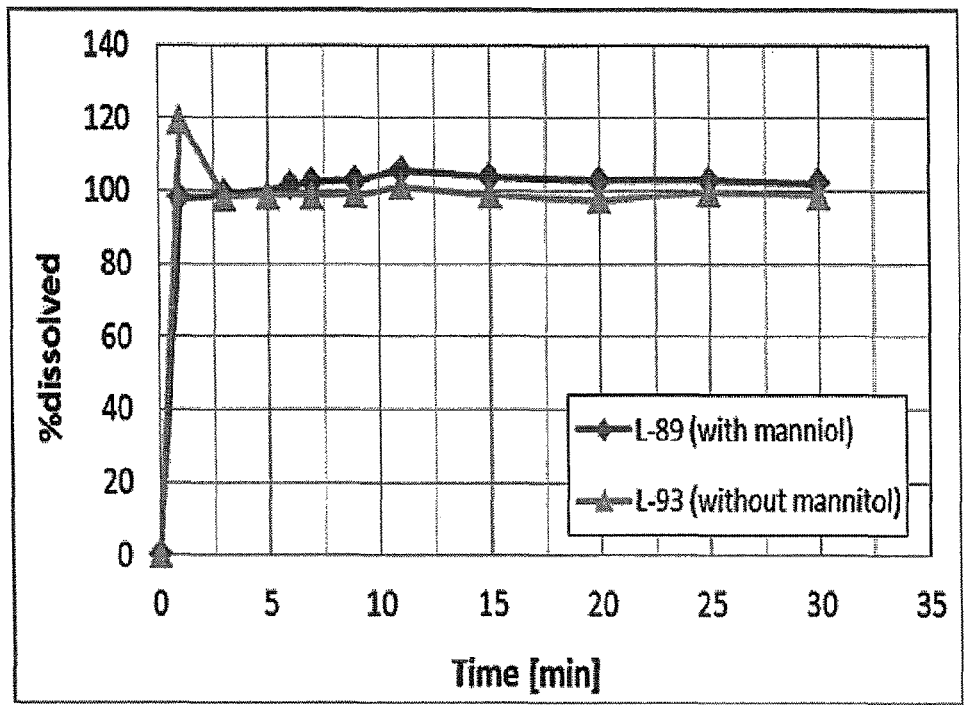
FIG. 24 shows the influence of mannitol addition to the composite particle making process on dissolution profiles of the composite particles in a dissolution test in accordance with Example 25.

This example demonstrates the influence of mannitol on dissolution profiles of FNB composite particles. The dissolution profiles are given in FIG. 24. The dissolution profiles are similar with or without mannitol. However, this may be because the formulation without mannitol (L-93) already shows instantaneous dissolution because of its high SDS content (5%) and low polymer content (10%).

Example 26

Figure 25:
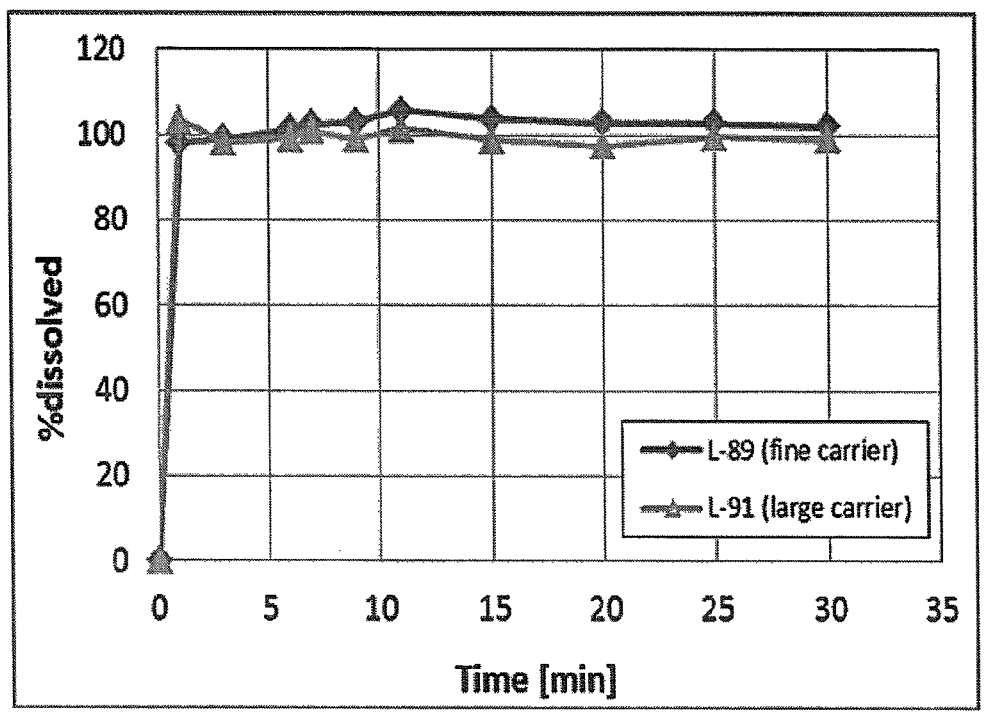
FIG. 25 shows the influence of carrier particle size on dissolution profiles of the composite particles in a dissolution test in accordance with Example 26.

This example demonstrates the influence of carrier particle size on dissolution profiles of FNB composite particles. The two types of carrier particles are: Pharmatose: d10=43.7 μm, d50=112.0 μm, d90=198.1 μm; and GranuLac 200:

d10=4.2 µm, d50=28.9 µm, d90=99.3 µm. The dissolution profiles are shown in FIG. 25. The dissolution profiles are similar between large and fine carrier particles. However, API composite particles with fine carrier particle sizes show a better performance for redispersion.

Example 27

Figure 26:
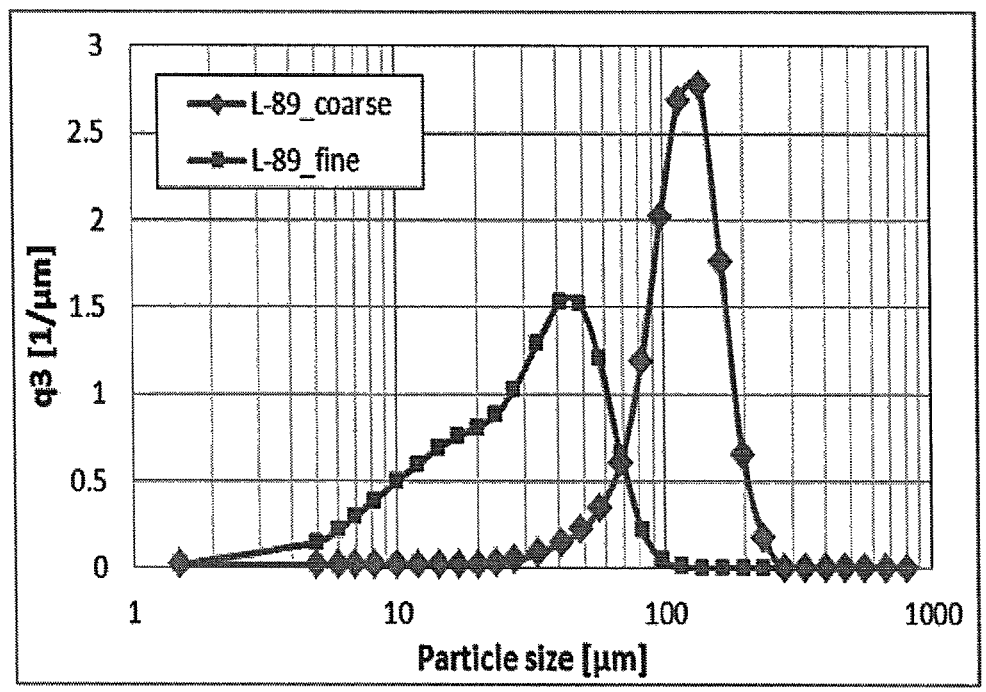
FIG. 26 shows particle size distributions of coarse and fine fractions of the L-89 composite particles determined by sieving in accordance with Example 27.
Figure 27:
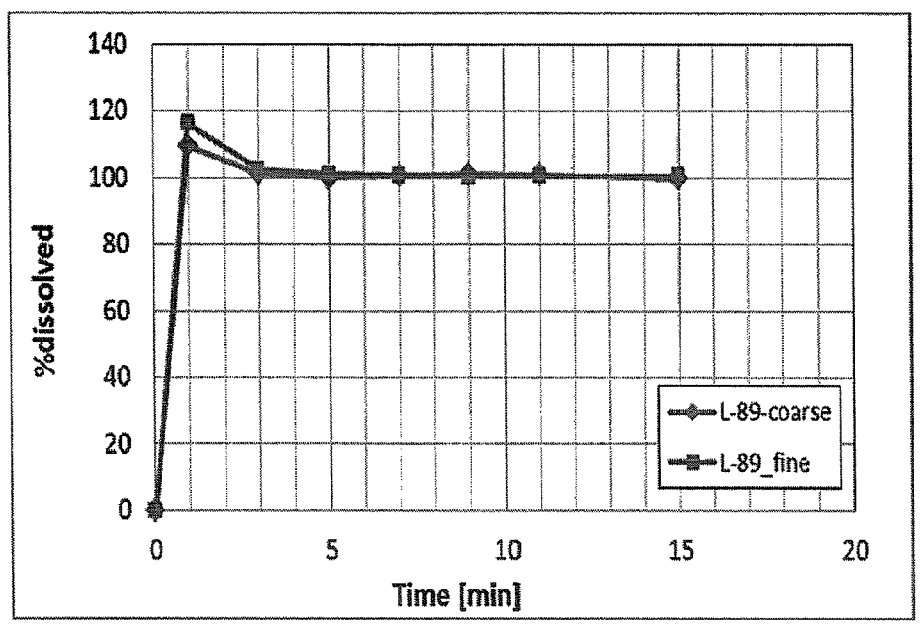
FIG. 27 shows dissolution profiles of the coarse and fine fractions of the L-89 composite particles in a dissolution test in accordance with Example 27.

This example demonstrates the homogeneity of the API composite particles (L-89). The L-89 composite particles were separated into two fractions: fine fraction: x<45 µm; coarse fraction: x>90 µm. The particle size distribution of the fine and coarse L-89 composite particles is shown in FIG. 26. The fine fraction had a distribution of: x10=9.2 µm, x50=30.9 µm, x90=59.7 µm. The coarse fraction had a distribution of x10=63.5 µm, x50=117.3 µm, x90=172.1 µm. The dissolution profiles of both the fine and coarse fractions are shown in FIG. 27.

Example 28

This example demonstrates the redispersion behavior of the API nanoparticles from the API composite particles. The carrier particles used in this example were lactose-based, because they are water soluble. 100 mg of API composite particles were dispersed in 8 ml of DI water. The vial was gently stirred by hand-shaking for 30 seconds. The vial was then rested for 2 minutes. The size of the particles was measured by laser diffraction. The dispersion results are shown in Table 16.

TABLE 16

Dispersion of API composite particles

| Sample No. | Sprayed formulation [wrt FNB] | | | Comment | Complete redispersion, yes or no? |
|---|---|---|---|---|---|
| | HPMC | SDS | Mannitol | | |
| PS-70 | 5% | 0.75% | — | | no |
| L-87 | 5% | 0.75% | 50% | | no |
| L-88 | 25% | 5% | — | | yes |
| L-89 | 10% | 5% | 50% | | yes |
| L-91 | 10% | 5% | 50% | Large carrier particles | no |
| L-92 | 25% | 50% P-68 | — | From LASP | no |
| L-93 | 10% | 5% | — | | no |
| L-94 | 20% | 8% | 50% | From LASP | yes |

Figure 28:
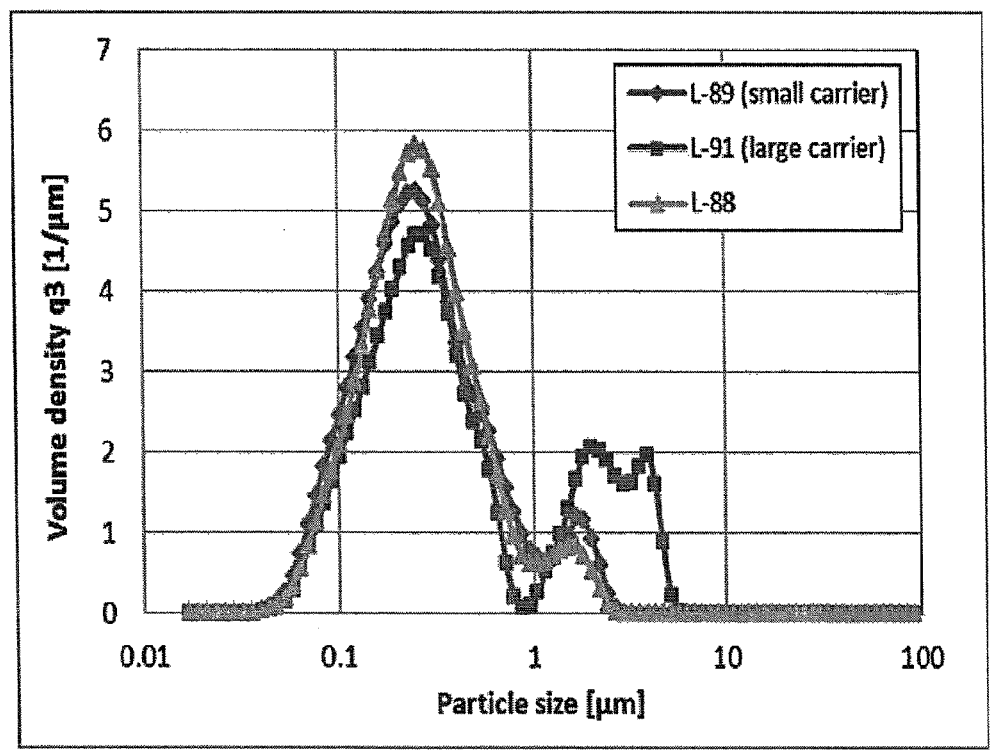
FIG. 28 shows particle size distributions of fenofibrate (FNB) after redispersion from the composite particles following the dispersion test in accordance with Example 28.
Figure 29A:
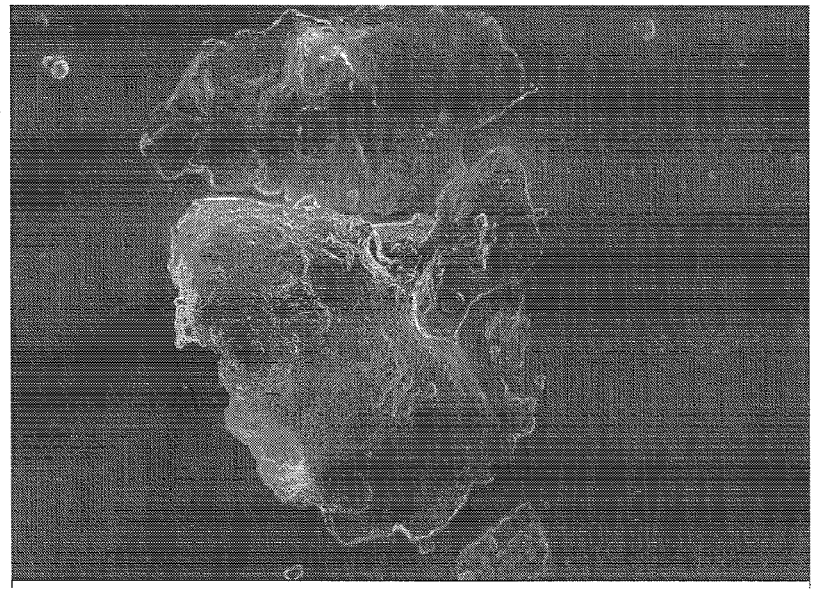
FIGS. 29A-29B show SEM images of composite particles of L-87 (29A) and PS-75 (29B) after redispersion in water in accordance with the procedure in Example 28.
Figure 29B:
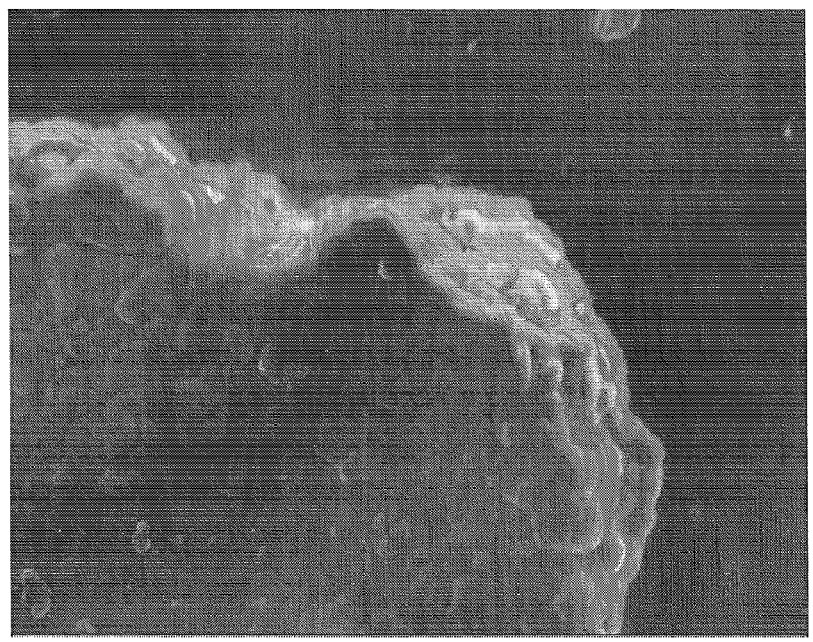

The redispersion behavior was much better in an SDS background solution, which was used in the dissolution tests. High levels of SDS and higher HPMC or mannitol contents were required to achieve complete redispersion of the nanoparticles. In addition, larger carrier particles showed a poorer redispersion behavior. The particle distribution of FNB after distribution from the API composite particles is shown in FIG. 28. The SEM images of dispersed particles are shown in FIGS. 29A-29B.

Example 29

Some API composite powders (particles) were compressed to tablets. A hydraulic Carver press (model: 3851-0, Carver Inc.) was used for tableting. The tablet shape was cylindrical with flat surfaces; the tablet had a diameter of ½ inch. Tablet disintegration tests were carried out by placing the tablet on a small sieve (2 mm screen size) which was placed on top of a beaker filled with water. The beaker was put on a magnetic stirrer and the time was measured until the last parts of the tablet passed through the sieve.

API composite particles L-89 were mixed manually with different excipients such as crospovidone (CP), microcrystalline cellulose (MCC) and magnesium stearate (MgSt). The tablet size was~310 mg. The dispersion time for these tablets is shown in Table 17.

TABLE 17

Dispersion time for FNB tablets

| No. | CP [wrt comp] | MCC [wrt comp] | MgSt [wrt comp] | Pressure [MPa] | | Disintegration time |
|---|---|---|---|---|---|---|
| 1 | — | — | — | 58 | | 10:55 min |
| 2 | 5% | — | — | 58 | | 11:38 min |
| 3 | — | 5% | — | 58 | | 9:54 min |
| 4 | 5% | 5% | — | 58 | | 11:06 min |
| 5 | 10% | 10% | — | 58 | | 10:55 min |
| 6 | 15% | 15% | — | 58 | | 9:40 min |
| 7 | 15% | 15% | 0.2% | 58 | | 10:30 min |
| 8 | 15% | 15% | 0.2% | 39 | | 12:28 min |
| 9 | 15% | 15% | 0.2% | 39 | LabRam 1 min, 60 G's | 11:13 min |
| 10 | 15% | 15% | 0.2% | 39 | +1% M5P, LabRam 1 min, 60 G's | 5:35 min |

The disintegration and dissolution behavior of different API composite powders was investigated. Tableting conditions were: a compression pressure of 77.4 MPa (load: 1 t), a dwell time of 2 seconds, and a tablet mass of~310 mg. The results are given in Table 18.

TABLE 18

Disintegration and dissolution behavior of different API composite powders

| Exp. | Fluid bed suspensions FNB | HPMC | SDS | Mannitol | ~d50 | AR | Assay | Disintegration time 77.4 MPa, 2 sec | Comments |
|---|---|---|---|---|---|---|---|---|---|
| L-87 | 30% | 5% | 0.75% | 50% | 170 nm | 26.9% | 14.3% | ~7 min | |
| L-88 | 20% | 25% | 5% | — | ~200 nm | 37% | 15.3% | ~29 min | complete redispersion |
| L-89 | 30% | 10% | 5% | 50% | 165 nm | 25.6% | 14.2% | ~12 min | complete redispersion, fast dissolution |

TABLE 18-continued Disintegration and dissolution behavior of different API composite powders

| | Fluid bed suspensions | | | | | | Disintegration time 77.4 MPa, | |
|---|---|---|---|---|---|---|---|---|
| Exp. | FNB | HPMC | SDS | Mannitol | ~d50 | AR | Assay | 2 sec | Comments |
| L-91 | 30% | 10% | 5% | 50% | 170 nm | 31.8% | 14.7% | ~10 min | Larger carrier particles |
| L-93 | 30% | 10% | 5% | — | 210 nm | 24.5% | 15.6% | ~29 min | |
| PS-70 | 20% | 5% | 0.75% | — | 165 nm | 5.7% | 13.5% | 16 sec | |

Figure 30:
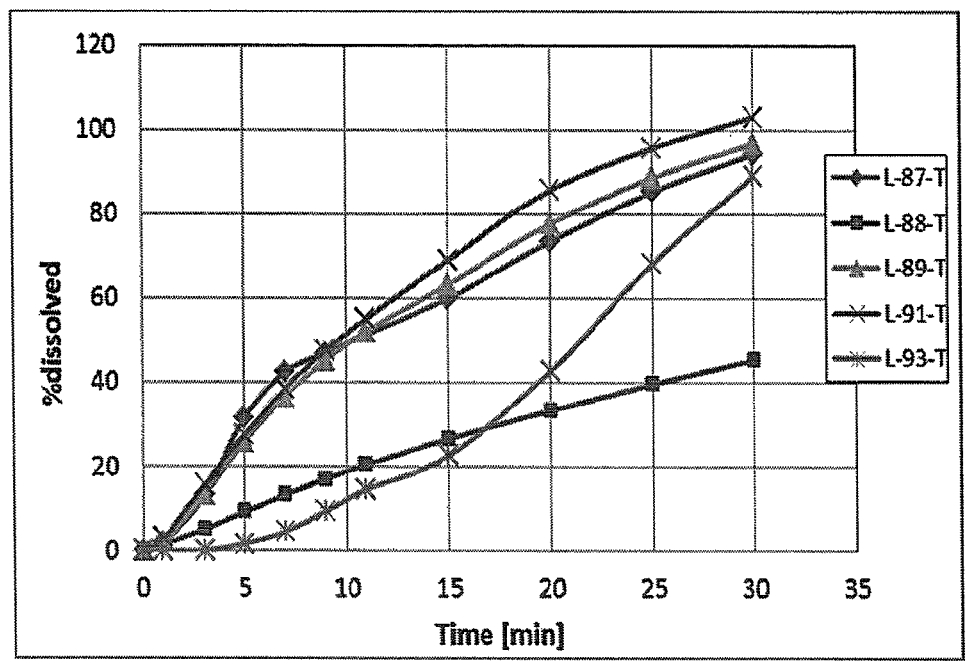
FIG. 30 shows dissolution profiles of various composite particles compressed into tablets in a dissolution test in accordance with Example 29.

The dissolution profiles of these API composite particles are shown in FIG. 30.

Example 30

In this example, different dry coating methods are compared. The dry-coated carrier particles were studied to determine whether they were fluidizable. The results are given in Table 19.

TABLE 19

Dry-coated carrier particles with enhanced fluidizability

| Carrier type | (d50) mm | Silica type | Silica loading | Coating method | FFC | Fluidizable? |
|---|---|---|---|---|---|---|
| Corn Starch | 15 | — | — | — | — | No |
| | | M5P | 0.56 | LabRAM | >10 | Yes |
| Potato Starch | 34 | — | — | — | 3 | No |
| | | M5P | 0.17 | Comil | >10 | Yes |
| Lactose Granulac 230 | 18 | — | — | — | — | No |
| | | M5p | 1.00 | LabRAM | 4.7 | No |
| Lactose Granulac 200 | 28 | — | — | — | 2.5 | No |
| | | M5p | 1.00 | LabRAM | 5.2 | Yes |

Example 31

In this example, the size change for the carrier particles after fluid bed coating was studied. Dry coated corn starch, potato starch and lactose were fluid bed coated with a fenofibrate nanosuspension prepared in the stirred media mill containing 20% or 30% FNB, 5% HPMC with respect to API, 0.75% SLS with respect to API. The results are shown in Table 20.

TABLE 20

Particle size change after fluid bed coating

| | | Particle Size | | |
|---|---|---|---|---|
| Sample | Carrier | Initial $d_{10}, d_{50}, d_{90}$ | Final $d_{10}, d_{50}, d_{90}$ | Assay (%) |
| PS-70 | PS | 17, 36, 60 | 20, 37, 58 | 13.5 |
| CS-83 | CS | 8, 15, 23 | 10, 28, 72 | 29.6 |
| L-85 | Lactose | 4, 30, 98 | 32, 64, 114 | 15.6 |

Example 32

In this example, the size change for the carrier particles after fluid bed coating was studied. Dry coated corn starch, potato starch and lactose were fluid bed coated with a fenofibrate nanosuspension prepared in the stirred media mill containing 20% FNB, 5% HPMC with respect to API, 0.75% SLS with API. The results are shown in Table 21.

Size results show that lactose can be sprayed with both 20 and 30% fenofibrate nanosuspensions without a significant change in the agglomerate size. These high concentrations suggest that high drug loadings can be sprayed without adverse effects, which will result in significant reductions in processing time in terms of milling and fluid bed coating.

TABLE 21

Particle size change after fluid bed coating

| | | Particle Size | | |
|---|---|---|---|---|
| Sample | FNB conc (%) | Initial $d_{10}, d_{50}, d_{90}$ | Final $d_{10}, d_{50}, d_{90}$ | Assay (%) |
| L-85 | 20 | 4, 30, 98 | 32, 64, 114 | 15.6 |
| L-87 | 30 | 4, 30, 98 | 31, 65, 105 | 14.3 |

Example 33

In this example, dry-coated lactose, potato starch and corn starch were fluid bed coated with a fenofibrate nanosuspension. Samples of the fluid bed coated powders were assayed in acetone to characterize the content uniformity associated with various different carrier particles. The results are shown in Table 22. It was observed that the fluid bed coated composite particles have good content uniformity.

TABLE 22

Particle size change after fluid bed coating

| Carrier | Initial $d_{10}, d_{50}, d_{90}$ | Exp # | Final $d_{10}, d_{50}, d_{90}$ | Assay Average (%) | RSD (%) | Number of samples |
|---|---|---|---|---|---|---|
| Potato Starch | 17, 36, 60 | PS-75 | — | 13.1 | 3.8 | 8 |
| Corn Starch | 8, 15, 23 | CS-84 | 11, 22, 41 | 9.75 | 2.0 | 3 |
| Lactose, Granulac 200 | 4, 30, 98 | L-89 | 18, 69, 123 | 14.2 | 1.6 | 7 |

Example 34

Figure 31:
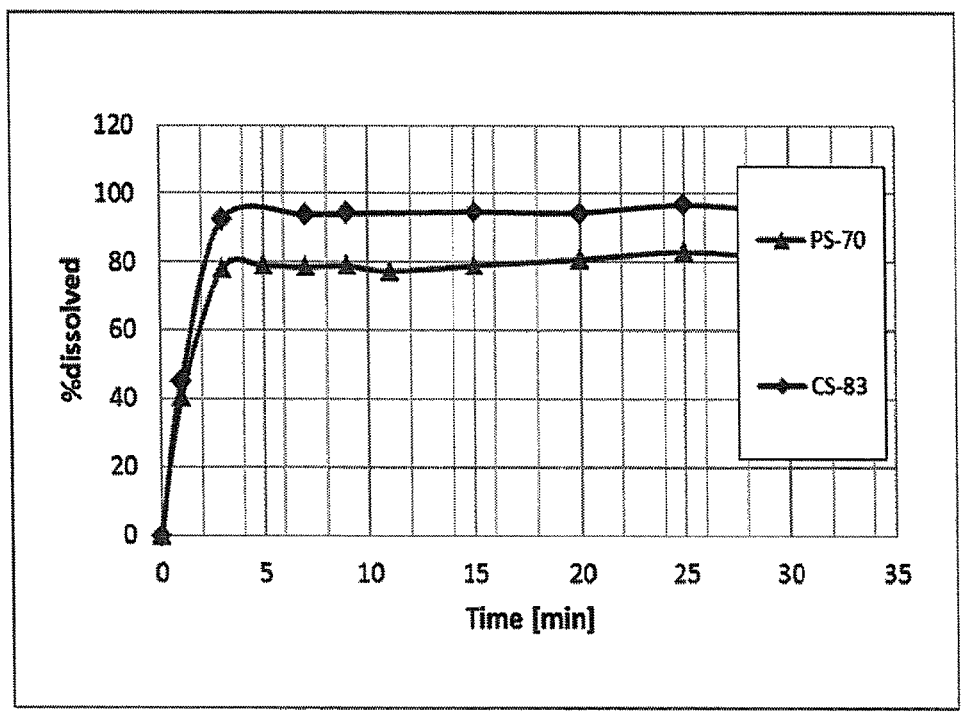
FIG. 31 shows dissolution profiles of two composite particles having different carrier particles in a dissolution test in accordance with Example 34.

In this example, API composite particles with different carrier particles: PS and CS, were tested for their dissolution profiles. The results are shown in FIG. 31. The small size and the high surface area of the corn starch particle allowed for much faster dissolution of the fenofibrate particle than was the case for the potato starch.

Example 35

Figure 32:
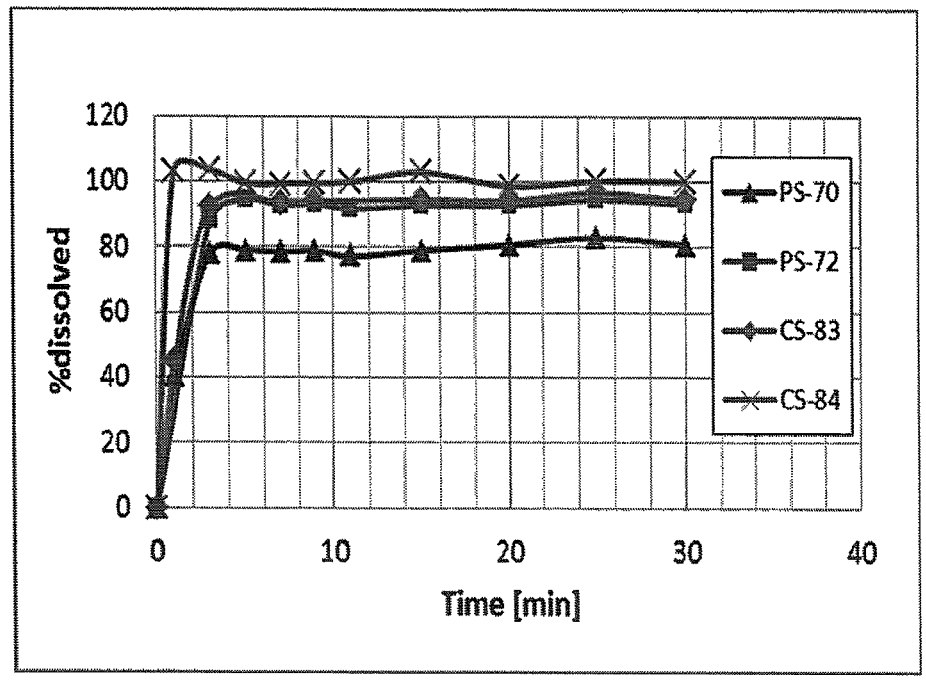
FIG. 32 shows dissolution profiles of composite particles with mannitol added in a dissolution test in accordance with Example 35.

In this example, mannitol was added to the API nanosuspension before fluid bed coating. Mannitol as a matrix former can improve the initial dissolution of the fenofibrate and prevent incomplete dissolution. The dissolution profiles of the API composite particles are shown in FIG. 32. The presence of the mannitol significantly improves the dissolution of the composite particle when both corn starch and potato starch were used as the carrier particle. The dissolution of fenofibrate from the corn starch carrier particle in the presence of mannitol allowed the fenofibrate to completely dissolve in less than 1 minute.

Example 36

In this example, the fenofibrate nanosuspension, containing mannitol, was fluid bed coated onto lactose, and potato starch particles to see if the dissolution could be improved by using a fine, soluble carrier particles. The coating conditions are listed in Table 23.

TABLE 23

Fluid bed coating with different carrier particles

| | Fluid bed suspensions | | | | Carrier Size | |
|---|---|---|---|---|---|---|
| Exp. | FNB | HPMC | SDS | Mannitol | d50 | Assay |
| PS-72 | 20% | 5% | 0.75% | 50% | 34 | 11.9% |
| L-86 | 20% | 5% | 0.75% | 50% | 28 | 13.3% |

Figure 33:
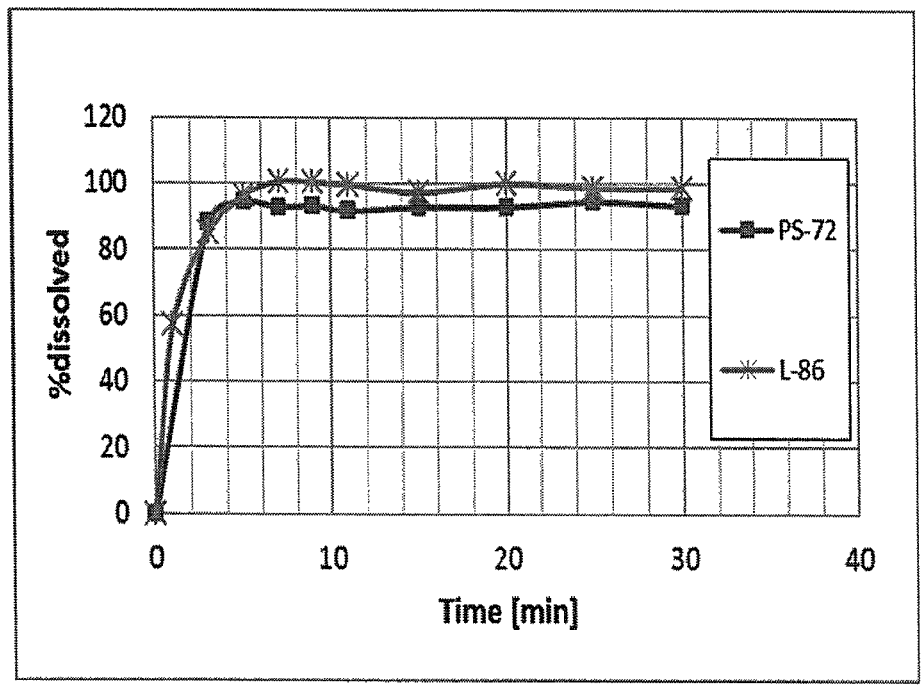
FIG. 33 shows dissolution profiles of composite particles PS-72 and L-86 in a dissolution test in accordance with Example 36.

The dissolution results indicate that the water soluble carrier was indeed able to improve the dissolution of the fenofibrate from the composite particle. FIG. 33. The lactose (28 mm) and potato starch (35 mm) particles showed a comparable dissolution profile at early times. The water soluble lactose particle did not cake at the bottom of the dissolution vessel and allowed for complete dissolution.

Example 37

In this example, the fenofibrate nanosuspensions prepared by different methods were compared to determine their effects on the dissolution profile of lactose fluid bed coated with the FNB suspensions prepared by:
  Stirred media mill: L-88: 20% FNB, 25% HPMC, 5% SDS~160 nm
  Stirred media mill: L-89: 30% FNB, 10% HPMC, 5% SDS, 50% mannitol~160 nm
  LASP: L-94: 14.8% FNB, 19.2% HPMC, 7.7% SDS, 50% mannitol; d50~3 µm.

Figure 34:
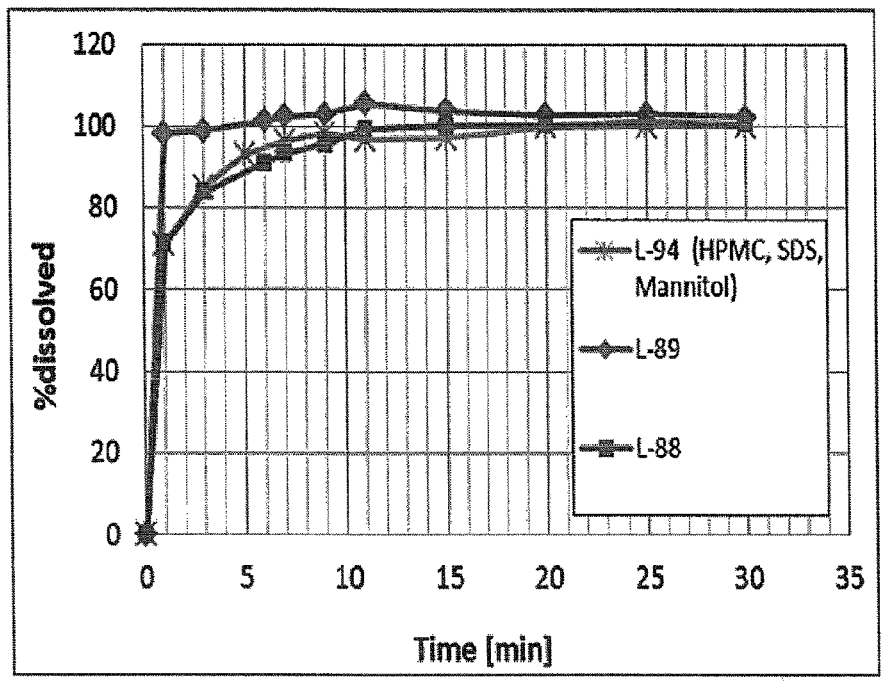
FIG. 34 shows dissolution profiles of composite particles with different added materials in a dissolution test in accordance with Example 37.

The dissolution profiles of the resultant FNB composite particles are shown in FIG. 34. The dissolution results show that even though the fenofibrate particles produced in the LASP (1-94, 3 mm) process are much larger than those produced by stirred media milling (1-88/1-89, 0.16 mm), 85% of the fenofibrate still dissolves in less than 5 minutes. The dissolution results suggest that the high polymer concentrations required in LASP limit the dissolution of the fenofibrate.

Example 38

Figure 35:
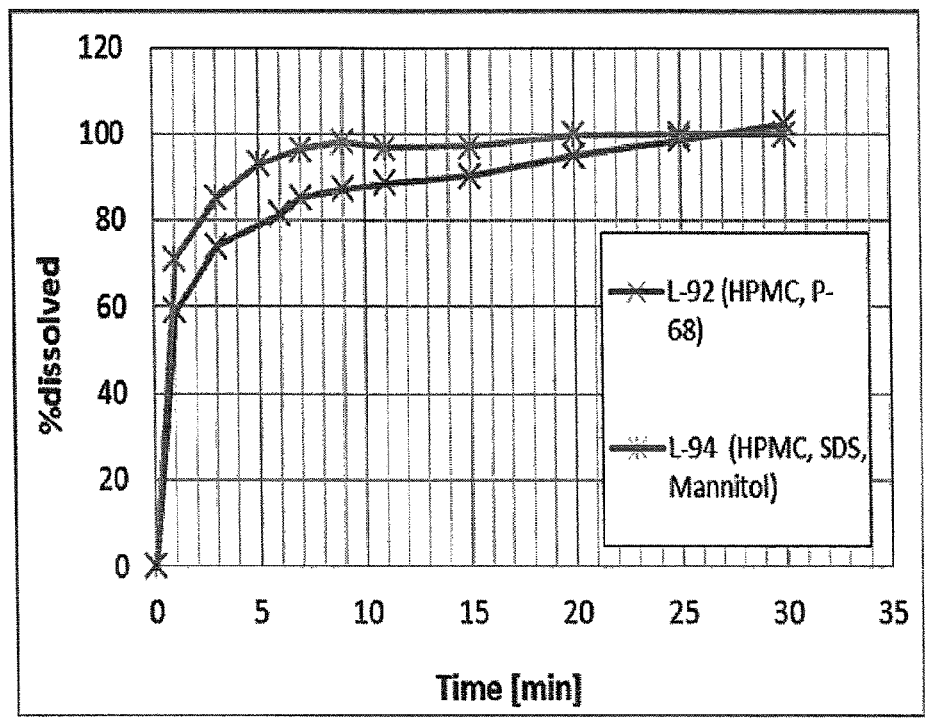
FIG. 35 shows dissolution profiles of composite particles with different matrix-forming materials in a dissolution test in accordance with Example 38.

In this example, the effect of LASP formulation on the dissolution of FNB composite particles (lactose carrier) was studied. Two LASP formulations were used:
  Formulation 1, L-92: 9.3% FNB, 25% HPMC, 50% P-68; d50~1.1 µm
  Formulation 2: 14.8% FNB, 19.2% HPMC, 7.7% SDS, 50% mannitol; d50~3 µm The dissolution profiles of the API composite particles are shown in FIG. 35. Even though the use of P-68 leads to significantly smaller particles, this polymeric surfactant significantly slows down the dissolution of the fenofibrate in the API composite particles.

Example 39

In this example, dry-coating of lactose particles (GranuLac 200) was carried out in the acoustic mixer LabRAM. Both, host and guest particles were filled into the mixing chamber without any pre-blending. A total batch size of 150 g of powder was processed in the mixer. This mass results in a filling level of about 50% in the 500 mL mixing jar. The process conditions and the resulting FFC's are summarized for different silica loadings in Table 24.

TABLE 24

Flow properties of GranuLac 200 before and after dry-coating

| Silica Content (%) | Time (min) | Intensity (%) | Acceleration (G's) | FFC |
|---|---|---|---|---|
| 0 | — | — | — | 2.5 |
| 1 | 10 | 100 | 68 | 5.2 |
| 1.5 | 10 | 100 | 68 | 6.0 |

An improvement in the flow properties with increasing silica content is observed. The coating with 1% and 1.5% M5P allows fluidization of the lactose particles. At a content of 1% M5P a theoretical SAC of 350% and at 1.5% M5P a theoretical SAC of 530% are achieved, respectively. The irregular shape and the wide size distribution of the GranuLac 200 limit the improvement of the flowability.

Example 40

In this example, the water content of the composites was examined by thermogravimetric analysis, using a TGA/DSC 1, Star$^e$ system (Mettler-Toledo, Columbus, Ohio) with nitrogen purging. Samples were heated to 110° C. at a constant rate of 10° C./min The weight loss in percent due to water evaporation was subsequently calculated and defined as the moisture content. The moisture content of fluid bed coated composites is summarized in Table 25.

TABLE 25

Moisture content of fluid bed coated composites

| Composite No. | Formulation | Moisture content (%) |
|---|---|---|
| PS-70 | 20% FNB, 5% HPMC, 0.75% SDS | 10.91 |
| PS-72 | 20% FNB, 5% HPMC, 0.75% SDS, 50% Mann | 8.05 |
| CS-84 | 20% FNB, 5% HPMC, 0.75% SDS, 50% Mann | 5.54 |
| L-89 | 30% FNB, 10% HPMC, 5% SDS, 50% Mann | 1.61 |
| L-87b | 30% FNB, 5% HPMC, 0.75% SDS, 50% Mann | 0.41 |

Composites with lactose carriers have low moisture contents as compared to other composites. It is advantageous to have a process and materials leading to lower moisture contents. The quality, hardness, compaction and shelf life of pharmaceuticals depends, to a large extent, on the water content. High moisture content may cause sticking, poor flow and stability issues. If composites have a high moisture content, tablets made from the composites will also have a high moisture content. In the presence of moisture, a solid dosage form may lose its color or physical integrity. Sometimes, if a tablet has a high moisture content, excipients in the tablet may serve as nutrient media for the growth of microorganisms. If the moisture content is too low, this may cause capping/lamination and/or tablet roughness.

Example 41

In this example, tablets were made from composites without additional excipients. This example illustrates the ease of tablet formation from the composites formed using the claimed process; and illustrates their exemplary performance. A Carver hydraulic press (model: 3851-0, Carver Inc.) was used for tableting. The tablet shape was cylindrical with flat surfaces. The tablet had a diameter of ½ inch. The dwell time was 2 seconds. Two different loads were used (77.4 MPa & 38.7 MPa). The disintegration time was measured and dissolution was performed. Tablet disintegration tests were carried out by putting the tablet in a small sieve (2 mm screen size) placed on top of a beaker filled with 600 ml of deionized (DI) water. The beaker was placed on a magnetic stirrer, and the time was measured until the last parts of the tablet passed through the sieve. The disintegration time of tablets of different composites was measured and is given in Table 26. Tablet dissolution was done in USP II, and SDS solution was used as the dissolution media. The size of the filter used was 0.45 μm. The comparison of the dissolution of tablets made from different composite powders is presented in FIG. 37.

TABLE 26

Disintegration time of tablets made from fluidized bed coated composites of different carriers

| Composite No. | FNB | HPMC | SDS | Mannitol | Load [MPa] | Disintegration time |
|---|---|---|---|---|---|---|
| L-89 | 30% | 10% | 5% | 50% | 77.4 | 10:55 min |
| L-89 | 30% | 10% | 5% | 50% | 38.7 | 6:50 min |
| CS-84 | 20% | 5% | 0.75% | 50% | 38.7 | 2.5 min |
| PS-72 | 20% | 5% | 0.75% | 50% | 38.7 | 44 Sec |
| PS-70 | 20% | 5% | 0.75% | — | 38.7 | 14 Sec |

Figure 37:
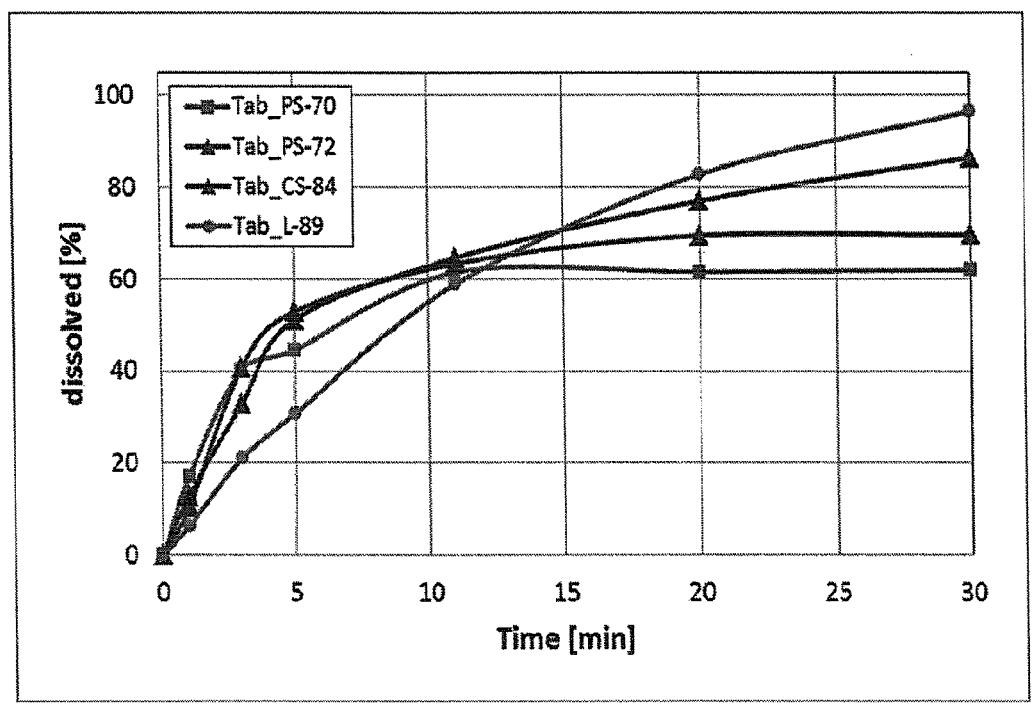
FIG. 37 shows a comparison of the dissolution of tablets of different composite powders in a dissolution test carried out in accordance with Example 41.

The disintegration time for lactose tablets could be further improved to make them comparable in dissolution properties with the original composite powders, before forming a tablet from them. The short disintegration time for PS & CS has an advantage over lactose during the first 10 minutes (FIG. 37). However, faster release of nanoparticles from the composite dominates after that time. Additional surfactant leads to faster drug particle release (sample L-89 had 5% surfactant compare to 0.75% for CS & PS composites). Moreover, for sample L-89 there were no caking issues in water soluble carriers such as lactose, which occurred in the case of PS & CS.

Example 42

Figure 38A:
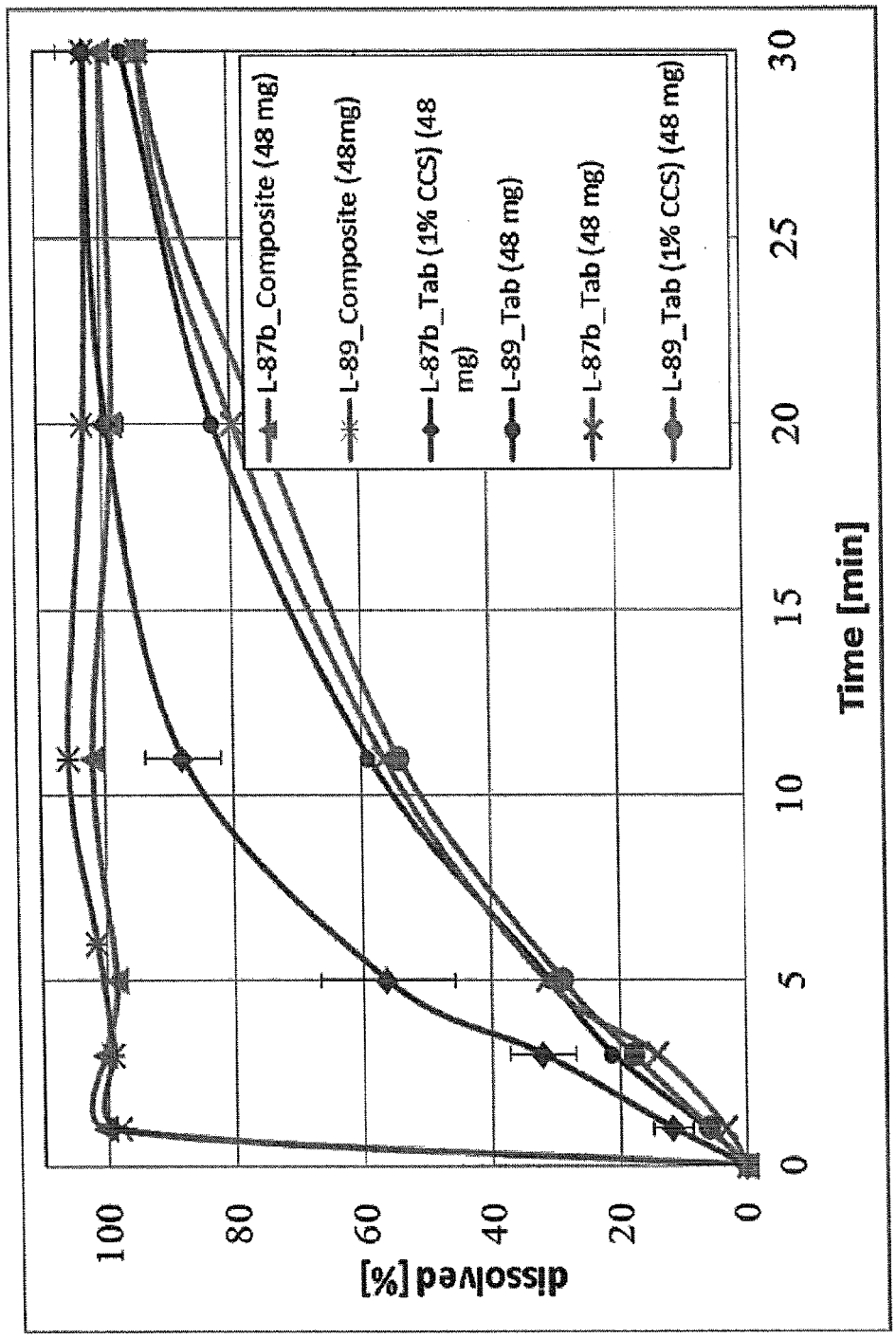
FIGS. 38A-38B show a comparison of dissolution profiles for composite powders and tablets of samples L-87b & L-89 in FIG. 38A, and tablets of samples L-87b & L-89 composite powders with Tricor Tablet in SDS media in FIG. 38B as carried out in accordance with Example 42.
Figure 38:
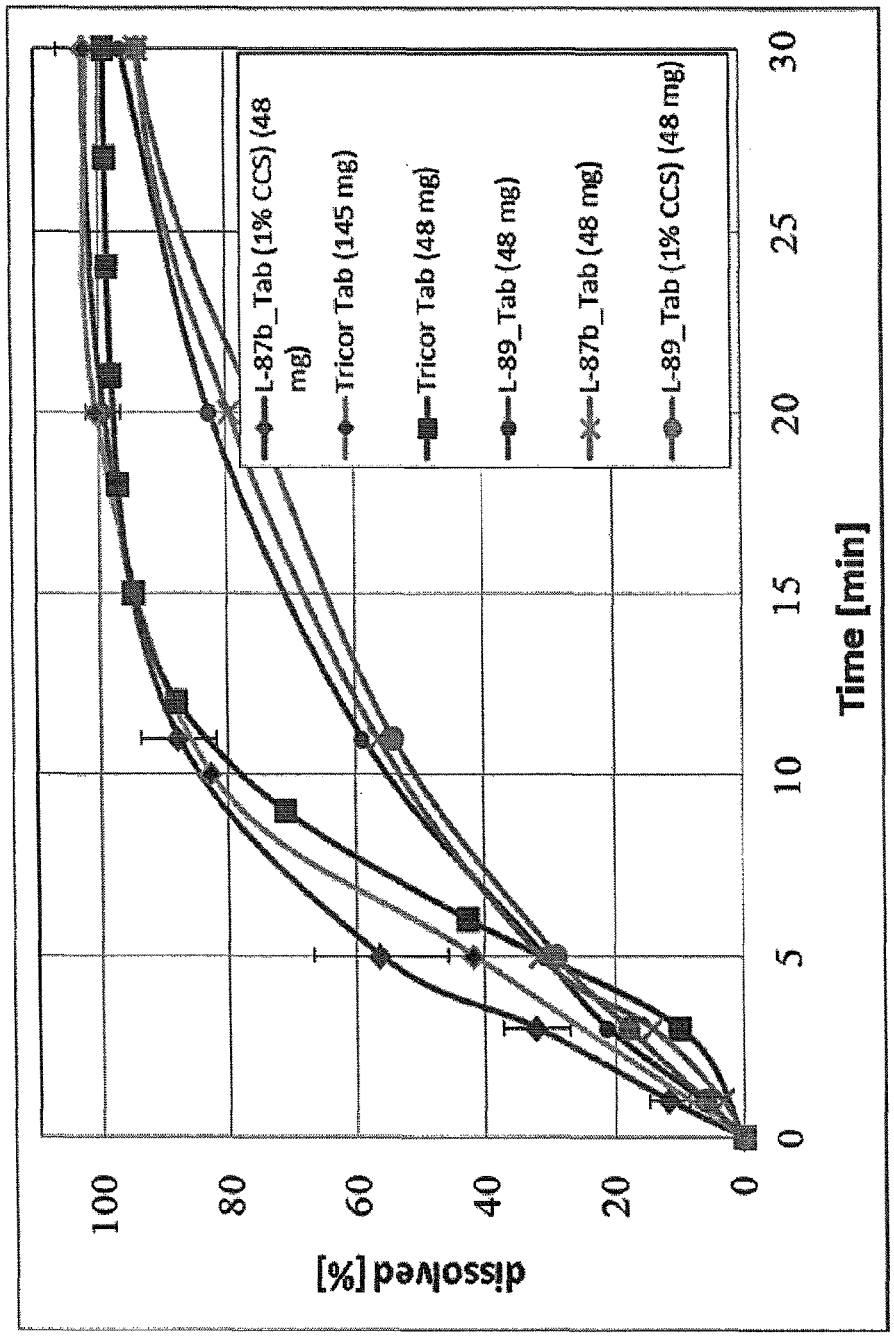

In this example, tablets were made from lactose composites. Extra granular superdisintegrant powders were used for improving the disintegration time. The superdisintegrant concentration or the amount of superdisintegrant used was optimized. The tablet dissolution was done in USP II and SDS solution was used as the dissolution media. The comparison of the dissolution of tablets of different composite powders is presented in FIG. 38A. The dissolution profiles of tablets from composites (samples L-87b & L-89) were compared with a currently marketed Tricor tablet. That comparison is presented in FIG. 38B.

The tablet made from the L-87b composite with CCS (1%) had better dissolution properties than the tablet made from the L-89 composite. For the tablet made from the L-87b composite, about 80% of the drug dissolved in less than 10 minutes. There was no improvement in dissolution for tablets made from L-89 composites using CCS. The dissolution properties of the tablet made from the L-87b composite with 1% CCS is comparable with Tricor tablets.

Example 43

Figure 39:
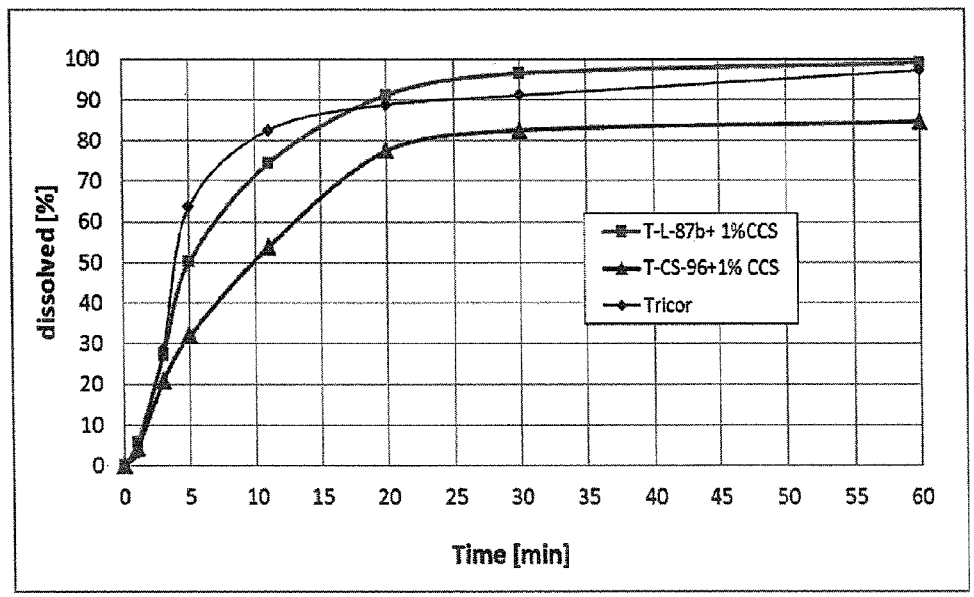
FIG. 39 shows comparisons of the dissolution of samples L-87b, CS-96 and Tricor tablets in buffer solution with 10 mM SDS solution as carried out in accordance with Example 43.

In this example, tablets were made from L-87b and CS-96 composites. Tablets were prepared using composites with 1% CCS and 6.25% SDS (with respect to FNB). Additional SDS was not included in the composites but rather was added to the blend before making the tablets. Additional SDS made the total SDS concentration 7% (with respect to FNB) which is the same as for the Tricor tablet. Dissolution of the tablets was compared with the commercial Tricor Tablet. The dissolution medium was 0.01 M sodium phosphate buffer with 10 mM SDS. Dissolution profiles of all three tablets were compared and are shown in FIG. 39. Dissolution of both tablets made from the L-87b composite and the Tricor tablets was comparable. In particular, the dissolution rate was more favorable for tablets made from the L-87b composite after 20 minutes of dissolution time.

Example 44

In this example, the hardness of tablets made from the composites was measured. In the first batch, the tablets were made from nanocomposite powders without any added excipients. Tablet weights were in the range of 328-418 mg (~48 mg FNB). A Carver press was used to make the tablets. Dwell time was 2 seconds. The test was carried out using a Dr. Schleuniger (Model-6D) hardness tester. The test results are summarized in Table 27. In the second batch, tablets were prepared by adding 1% Mg-St and 1% CCS to nanocomposite powders. The load applied during tableting was 38.7 MPa. These test results are summarized in Table 28.

TABLE 27

Hardness of tablets prepared from different composites without additional excipients

| Composite No | Hardness (Kp) Load applied during tableting (MPa) | | |
|---|---|---|---|
| | 77.4 | 38.7 | 19.35 |
| L-87b | 5.63 | 3.03 | 2.30 |
| L-89 | 4.8 | 3.80 | 2.25 |
| CS-84 | 3.7 | 2.25 | 0.90 |
| PS-72 | 3.0 | 1.63 | 0.75 |
| PS-70 | 2.2 | 0.55 | 0.40 |

TABLE 28

Hardness of tablets made from composites with excipients

| Composite No. | Hardness (Kp) | |
| --- | --- | --- |
| | Without excipients | With excipients |
| L-89 | 3.80 | 2.95 |
| L-87b | 3.03 | 3.5 |
| CS-84 | 2.25 | 1.85 |
| PS-72 | 1.63 | 1.2 |

It was observed from the data in table 27, that lower compaction loads resulted in a lower the hardness of the tablet. For all composites, a similar observation was found. PS composites have the lowest tablet hardness. This effect was also observed in the disintegration test. The PS tablet had the shortest disintegration time. Addition of excipients to the composites further reduces the tablet hardness, except for tablets made from the L-87b composites (Table 28).

Example 45

Figure 40:
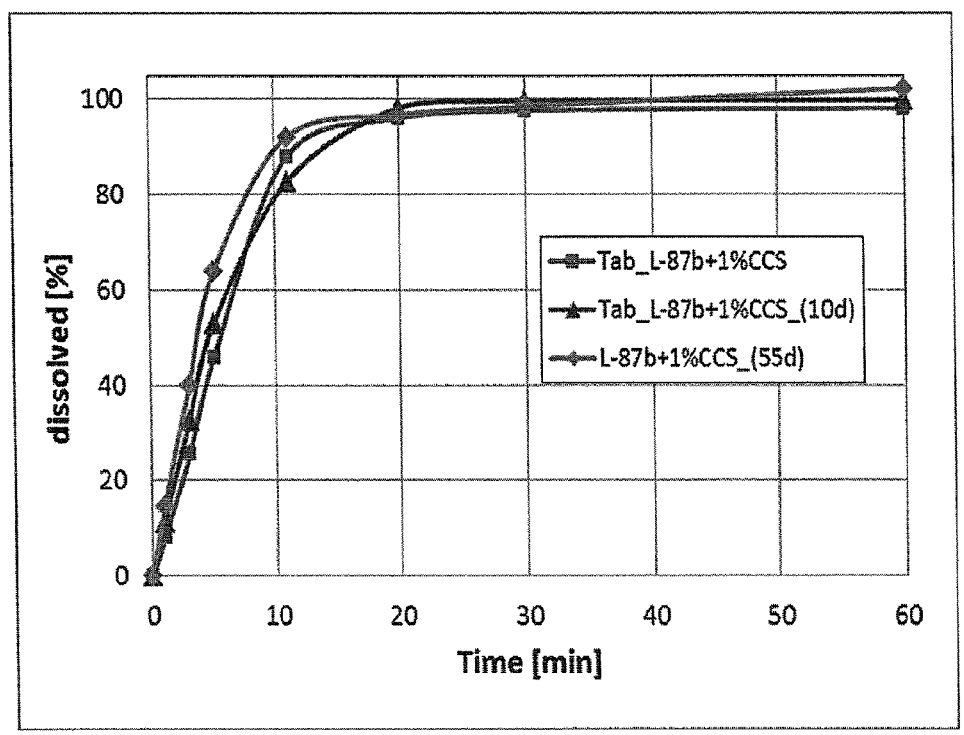
FIG. 40 shows dissolution profiles of tablets of sample L-87b composites. The tablet dissolution was measured after storage for several different time periods to investigate degradation of the tablet made in accordance with Example 45.

In this example, tablets made from the L-87b composite were tested for degradation in order to examine the extent of degradation that the nano-composites may undergo during storage. Tablets prepared from the L-87b composites were tested for degradation in storage at room temperature for a period of time. These tablets were also made using the Carver press. Tableting and dissolution conditions were the same as in Example 44. The dissolution medium was a 25 mM SDS solution. The degradation of the tablets was assessed based on examination of the changes in the dissolution profiles after storage as compared to the original dissolution profile and those results are shown in FIG. 40. As seen, there was no difference in dissolution behavior observed after 10 and 55 days. Hence, these nanocomposite powders do not exhibit any degradation in the tablet.

Example 46

Figure 41:
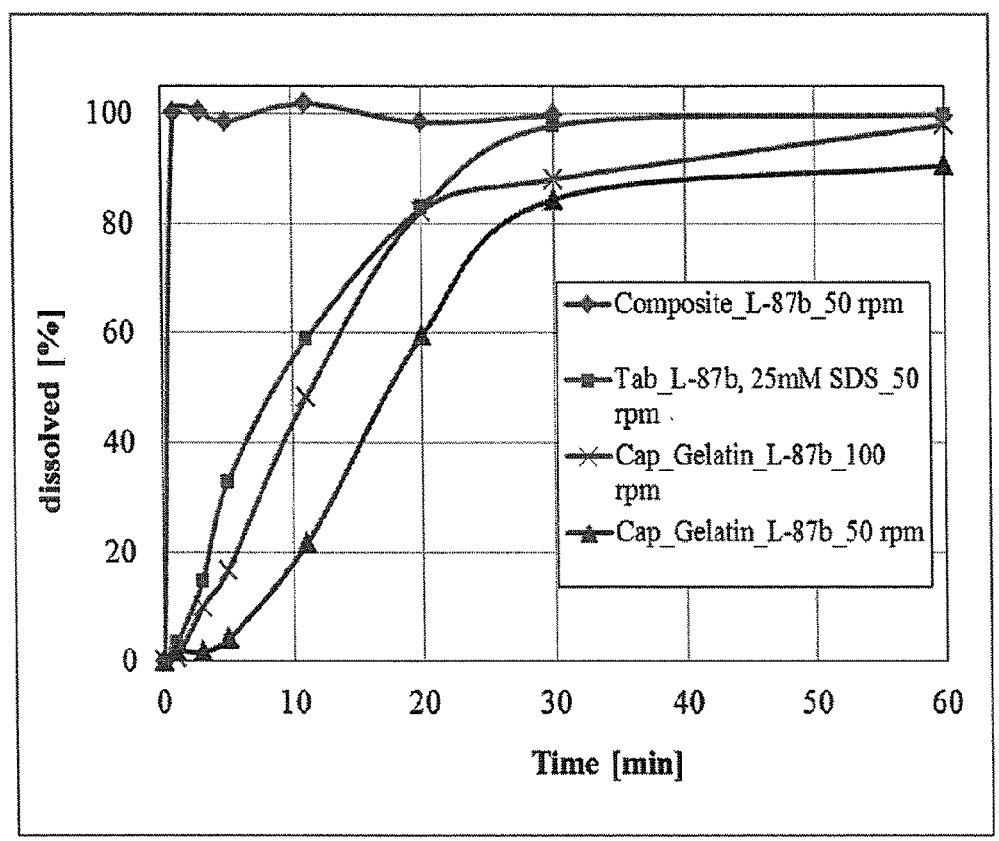
FIG. 41 shows a comparison of dissolution profiles of capsules having sample L-87b composites made in accordance with Example 46.

In this example the dissolution of a capsule filled with the lactose composite was examined. "0" size gelatin capsule was used for this purpose. The capsule was filled with composite powders equivalent to 48 mg FNB dosage. Each capsule was filled manually. Dissolution testing was done in USP II. For capsule dissolution a 40 mesh basket with an adapter was used. The paddle speed was maintained at 50 rpm (comparable with the tablet dissolution tests) and 100 rpm (generally prevalent in the literature). The dissolution media used was 25 mM SDS solution. The other operating conditions were kept the same as for the tablet dissolution tests described above. The dissolution profiles are shown in FIG. 41.

Capsule dissolution obtained was found to be slower than tablet dissolution when the 50 rpm paddle speed was used. However, capsule dissolution was improved relative to table dissolution when the 100 rpm paddle speed was used. It was observed that capsule shell fractions were stuck on the bottom surface of the adapter and thus blocked powder dissolution, thereby interfering with the potential dissolution of the nanocomposite powders.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A composite particle comprising:
   a core, wherein the core is a particle having median particle size in a range of from about 20 μM to about 200 μM and
   an outer layer comprising nanoparticles of an ingestible material and at least one matrix-forming material,
   a fluidizing material layer located between the core and the outer layer, wherein the fluidizing material comprises nanoparticles, and
   the ingestible material comprises at least one active pharmaceutical ingredient.

2. The composite particle of claim 1, wherein the core comprises a material selected from starch, lactose, sucrose, cellulose, cellulose ethers and mixtures thereof.

3. The composite particle of claim 1, wherein the fluidizing material comprises nanoparticles of a material selected from silica, alumina, titania, carbon black, aluminum calcium silicate, calcium silicate, magnesium silicate, potassium silicate, sodium silicate, sodium aluminosilicate, sodium calcium aluminosilicate, tricalcium silicate, silica aerogel, talc, iron oxide, other metal oxides and mixtures thereof.

4. The composite particle of claim 1, wherein the fluidizing material has a dispersive surface energy of less than 60 mJ/m$^2$ and a median particle size of 5 nm to 100 nm.

5. The composite particle of claim 4, wherein the fluidizing material comprises silica nanoparticles.

6. The composite particle of claim 1, wherein the ingestible material comprises said at least one active pharmaceutical ingredient in range 0.01 to 50 wt %.

7. The composite particle of claim 6, wherein the ingestible material particles have a size in the range of from about 10 nm to about 1000 nm.

8. The composite particle of claim 7, wherein the ingestible material particles have a size in the range of from about 10 nm to about 200 nm.

9. The composite particle of claim 1, wherein the matrix-forming material comprises at least one polymer.

10. The composite particle of claim 9, wherein at least one polymer is selected from the group consisting of hydroxypropylcellulose, hydroxypropyl methylcellulose, poly(vinyl alcohol), poly(vinyl pyrrolidone, ammonio methacrylate copolymers, ethylcellulose, hydroxyl methyl celluolose, hydroxyethyl cellulose, methyl cellulose, carboxymethyl cellulose sodium salt, gum acacia and combinations thereof.

11. The composite particle of claim 10, wherein at least one surfactant is selected from the group consisting of sodium dodecyl sulfate, dioctylsulfosuccinate, ethylene oxide/propylene oxide copolymers, cetyltrimethylammonium bromide, polyethylene sorbitol esters, sodium alginate, lecithin, sodium lauryl sulfate, monooleate, monolaurate, monostearate, stearylic alcohol, cetostearylic alcohol, tyloxapol, polyethoxylated castor oil, and mixtures thereof.

12. A process for preparing a composite particle, comprising the steps of:
   preparing a suspension of nanoparticles of an ingestible material and at least one matrix-forming material; and
   fluid bed coating the suspension onto carrier particles having a median particle size in a range of from about 20 μM to about 200 μM, and
   a step of dry coating the carrier material with a fluidizing material prior to the fluid bed coating step, and wherein the ingestible material comprises at least one active pharmaceutical ingredient.

13. The process of claim 12, wherein the carrier particles comprise a material selected from starch, lactose, sucrose, cellulose, cellulose derivatives and mixtures thereof.

14. The process of claim 12, wherein the nanoparticles have a median particle size in the range of from 5 nm to 100 nm.

15. The process of claim 12, wherein the nanoparticle material is selected from the group consisting of silica, alumina, titania, carbon black, aluminum calcium silicate, calcium silicate, magnesium silicate, potassium silicate, sodium silicate, sodium aluminosilicate, sodium calcium aluminosilicate, tricalcium silicate, silica aerogel, talc, iron oxide, other metal oxides and mixtures thereof.

16. The process of claim 12, wherein the dry coating is performed for a time sufficient to achieve a surface area coverage of the carrier material of from 35% to about 100%.

17. The process of claim 16, wherein the fluidizing material comprises from 0.1% to 10% of a total weight of the fluidizing material and carrier material.

18. The process of claim 12, wherein the active pharmaceutical ingredient comprises from 5% w/v % to 50 w/v % of a total weight of the suspension.

19. The process of claim 12, wherein the active pharmaceutical ingredient containing particles have a size in the range of from about 10 nm to about 1000 nm.

20. The process of claim 12, wherein a solvent used in the suspension is selected from tertiary butyl alcohol (TBA), tetrahydrofuran (THF), dimethyl sulfoxide (DMSO), dichloromethane, dimethyl formamide (DMF), methanol and mixtures thereof.

21. The process of claim 12, wherein a solvent used in the suspension comprises water.

22. The process of claim 21, wherein the suspension comprises at least one matrix-forming material and a surfactant.

23. The process of claim 12, wherein the at least one matrix-forming material comprises a polymer.

24. The process of claim 23, wherein the polymer is selected from the group consisting of hydroxypropylcellulose, hydroxypropyl methylcellulose, poly(vinyl alcohol), poly(vinyl pyrrolidone), poly(vinyl pyrrolidone)-K360, poly(vinyl pyrrolidone)-K30, ammonio methacrylate copolymer, ethylcellulose and combinations thereof.

25. The process of claim 23, wherein the suspension further comprises a non-ionic surfactant.

26. The process of claim 23, wherein the surfactant is selected from the group consisting of sodium dodecyl sulfate, dioctylsulfosuccinate, poloxamer 188, cetyltrimethylammonium bromide, poloxamer 407, polyethylene sorbitol ester, sodium alginate.

27. The process of claim 14, wherein the at least one matrix-forming material comprises from 5 w/v % to 50 w/% of the nanosuspension.

28. The process of claim 12, wherein the fluid bed coating step uses a fluidizing velocity in a range of from 1 cm/s to 10 cm/s.

29. The process of claim 12, wherein the fluid bed coating step uses a fluidizing flow rate in a range of from 0.1 cfm to 5 cfm.

30. The process of claim 12, wherein the fluid bed coating step uses an atomization pressure in a range of from 5 psig to 35 psig to atomize the suspension.

* * * * *